(12) United States Patent
Vandenburg et al.

(10) Patent No.: US 11,621,515 B2
(45) Date of Patent: Apr. 4, 2023

(54) CONNECTOR ASSEMBLY FOR ACTIVE IMPLANTABLE MEDICAL DEVICE

(71) Applicant: NeuroPace, Inc., Mountain View, CA (US)

(72) Inventors: Joseph Vandenburg, Bethesda, MD (US); Jerzy Sochor, Sunnyvale, CA (US)

(73) Assignee: NeuroPace, Inc., Mountain View, CA (US)

( * ) Notice: Subject to any disclaimer, the term of this patent is extended or adjusted under 35 U.S.C. 154(b) by 79 days.

(21) Appl. No.: 17/213,138

(22) Filed: Mar. 25, 2021

(65) Prior Publication Data

US 2022/0311173 A1 Sep. 29, 2022

(51) Int. Cl.
| | |
|---|---|
| *H01R 13/40* | (2006.01) |
| *H01R 13/518* | (2006.01) |
| *A61N 1/375* | (2006.01) |
| *H01R 13/52* | (2006.01) |
| *A61N 1/36* | (2006.01) |

(52) U.S. Cl.
CPC ......... *H01R 13/518* (2013.01); *A61N 1/3754* (2013.01); *H01R 13/5202* (2013.01); *A61N 1/3605* (2013.01); *H01R 2201/12* (2013.01)

(58) Field of Classification Search
CPC .............. H01R 13/518; H01R 13/5202; H01R 2201/12; A61N 1/3754; A61N 1/3605
USPC ........................................................ 439/587
See application file for complete search history.

(56) References Cited

U.S. PATENT DOCUMENTS

| | | | |
|---|---|---|---|
| 4,140,361 A | 2/1979 | Sochor | |
| 4,275,944 A | 6/1981 | Sochor | |
| 4,764,132 A * | 8/1988 | Stutz, Jr. .............. | H01R 13/595 439/810 |
| 5,755,743 A * | 5/1998 | Volz ................... | H01R 13/5219 607/36 |
| 5,951,595 A * | 9/1999 | Moberg ................ | H01R 24/58 439/838 |
| 6,052,623 A | 4/2000 | Fenner et al. | |
| 6,662,035 B2 * | 12/2003 | Sochor ................... | H01R 24/58 607/116 |
| 6,984,145 B1 * | 1/2006 | Lim ..................... | H01R 13/595 439/660 |

(Continued)

*Primary Examiner* — Abdullah A Riyami
*Assistant Examiner* — Vladimir Imas
(74) *Attorney, Agent, or Firm* — Loza & Loza, LLP; David S. Sarisky

(57) ABSTRACT

A connector assembly includes a cover assembly and a feedthrough assembly that couples with the cover assembly. The cover assembly receives a connector end of a lead having lead contacts, and aligns the lead contacts with pockets or apertures of the cover assembly. The feedthrough assembly may include feedthrough contacts in the form of feedthrough pins at or above a surface of a feedthrough substrate, or conductive vias on the surface of the substrate. Electrical contacts configured as leaf spring contact assemblies, torsion spring contacts, or torsion spring contact assemblies are permanently attached to the feedthrough contacts. When the cover assembly and feedthrough assembly are coupled, contact tabs of the electrical contacts are positioned in the pockets or apertures of the cover assembly. Upon complete seating of the cover assembly and feedthrough assembly, the contact tabs are compressed into contact with the lead contacts.

16 Claims, 40 Drawing Sheets

(56) References Cited

U.S. PATENT DOCUMENTS

| | | | |
|---|---|---|---|
| 7,047,077 B2 | 5/2006 | Hansen et al. | |
| 7,083,474 B1 * | 8/2006 | Fleck | H01R 13/5804 439/669 |
| 7,210,968 B1 * | 5/2007 | Gister | H01R 4/44 439/668 |
| 7,425,142 B1 | 9/2008 | Putz | |
| 7,534,127 B2 * | 5/2009 | Parker | A61N 1/3752 439/425 |
| 7,553,193 B2 | 6/2009 | Kast et al. | |
| 7,690,953 B2 * | 4/2010 | Boyd | H01R 13/193 439/717 |
| 7,736,191 B1 * | 6/2010 | Sochor | H01R 24/58 607/116 |
| 7,794,256 B1 * | 9/2010 | Sochor | H01R 13/025 439/289 |
| 8,046,073 B1 | 10/2011 | Pianca | |
| 8,140,163 B1 * | 3/2012 | Daglow | H01R 13/193 607/36 |
| 8,162,684 B1 * | 4/2012 | Sochor | H01R 13/639 439/289 |
| 8,267,708 B1 * | 9/2012 | Sochor | H01R 24/58 439/289 |
| 8,515,555 B1 | 8/2013 | Jones | |
| 8,521,290 B2 | 8/2013 | North | |
| 8,690,609 B2 | 4/2014 | Poon et al. | |
| 8,694,103 B2 | 4/2014 | Barker | |
| 8,700,160 B2 | 4/2014 | Troosters et al. | |
| 8,874,206 B2 * | 10/2014 | Malinowski | A61N 1/3754 607/116 |
| 8,983,608 B2 | 3/2015 | Pianca | |
| 9,088,093 B2 * | 7/2015 | Reisinger | H01R 43/20 |
| 9,138,586 B2 | 9/2015 | Eiger | |
| 9,327,133 B2 | 5/2016 | Rutten et al. | |
| 9,362,660 B2 * | 6/2016 | Ries | H01R 24/58 |
| 9,401,562 B2 * | 7/2016 | Ries | A61N 1/3752 |
| 9,539,422 B2 | 1/2017 | Chen | |
| 9,907,964 B2 | 3/2018 | Deininger et al. | |
| 9,962,552 B2 | 5/2018 | Seeley et al. | |
| 10,063,020 B2 | 8/2018 | Kikuchi | |
| 10,071,253 B2 | 9/2018 | Janzig | |
| 10,249,415 B2 | 4/2019 | Seitz et al. | |
| 10,350,422 B2 * | 7/2019 | Sanders | A61N 1/3754 |
| RE47,624 E | 10/2019 | Tang et al. | |
| 10,608,354 B2 * | 3/2020 | Shah | H05K 5/006 |
| 10,965,082 B2 | 3/2021 | Jadwizak et al. | |
| 2006/0089682 A1 * | 4/2006 | Kronich | A61N 1/3754 607/32 |
| 2011/0270330 A1 * | 11/2011 | Janzig | B23K 26/21 156/60 |
| 2012/0245657 A1 * | 9/2012 | Lim | H01R 13/639 607/72 |
| 2012/0322317 A1 * | 12/2012 | Seeley | H01R 24/58 439/668 |
| 2014/0243942 A1 * | 8/2014 | Kast | A61N 1/3752 29/878 |
| 2015/0306402 A1 * | 10/2015 | Ries | H01R 24/58 439/271 |
| 2016/0268706 A1 * | 9/2016 | O'Rourke | A61N 1/3754 |
| 2017/0203105 A1 * | 7/2017 | Sontheimer | A61N 1/3956 |
| 2018/0178016 A1 * | 6/2018 | Frustaci | A61N 1/08 |
| 2018/0304084 A1 * | 10/2018 | Stevenson | H01G 4/30 |
| 2018/0353762 A1 * | 12/2018 | Sanders | A61N 1/3754 |
| 2022/0193423 A1 * | 6/2022 | Baqar | H01R 13/5224 |

* cited by examiner

SECTION A-A (FIG. 1)

SECTION B-B (FIG. 1)

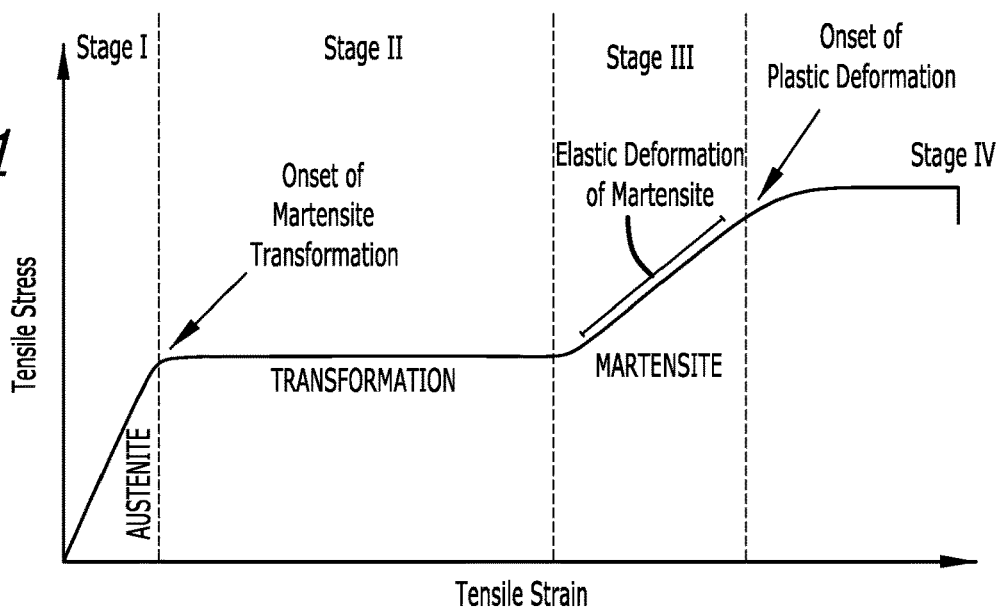
FIG. 11
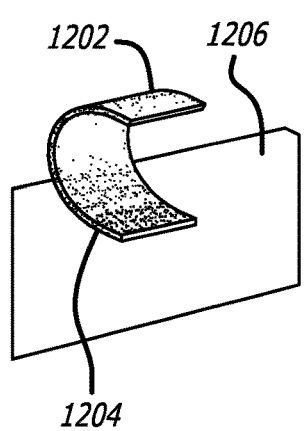
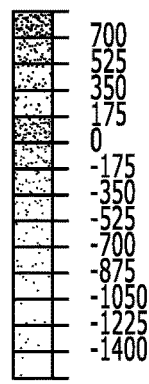
FIG. 12
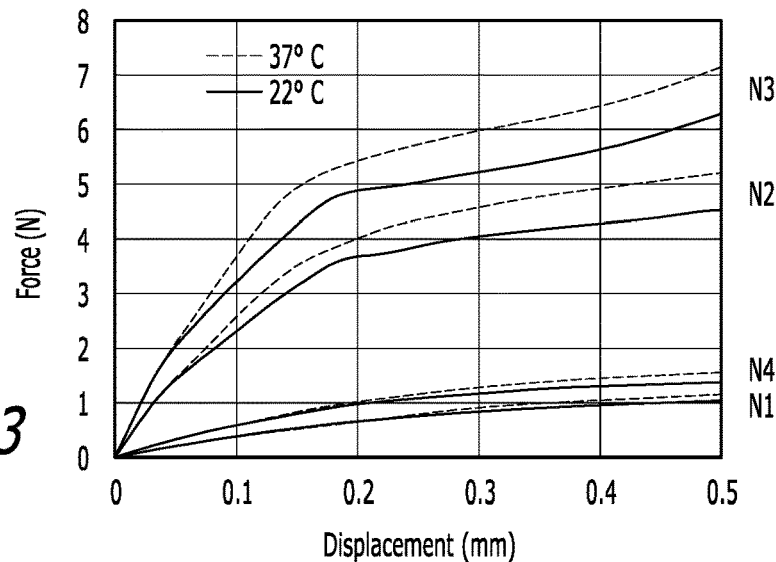
FIG. 13

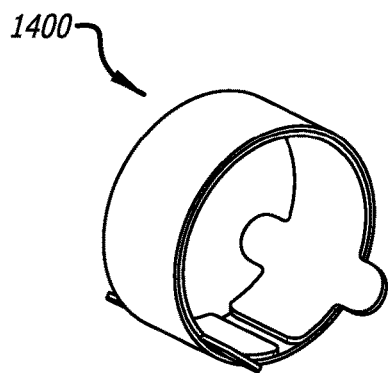
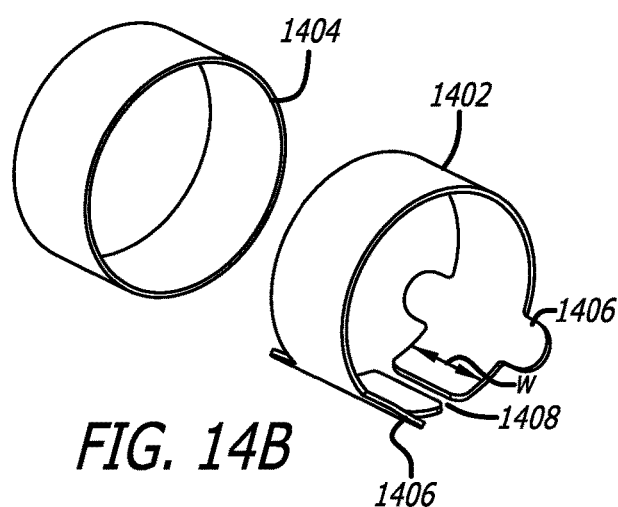
FIG. 14A  FIG. 14B
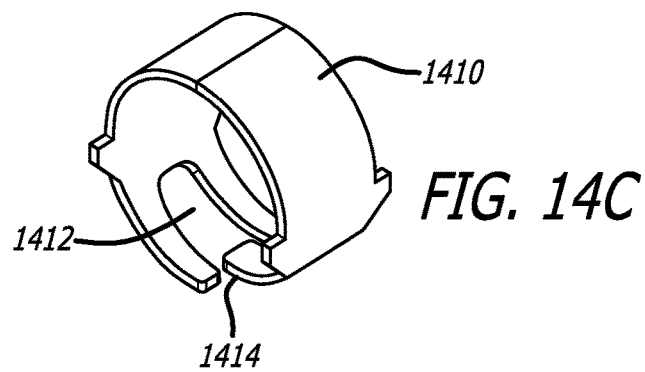
FIG. 14C
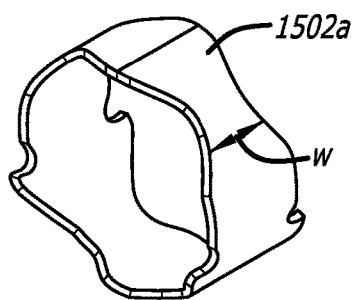 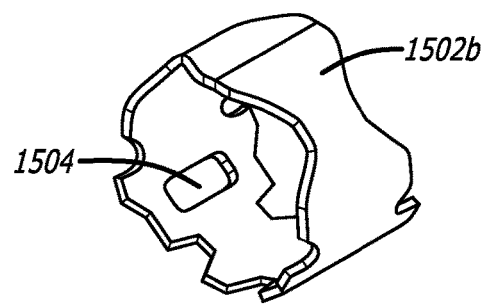
FIG. 15A  FIG. 15B

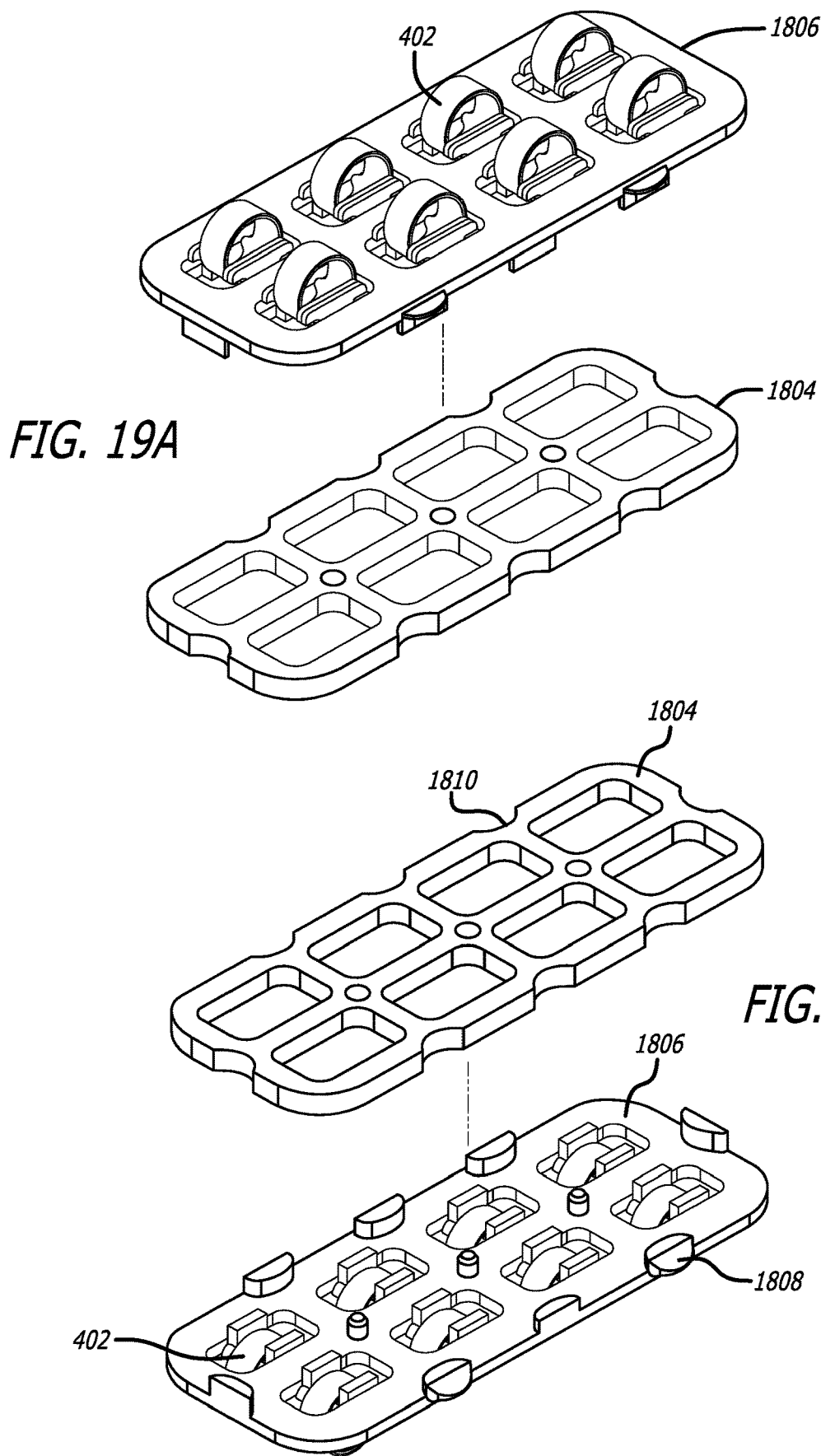

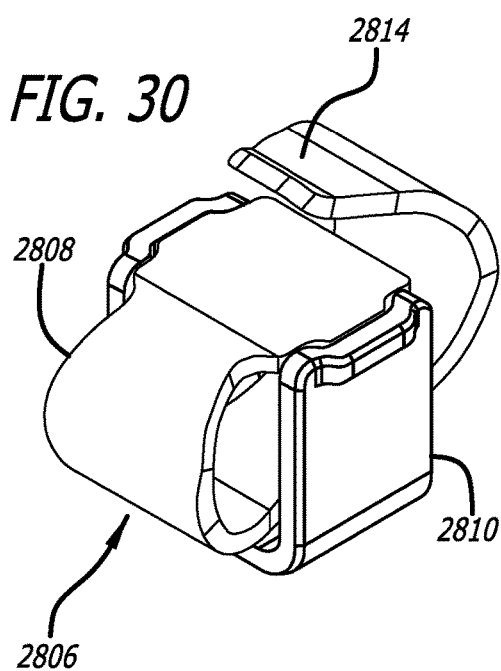
FIG. 30
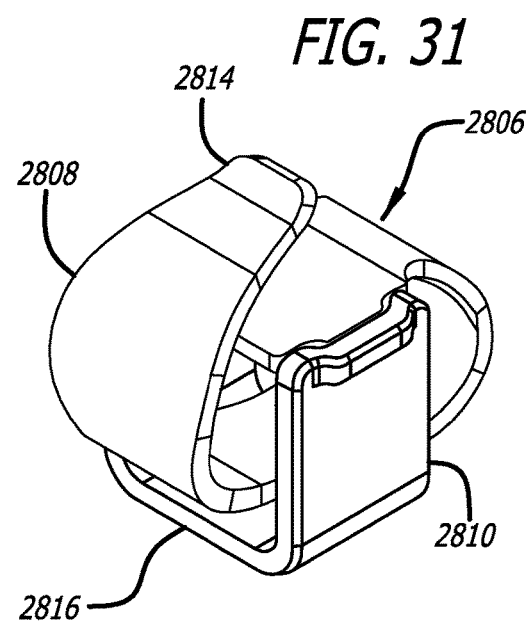
FIG. 31
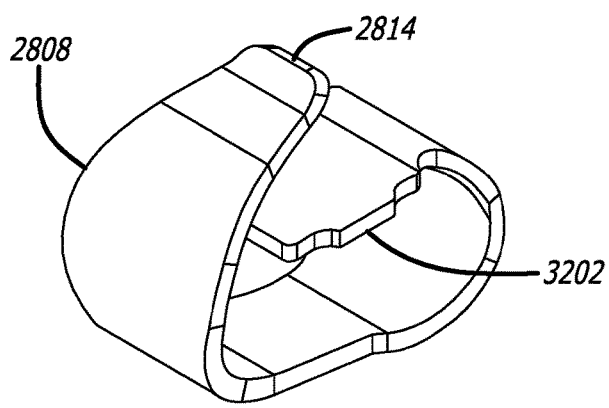
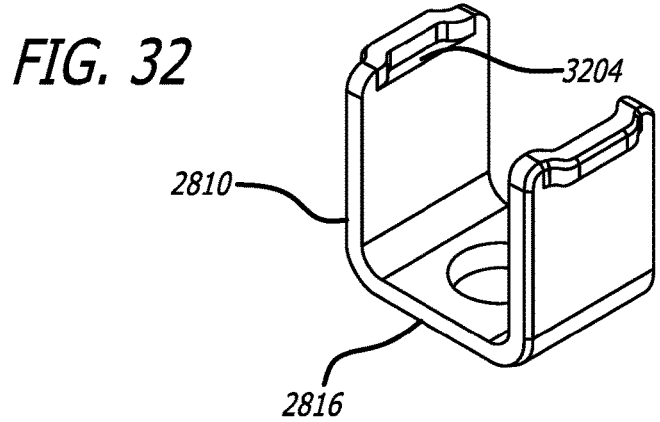
FIG. 32

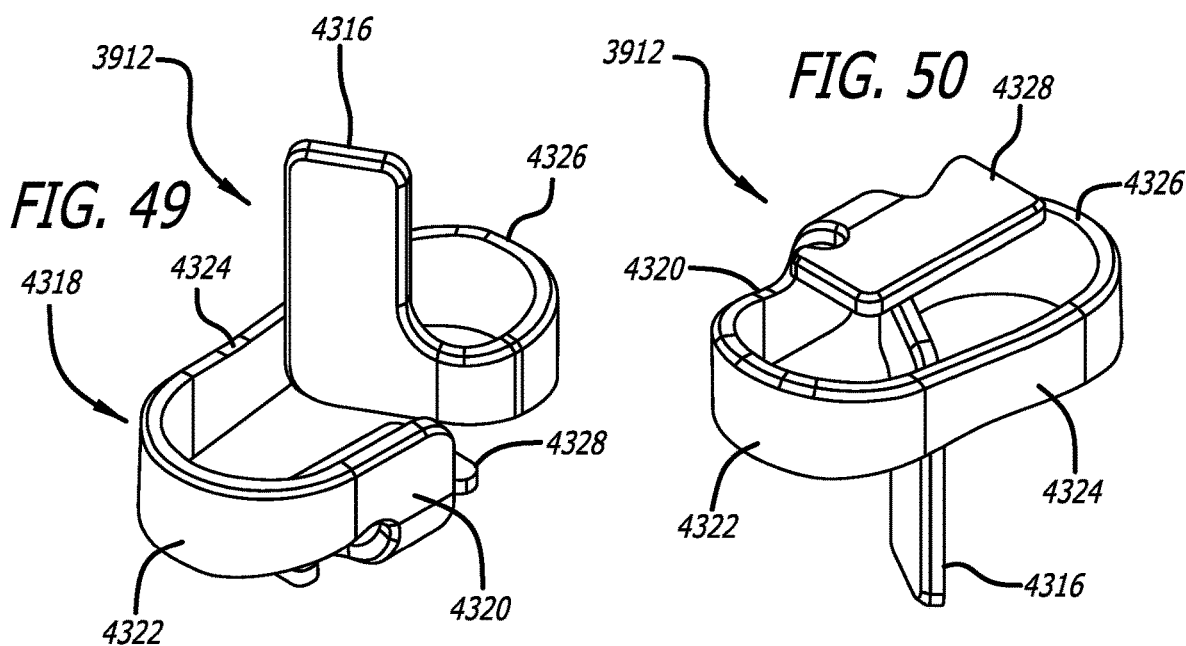
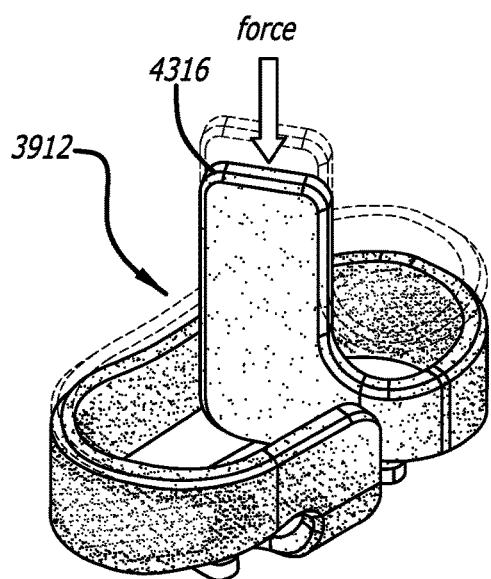
FIG. 51
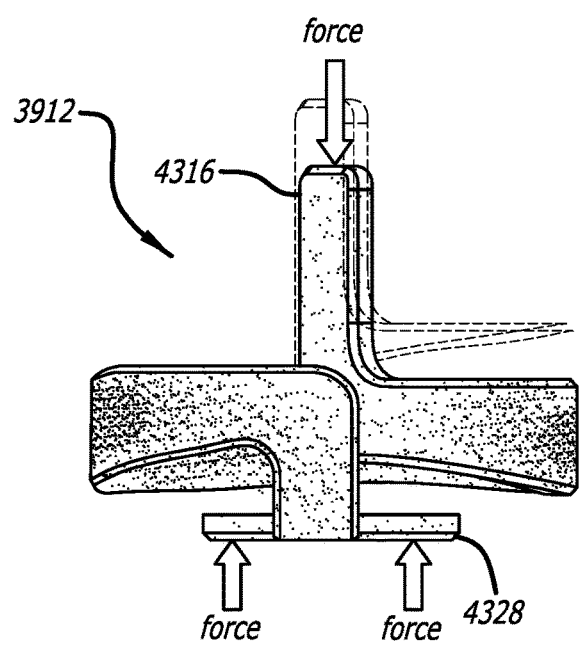
FIG. 52

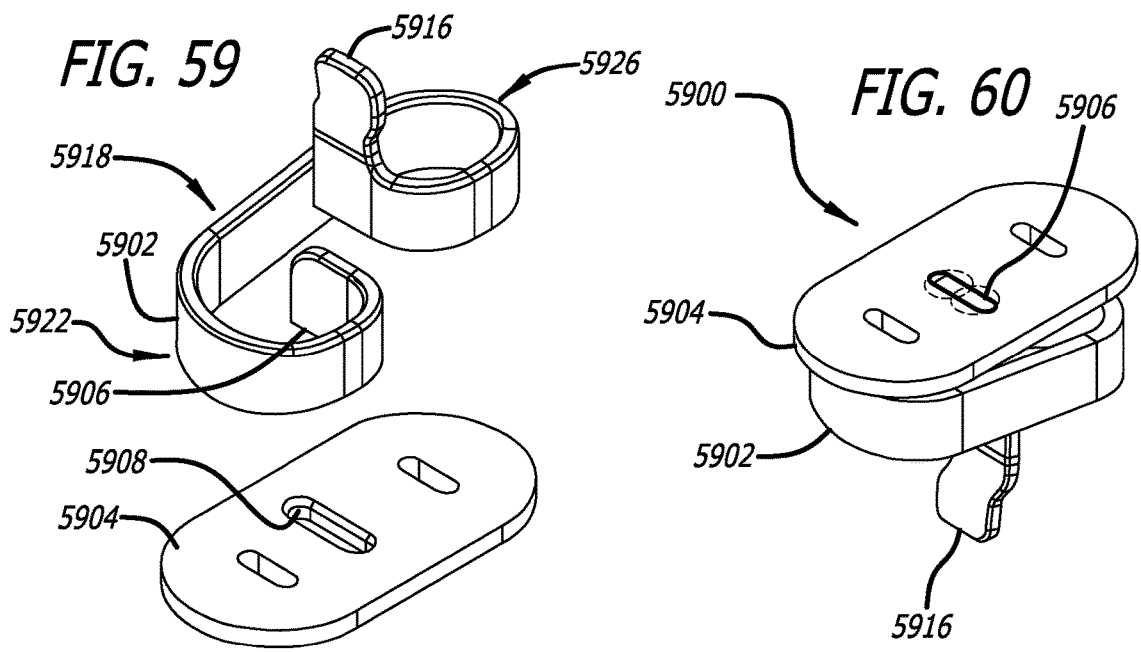
FIG. 59
FIG. 60
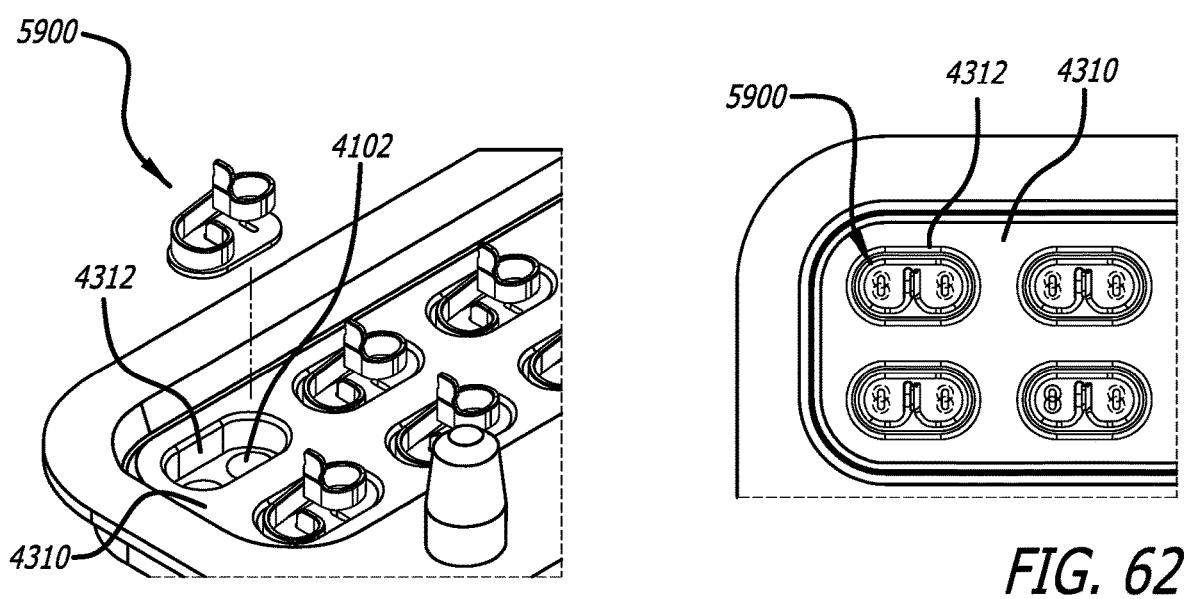
FIG. 61
FIG. 62

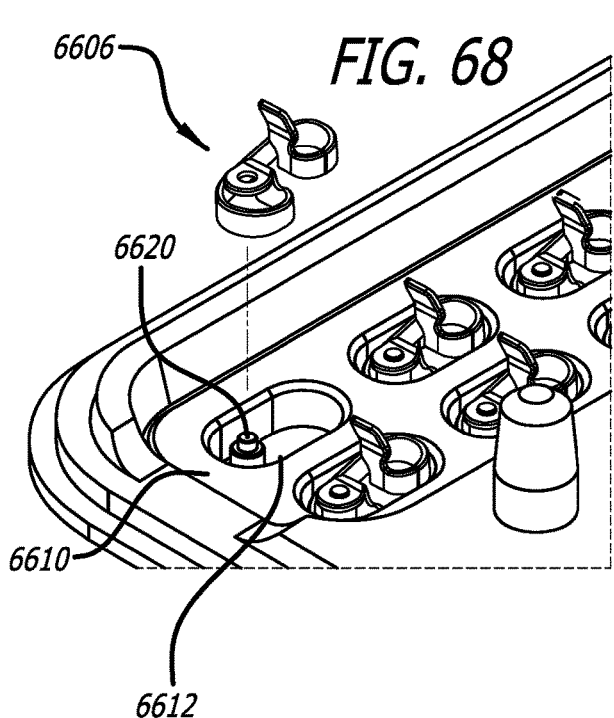
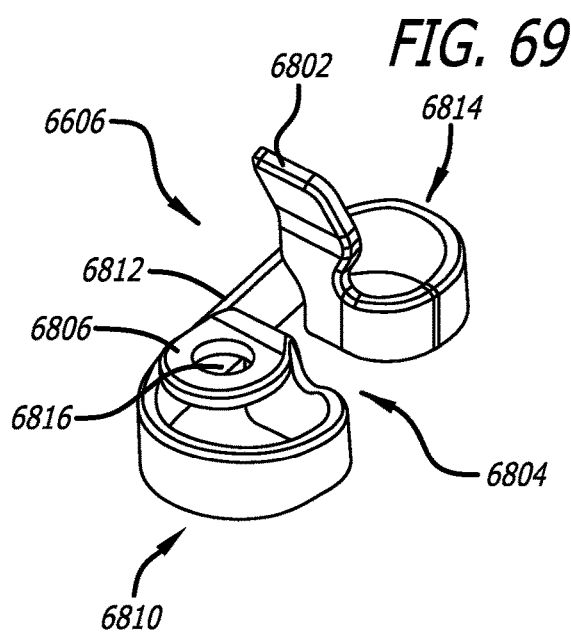
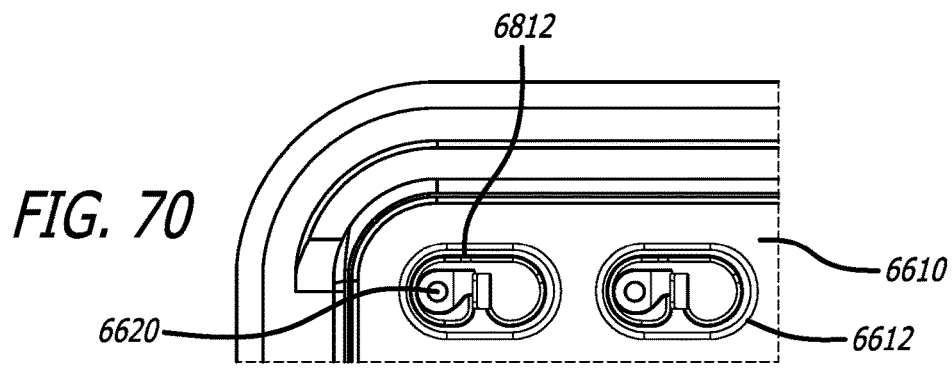
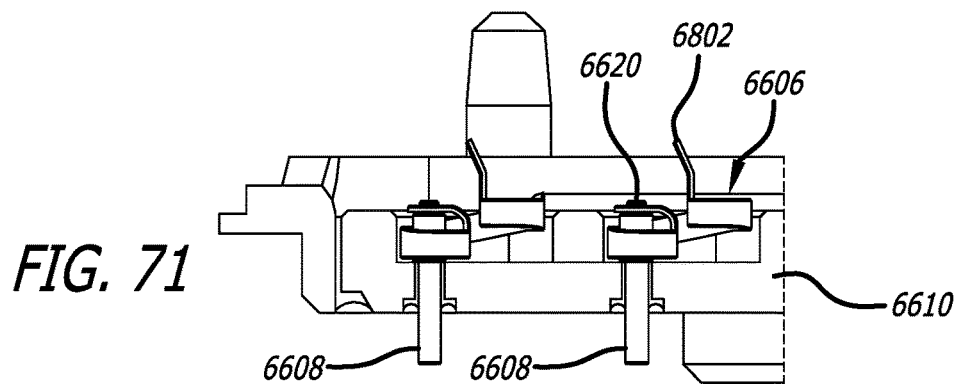

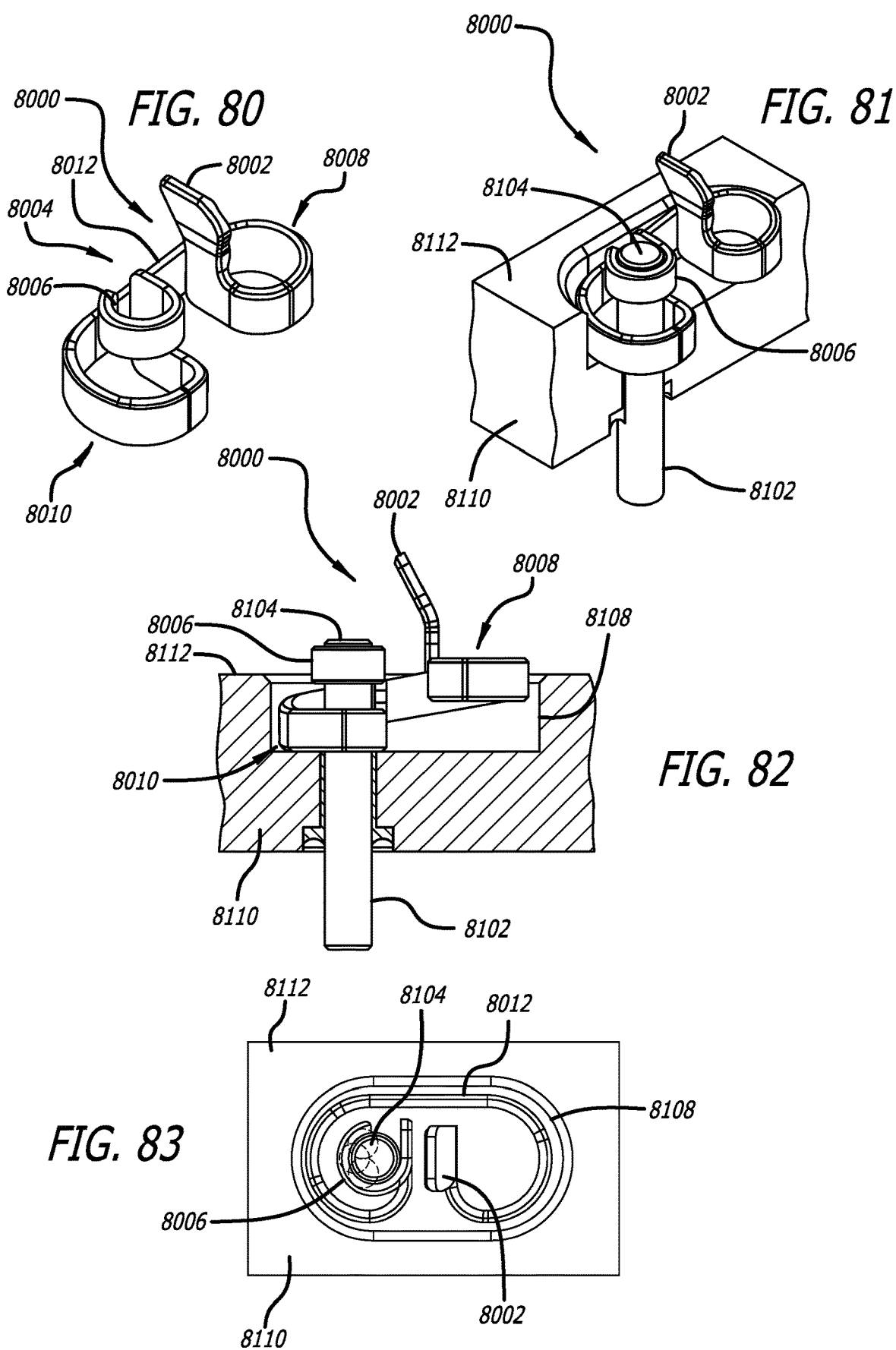

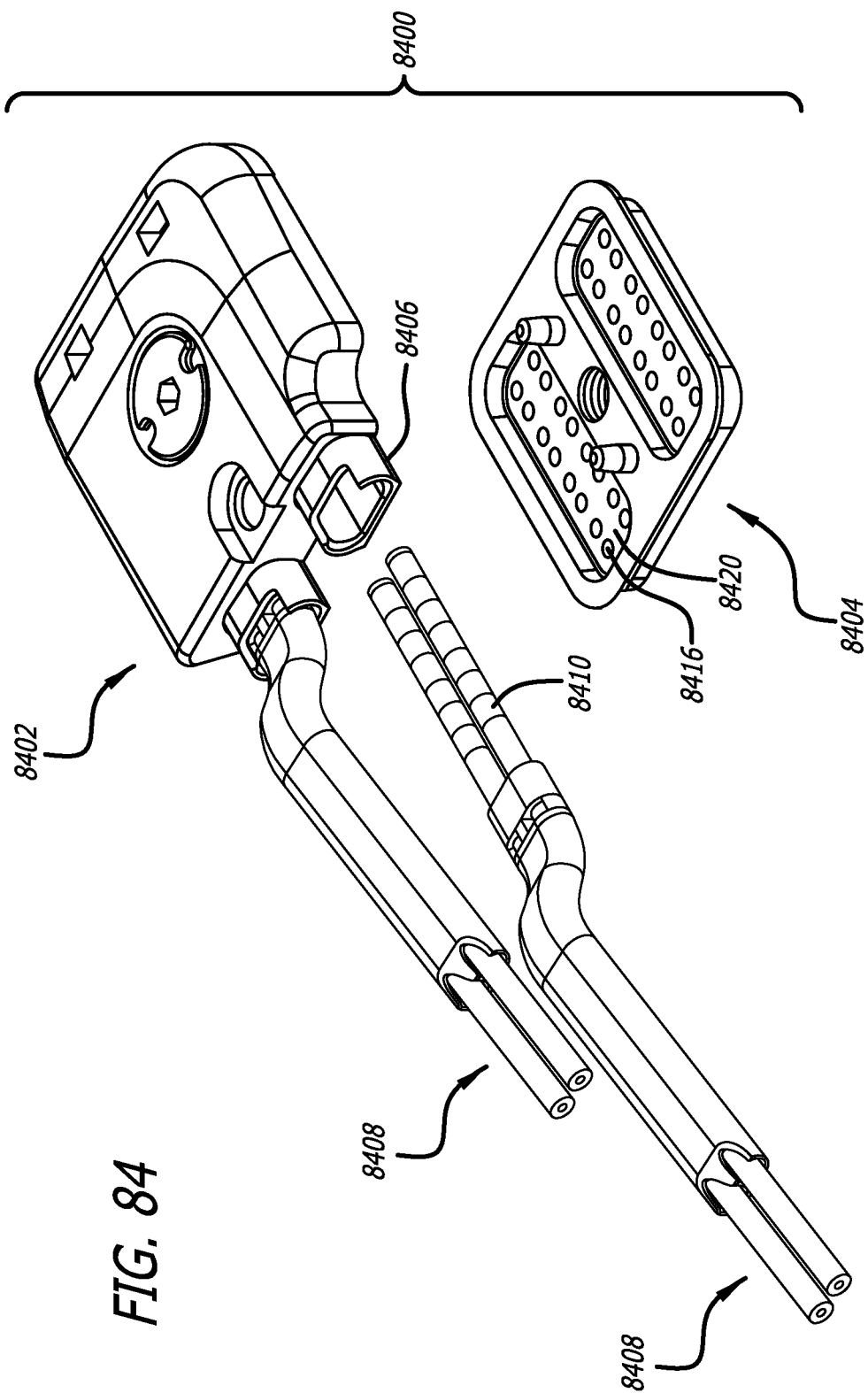

CONNECTOR ASSEMBLY FOR ACTIVE IMPLANTABLE MEDICAL DEVICE

TECHNICAL FIELD

The present disclosure relates generally to active implantable medical devices, and more particularly, to a connector assembly for active implantable medical devices that provides electrical connection between electronics within a housing of the device and electrical leads coupled to the device.

BACKGROUND

Known connector assemblies for implantable medical devices utilize stamped compressive leaf contacts, e.g., see U.S. Pat. No. 6,662,035. These connector assemblies include a clamping cover with one or more elastomeric seals configured to receive leads, and a feedthrough assembly that includes compressive leaf contacts, and to which the clamping cover connects. The compressive leaf contacts are attached to feedthrough pins of the feedthrough assembly by laser welding. A lead is received in a separate elastomeric seal of the clamping assembly. The lead contacts engage the compressive leaf contacts via apertures in the seal when the clamping cover is fully seated with the feedthrough assembly, or in other words, when the connector assembly is pressurized.

SUMMARY

A connector assembly of an implantable medical device includes a cover assembly and a feedthrough assembly configured to couple with the cover assembly. The cover assembly is configured to receive a connector end of a lead having lead contacts, and to align the lead contacts with pockets or apertures of the cover assembly. The feedthrough assembly may include feedthrough contacts in the form of feedthrough pins at or above a surface of a feedthrough substrate, or conductive vias on the surface of the substrate. Electrical contacts configured as leaf spring contact assemblies, torsion spring contacts, or torsion spring contact assemblies are permanently attached to the feedthrough contacts through an attachment feature of the contacts. When the cover assembly and feedthrough assembly are coupled, contact engagement features of the electrical contacts are positioned in the pockets or apertures of the cover assembly. Upon complete seating of the cover assembly and feedthrough assembly, the contact engagement features are compressed into contact with the lead contacts.

A connector assembly of an implantable medical device includes a cover assembly and a feedthrough assembly configured to couple with the cover assembly. The cover assembly is configured to receive a connector end of a lead having lead contacts, and to align the lead contacts with pockets or apertures of the cover assembly. The feedthrough assembly may include feedthrough contacts in the form of feedthrough pins at or above a surface of a feedthrough substrate, or conductive vias on the surface of the substrate. Electrical contacts configured as contact ring assemblies or leaf spring contacts are retained by, but not permanently attached to, one of the feedthrough assembly or the cover assembly. When the cover assembly and feedthrough assembly are coupled, first surfaces of the electrical contacts face the feedthrough contacts and second surfaces of the contacts are positioned in the pockets or apertures of the cover assembly. Upon complete seating of the cover assembly and feedthrough assembly, the first surfaces and second surfaces of the electrical contacts are respectively compressed into contact with the feedthrough contacts and the lead contacts.

It is understood that other aspects of apparatuses and methods will become readily apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of apparatuses will now be presented in the detailed description by way of example, and not by way of limitation, with reference to the accompanying drawings, wherein:

FIG. 11 is a graph corresponding to the theoretical stress-strain curve of super-elastic nitinol.

FIG. 12 is a graphical representation of the levels of stress of a contact ring assembly under radial compression.

FIG. 13 is a graph representing force-displacement behavior of different geometries during radial compression.

FIGS. 14A and 14B are illustrations of a contact ring assembly including a contact ring and a backing ring.

FIGS. 14C-17B are illustrations of different embodiments of backing rings.

FIGS. 18A-19B are illustrations of different embodiments of electrical contact interposer assemblies.

FIGS. 30 and 31 are different perspective illustrations of the leaf spring contact assembly of FIG. 28 including a compressive contact and a U-shaped mount.

FIG. 32 is a disassembled view of a leaf spring contact assembly of FIG. 31.

FIG. 49 is an isometric view of the torsion spring contact of FIG. 41 in a free state.

FIG. 50 is an upside-down view of the torsion spring contact of FIG. 49.

FIG. 51 is an isometric view of the torsion spring contact of FIG. 49 with contact force applied, showing contact deflection and resulting Von Mises stress.

FIG. 52 is a side view of the torsion spring contact of FIG. 49 with contact force applied, showing contact deflection and resulting Von Mises stress.

FIG. 59 is an exploded view of another contact configured as a torsion spring contact assembly that includes a torsion spring contact and a weld plate.

FIG. 60 is an upside-down perspective view of the torsion spring contact assembly of FIG. 59.

FIG. 61 is a partial perspective view of a feedthrough assembly with the torsion spring contact assembly of FIG. 59 raised above a dielectric substrate of the feedthrough assembly.

FIG. 62 is a partial top view of a feedthrough assembly showing the torsion spring contact assembly of FIG. 59 occupying a counterbore of the dielectric substrate.

FIG. 68 is a partial perspective view of a feedthrough assembly showing a torsion spring contact of FIGS. 66 and 67 at least partially raised above a counterbore of a dielectric substrate of the feedthrough assembly.

FIG. 69 is enlarged view of the torsion spring contact of FIG. 68.

FIG. 70 is a partial top view of the feedthrough assembly of FIG. 68, showing torsion spring contacts coupled to feedthrough pins, and with increased clearance between a free side of the contacts and an inside wall of the counterbore.

FIG. 71 is a partial cross-sectional view of the feedthrough assembly of FIG. 68 showing torsion spring contacts coupled to feedthrough pins, and with increased clearance between a free side of the contacts and an inside wall of the counterbore.

FIGS. 80-83 are illustrations of another contact configured as a torsion spring contact configured to occupy a counterbore in a dielectric substrate and to attach to a feedthrough pin that extends above the counterbore.

FIGS. 84 and 85 are illustrations of a connector assembly that includes a cover assembly and a feedthrough assembly, wherein the cover assembly is decoupled from the feedthrough assembly and the feedthrough assembly includes contacts configured as leaf spring contacts that are retained by the cover assembly.

DETAILED DESCRIPTION

Figure 1:
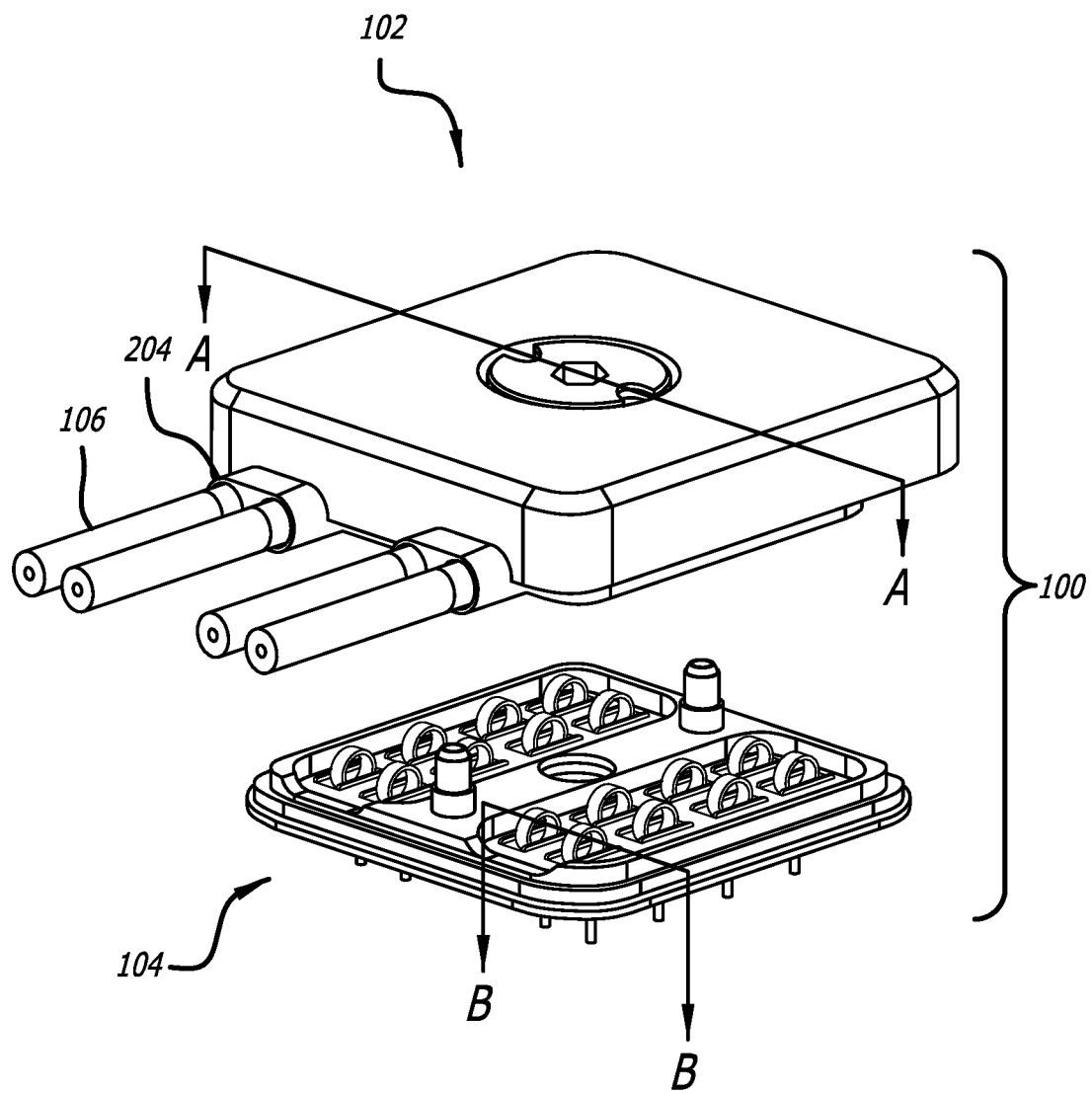
FIG. 1 is an illustration of a connector assembly that includes a cover assembly and a feedthrough assembly, wherein the cover assembly is decoupled from the feedthrough assembly and the feedthrough assembly includes separable or detached, i.e., interposed, contacts configured as contact ring assemblies.

Disclosed herein are various types of connector assemblies for implantable medical devices. The connector assemblies disclosed provide means of establishing electrical interconnection between electronics within a housing of an active implantable medical device and electrical leads coupled to the device. The connector assemblies include a cover assembly having ports, each for receiving a connector end of a lead, and a feedthrough assembly having feedthrough contacts. The cover assembly is configured to couple to the feedthrough assembly and establish electrical connection between lead contacts at the connector ends of the received leads and the feedthrough contacts. The electrical connection is provided in part by contacts of the connector assembly that are located between the lead contacts and the feedthrough contacts. In some configurations, the contacts are associated with the feedthrough assembly. In other configurations, the contacts are associated with the cover assembly.

In some embodiments the connector assemblies disclosed herein accommodate four leads in about the same amount of space as a conventional connector assembly that accommodates only two leads. Accordingly, the connector assemblies can be designed into a modified implantable medical device without having to expand the size of the device. The connector assemblies may include four lines of contacts, where each line of contacts is arranged to couple with a corresponding line of lead contacts at the connector end of a lead. In order to double the contact density, the disclosed connector assemblies use smaller compressive contacts with ring configurations, leaf spring configurations, or torsion spring configurations, which assure adequate contact deflection capability in a smaller contact footprint. The contacts are disposed in-line with the lead to enable using two dual-lumen seals, each seal receiving two leads with lead-to-lead spacing of approximately 2 mm.

The contacts may be associated with the feedthrough assembly and may be detached, ring contacts or leaf spring contacts retained in a support structure. In other configurations disclosed herein, the contacts may be leaf spring contacts or torsion spring contacts that are attached to feedthrough contacts. In other embodiments the contacts may be associated with the cover assembly. For example, the contacts may be detached, leaf spring contacts retained in an elastomeric seal of the cover assembly.

I. Contacts Associated with Feedthrough Assembly

Connector assembly contacts may be associated with the feedthrough assembly in either of two ways. In one configuration, the contacts are securely retained in a contact retainer of the feedthrough assembly through respective mechanical features of the contacts and the contact retainer in a way that prevents movement of the contacts within the contact retainer, even when a cover assembly is removed from the feedthrough assembly. Upon coupling of the cover assembly to the feedthrough assembly, the contacts are further retained by a contact force between two conductive elements that compresses the contacts. The contacts in this configuration may be generally described herein as being separable or detached because the contacts are not welded or bonded within the contact retainer, but instead are retained in a way that allows for compression or pressure connection between the contacts, the lead contacts, and the feedthrough contacts when a cover assembly is coupled to the feedthrough assembly. These detached, separable contacts may be referred to herein as "interposer" contacts. In another configuration, the contacts are securely retained in a feedthrough assembly through bonding. For example, the contacts may be covalently bonded to the feedthrough contacts of the feedthrough assembly by a laser welding process. The contacts in this configuration may be generally described herein as being inseparable or attached.

A. Feedthrough Assembly with Detached Contact Ring Assemblies

With reference to FIGS. 1-19B, a connector assembly 100 of an implantable medical device includes a cover assembly 102 and a feedthrough assembly 104 configured to couple with the cover assembly. The cover assembly 102 is configured to receive a connector end of a lead 106 having lead contacts 1002, and to align the lead contacts with pockets or apertures 210 of the cover assembly. The feedthrough assembly 104 may include feedthrough contacts 314 in the form of feedthrough pins 312 at or above a surface of a feedthrough substrate 310, or conductive vias on the surface of the substrate. Electrical contacts 402 configured as contact ring assemblies are retained by, but not permanently attached to, the feedthrough assembly 104. When the cover assembly 102 and feedthrough assembly 104 are coupled, first surfaces 1004 of the electrical contacts 402 face the feedthrough contacts 314 and second surfaces 1006 of the contacts are positioned in the pockets or apertures 210 of the cover assembly. With reference to FIG. 10B, upon complete seating of the cover assembly 102 and the feedthrough assembly 104, the first surfaces 1004 and second surfaces 1006 of the electrical contacts 402 are respectively compressed into contact with the feedthrough contacts 314 and the lead contacts 1002.

Figure 2A:
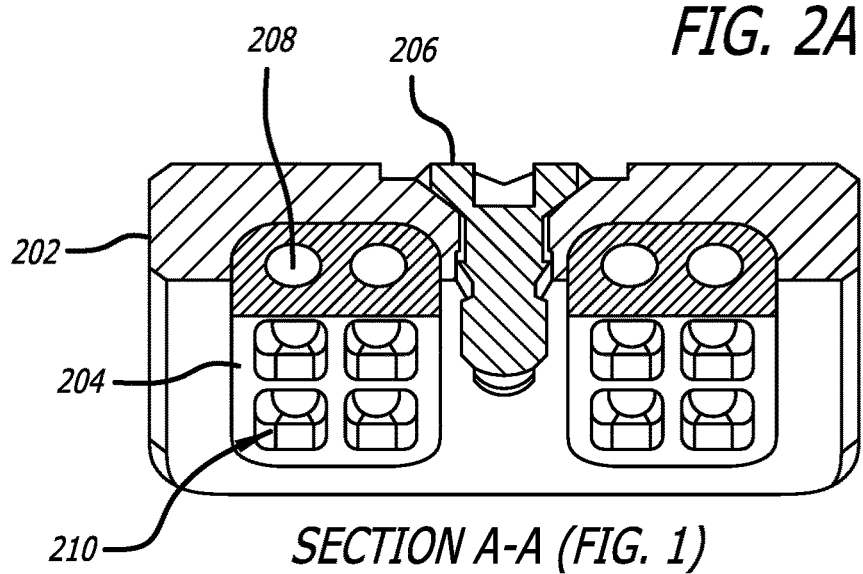
FIG. 2A is a cross-section view of the cover assembly of FIG. 1 along line A-A and showing the cover assembly from underneath.
Figure 2B:
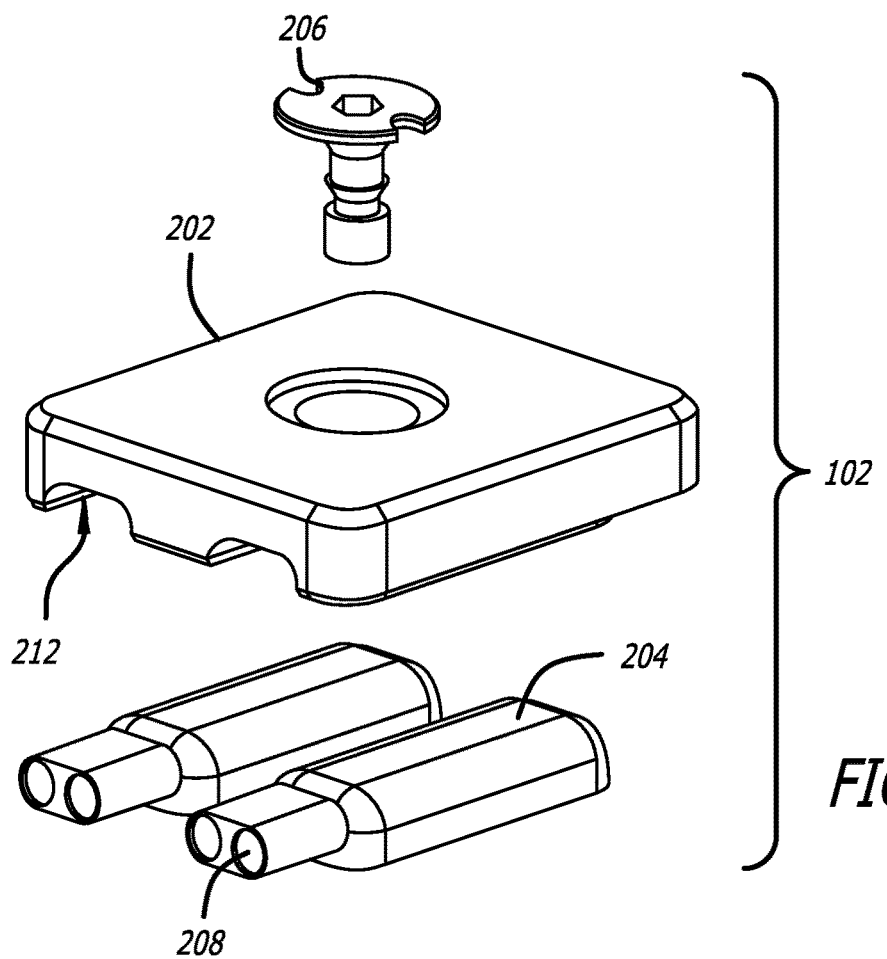
FIG. 2B is an exploded illustration of the cover assembly of FIG. 1.

With reference to FIGS. 2A and 2B, the cover assembly 102 includes a cover 202, a pair of upper seals 204, and a screw 206. The upper seals 204 may be made of silicone and are sized to fit at least partially within recesses 212 formed in the bottom of the cover 202. The upper seals 204 may be bonded into the recesses 212 with a silicone adhesive. Each upper seal 204 includes two lead ports 208, each configured to receive a proximal end, or connector end of a lead. The proximal end of the lead has a number of lead contacts. Apertures 210 in the upper seals 204 allow access between the lead contacts of a lead positioned in a lead port 208 and feedthrough contacts of a feedthrough assembly 104. The screw 206 is retained in the cover 202 and is configured to secure to a corresponding hole in the feedthrough assembly.

Figure 3:
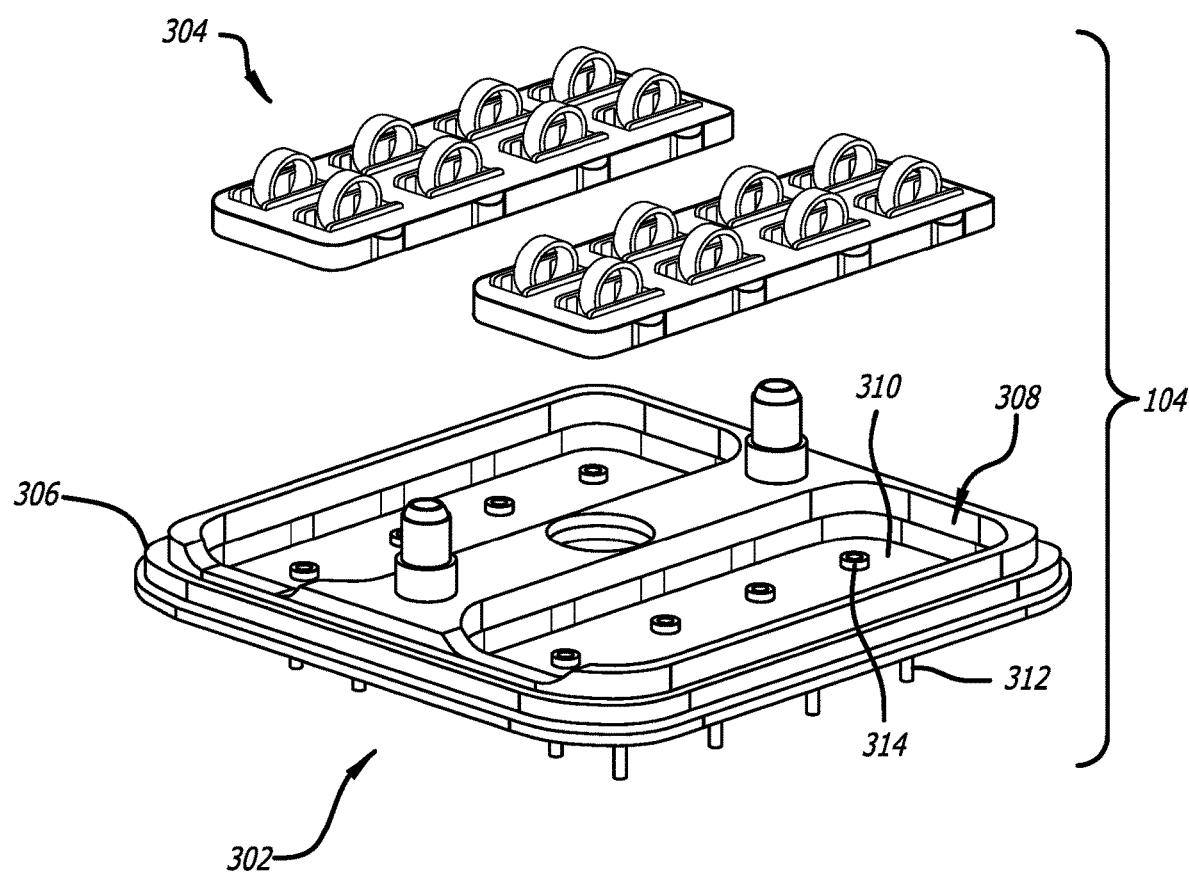
FIG. 3 is an exploded illustration of the feedthrough assembly of FIG. 1 including a pair of electrical contact interposer assemblies and a feedthrough subassembly.

With reference to FIG. 3, the feedthrough assembly 104 includes a feedthrough subassembly 302 and an electrical contact interposer assembly 304. The feedthrough subassembly 302 includes a feedthrough ferrule 306 with a pair of rectangular recesses 308, each with a feedthrough substrate 310 fitted therein. A number of feedthrough pins 312 pass through the feedthrough substrate 310 providing an electrical conduction path between opposite sides of the feedthrough ferrule 306. Each of the feedthrough pins 312 has a head 314 on the recess side of the feedthrough ferrule 306. The head 314 may be referred to as a feedthrough contact.

Figure 4:
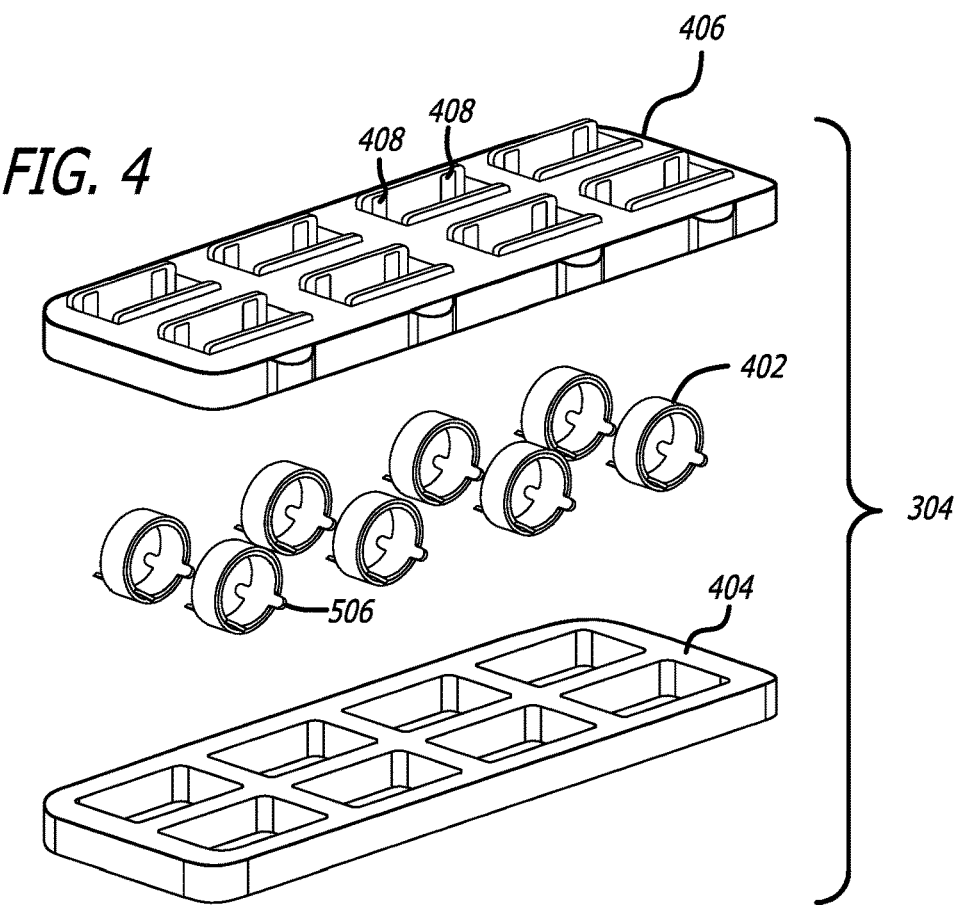
FIG. 4 is an exploded illustration of an electrical contact interposer assembly of FIG. 3 including contact ring assemblies, a contact retainer, and a lower seal.

With reference to FIG. 4, the electrical contact interposer assembly 304 includes a number of electrical contacts 402 configured as contact ring assemblies, a lower seal 404, and a contact retainer 406. The contact ring assemblies 402 and contact retainer 406 are configured so that the contacts are retained by the contact retainer. To this end, in one configuration, the contact ring assemblies 402 include tabs 506 configured to be positioned within retention slots 408 of the contact retainer 406 and to interfere with the contact retainer in a way that prevents movement of the contacts relative to the contact retainer. In one configuration, the contact retainer 406 is an injection molded component made of Polyetheretherketone (PEEK). The contact retainer 406 may also be made of other materials such as liquid crystal polymer (LCP). The lower seal 404 is a molded component made of a silicone rubber which fits into a mating recess in the contact retainer 406.

Figure 5:
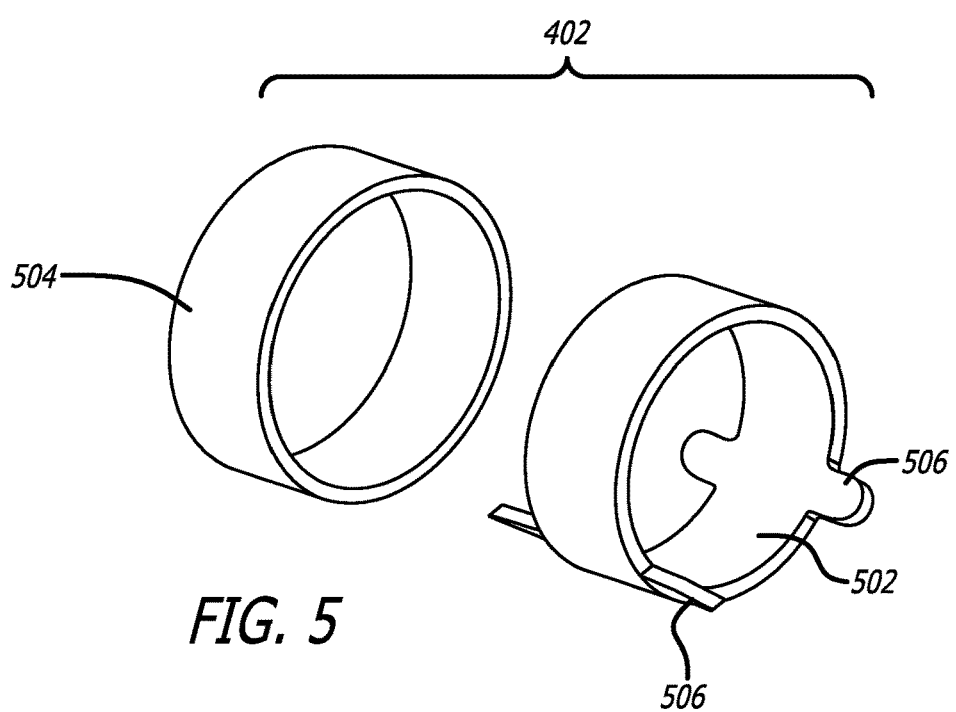
FIG. 5 is an exploded illustration of a contact ring assembly of FIG. 4.

With reference to FIG. 5, in one configuration the contact ring assemblies 402 are configured as contact ring assemblies, each of which includes a contiguous backing ring 502 and a contiguous contact ring 504. The backing ring 502 includes a pair of retention tabs 506. The backing ring 502 may be made of nitinol, which is a super-elastic material that provides sufficient contact force and elastic range when squeezed between the feedthrough pin 312 and a lead contact. The force necessary to establish an electrical contact may be greater than 50 grams. The necessary elastic range of the backing ring 502 is dependent upon the design of the lower seal 404 and the physical space to accommodate the backing ring.

In one embodiment, the outside diameter of the backing ring 502 is approximately 1.3 mm. The outside diameter of the backing ring 502 may range from 1-2 mm depending on the required range of elastic deflection and available physical space to accommodate the ring. The wall thickness of the backing ring 502 may vary from 0.02-0.10 mm. The wall thickness has a significant effect on contact force and elastic range of the backing ring 502. The width of the backing ring 502 may vary from 0.5-2 mm depending on the required range of contact force and available physical space to accommodate the ring. In one specific configuration, the backing ring 502 a wall thickness of 0.04 mm, an outside diameter of 1.3 mm and width of 0.7 mm. The backing ring 502 includes tabs 506 that facilitate retaining the rings in contact retainer 406.

In some embodiments, the contact ring 504 is made of a 90-10 platinum-iridium alloy. The contact ring 504 is sized to fit over the backing ring 502 and provides electrical contact between the feedthrough pins 312 and the lead contacts. The contact ring 504 is approximately equal in width to the backing ring 502. The inside diameter of the of the contact ring 504 is approximately equal to or slightly larger (0.002-0.01 mm) than the outside diameter of the backing ring 502. A slip fit between the backing ring 502 and the contact ring 504 facilitates assembly. An interference fit between the two rings 502, 504 may be suitable given alternate embodiments of the contact ring assembly 402. The wall thickness of the contact ring 504 is approximately 0.025 mm. Due to the ductal property of the contact ring 504, the contact ring does not slip axially over the backing ring 502, after the assembly is compressed radially.

Figure 6:
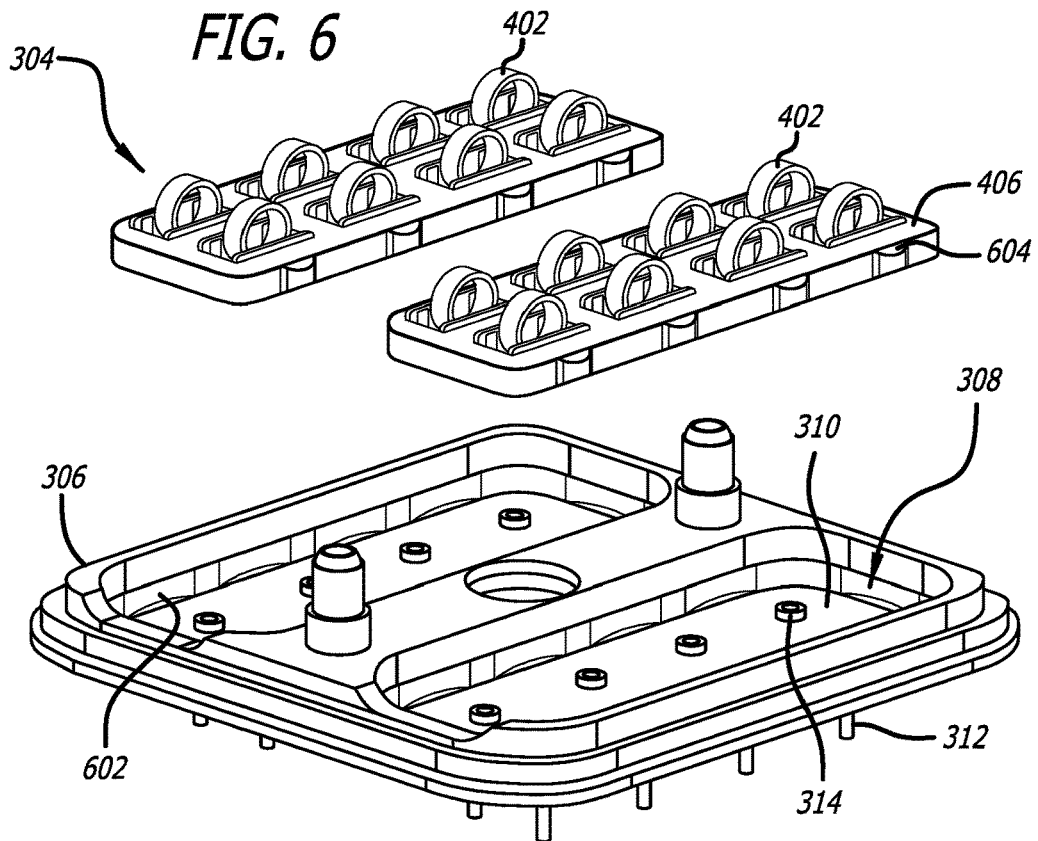
FIG. 6 is an enlarged version of the illustration of FIG. 3.
Figure 7:
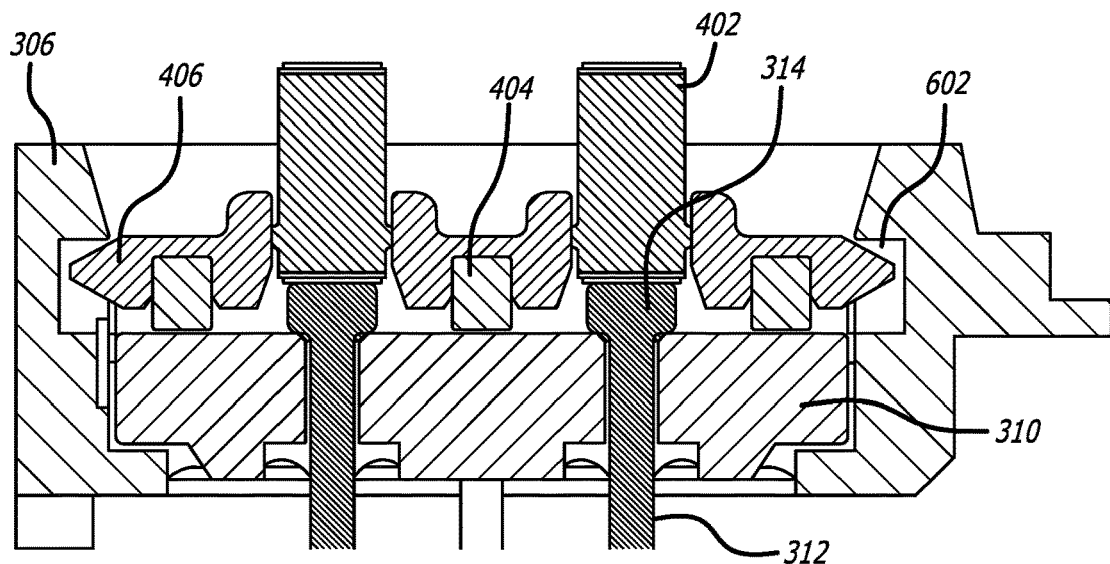
FIG. 7 is a cross-section view of a portion of the connector assembly of FIG. 1 along line B-B.

With reference to FIGS. 6 and 7, undercuts 602 are machined into the feedthrough ferrule 306. These undercuts 602 mate with tabs 604 on the contact retainer 406. The mating features serve to retain the electrical contact interposer assemblies 304 in the feedthrough subassembly 302. The tabs 604 provide a snap-in feature during assembly that retains the electrical contact interposer assemblies 304 in the feedthrough subassembly 302. In one embodiment, the centers of the tabs 604 of the contact retainer 406 are aligned parallel with the center axis of the contact ring assemblies 402.

Figure 8:
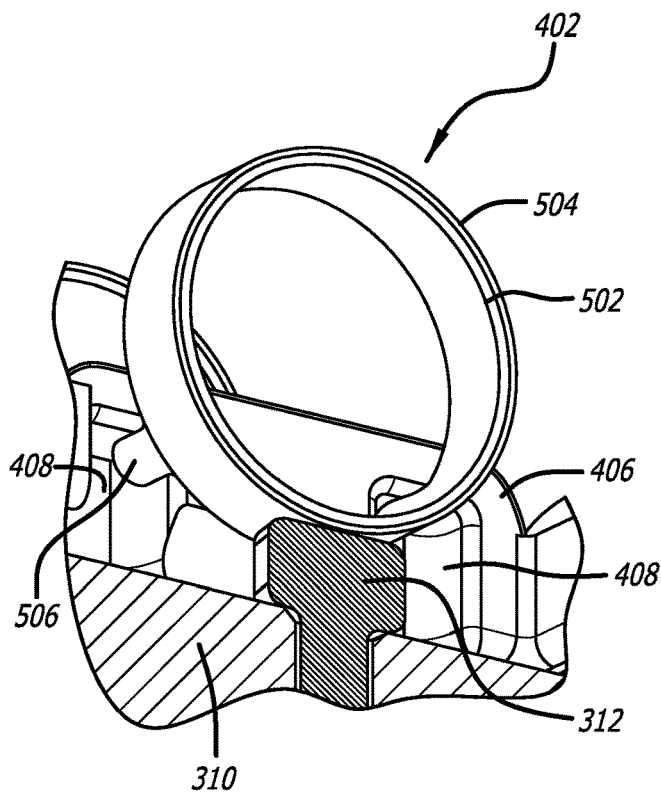
FIG. 8 is cross-section view of a portion of an electrical contact interposer assembly showing a contact ring assembly retained by a contact retainer.
Figure 9A:
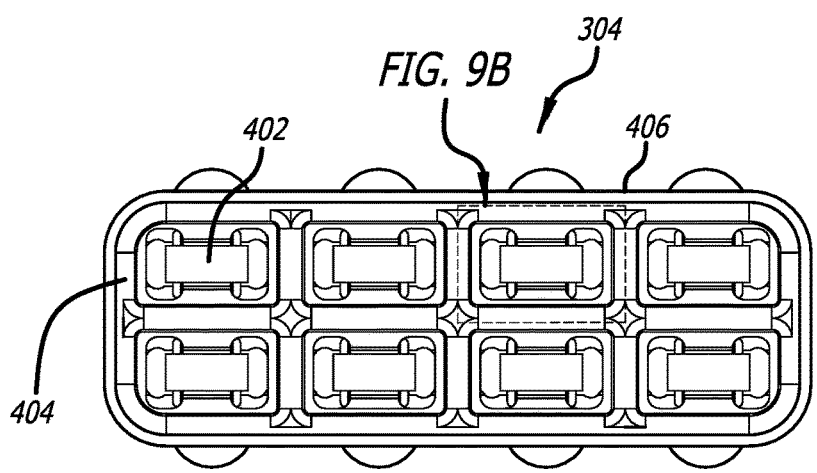
FIGS. 9A and 9B are plan views of an electrical contact interposer assembly.
Figure 9B:
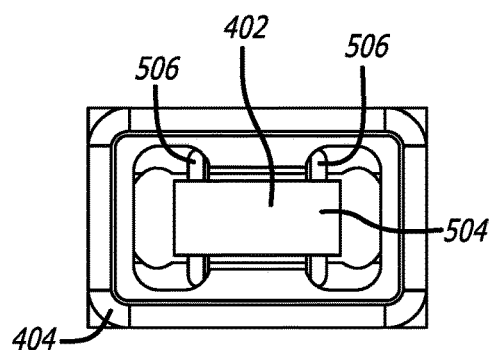

With reference to FIGS. 8, 9A, and 9B, the contact ring assemblies 402 are retained within the contact retainer 406 by an interference fit between the retention tabs 506 of the backing ring 502 and retention slots 408 in the contact retainer 406. To this end, the distance between retention tabs 506 on the same side of the contact ring assembly 402 is slightly less than the width of the distance between retention slots 408 in the contact retainer 406, resulting in an interference fit between the assembled components. The interference fit between the retention tabs 506 of the backing ring 502 and the retention slots 408 of the contact retainer 406 has the effect of locking the contact ring assembly 402 onto the contact retainer 406, which aids the assembly process and adds stability of the contacts within the contact retainer.

Figure 10A:
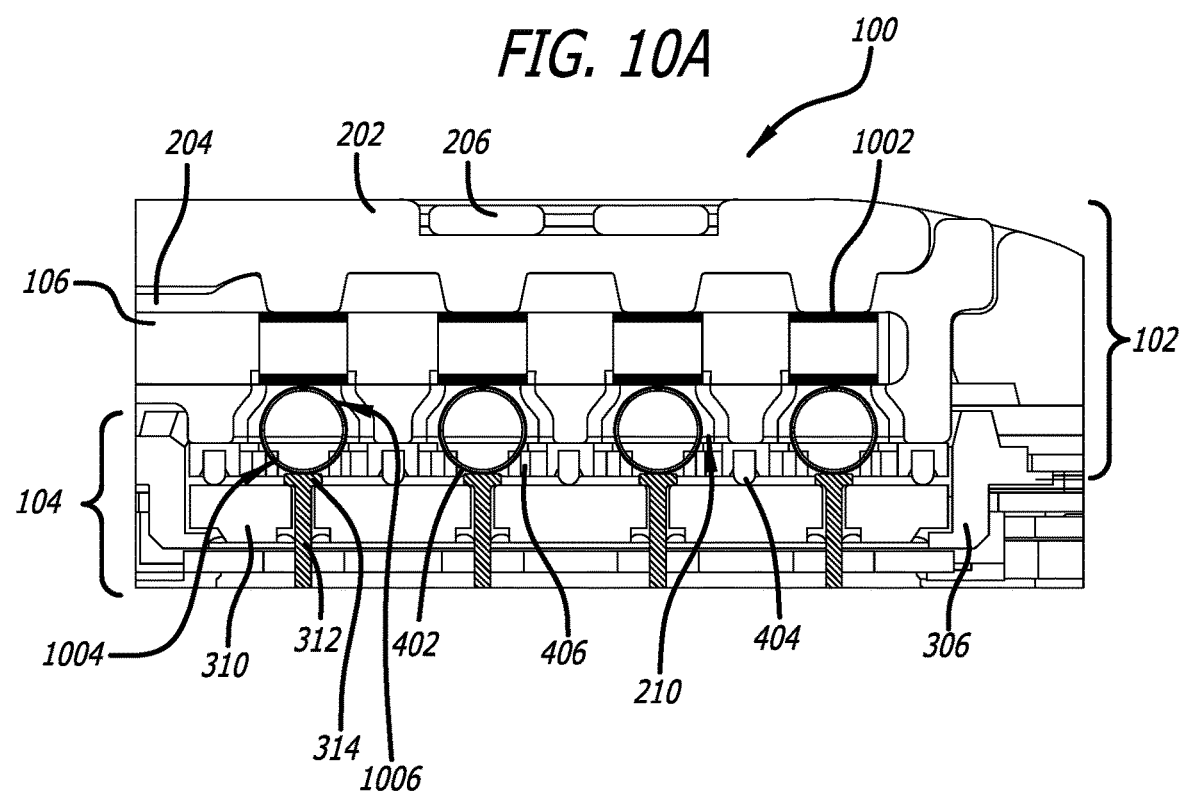
FIG. 10A is a cross-section view showing an initial engagement of a cover assembly to a feedthrough assembly.
Figure 10B:
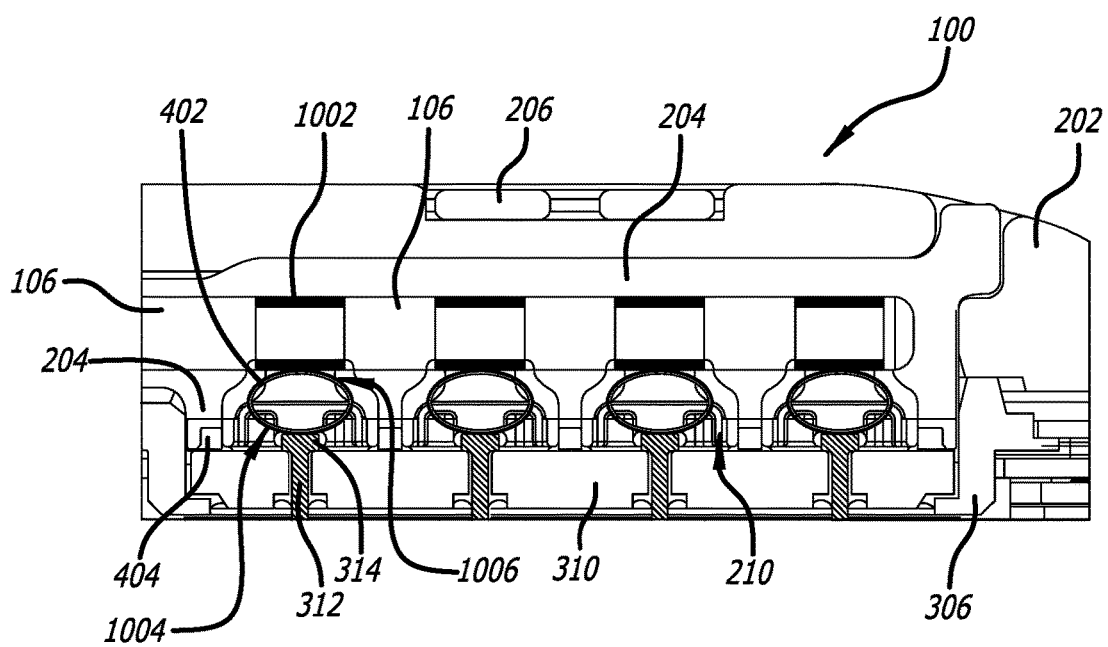
FIG. 10B is a cross-section view showing a full assembly of a cover assembly to a feedthrough assembly.

With reference to FIGS. 10A and 10B, the operation of the connector assembly 100 of FIGS. 1-9B is outlined in the following steps:

One or more leads 106 are inserted into an upper seal 204 of a cover assembly 102.

The cover assembly 102 is aligned with and fastened down onto the feedthrough assembly 104 using the screw 206. As the lower portions of the upper seals 204 seat into a respective rectangular recess 308 in the feedthrough subassembly 302, the upper seals are captured within the recess and thereby are mated to the feedthrough assembly 104.

During fastening of the screw 206, the lower seal 404 of the electrical contact interposer assembly 304 is squeezed between the contact retainer 406 and the feedthrough substrate 310. The contact ring assemblies 402 begin to compress as the lead contacts 1002 are forced downward with the rest of the cover assembly 102 into the feedthrough assembly 104.

As shown in FIG. 10B, as the torque limit for the screw 206 is reached, the cover 202 is clamped against the feedthrough ferrule 306. The upper seals 204 and the lower seals 404 reach sufficient pressure to electrically isolate each of the conduction paths through the connector assembly 100. The contact ring assemblies 402 are compressed sufficiently to establish a reliable electrical connection between first surfaces 1004 of the contact ring assemblies and the feedthrough pins 312 and between second surfaces 1006 of the contact ring assemblies and the lead contacts 1002. The super-elastic characteristic of the nitinol backing ring 502 is able to deform within the radial compression imparted with the cover 202 fully clamped onto the feedthrough ferrule 306. The platinum-iridium contact ring 504 complies with the deflection of the nitinol backing ring 502 while providing a low resistance electrical contact between the lead contact 1002 and the head 314 of the feedthrough pin 312.

With reference to FIG. 5, the nitinol backing ring 502 of the contact ring assembly 402 exhibits properties of super elasticity which enable the ring to deform under radial compression without yielding (breaking). An illustration of a theoretical stress-strain curve of super-elastic nitinol is provided in FIG. 11.

A ring under radial compression is at various stages of stress through the stress-strain curve illustrated in FIG. 11. FIG. 12 illustrates various levels of stress of a ring 1202 (half model) under radial compression as estimated by finite element analysis (FEA). The peak stress is illustrated at the bottom center 1204 of the ring which contacts the surface 1206 the ring is pressed against. With reference to FIG. 11, the nitinol backing ring 502 is configured to stay out of the stage IV region of the stress strain curve (plastic deformation). The yield strength of Nitinol is approximately 814 MPa, therefore the ring 1202 illustrated in FIG. 12 is within the elastic range of the material. The diameter, wall thickness and length of the backing ring 502 can vary to achieve target spring force and elastic range. An illustration of the force-displacement behavior of different geometries during radial compression as estimated by FEA is illustrated in FIG. 13.

With reference to FIGS. 14A and 14B, in some embodiments the contact ring assemblies 1400 of an electrical contact interposer assembly includes a backing ring 1402 having a split 1408 along the width w and at the bottom center of the ring between the locking tabs 1406, and a contiguous contact ring 1404 similar to the contact ring in FIG. 5.

The split backing ring 1402 provides some of advantages to the contact design. The peek stress on the part illustrated in FIG. 12 is reduced by allowing relative movement across the bottom center of the split backing ring 1402. The added compliance of the split backing ring 1402 has the potential effect of expanding the elastic range of the ring. Additionally, assembly of the split backing ring 1402 and the contact ring 1404 is made easier with the split backing ring. The split backing ring 1402 can be compressed to accommodate the fit of the contact ring 1404 more easily over the backing ring. The split backing ring 1402 and the contiguous contact ring 1404 would not need to be made with precise diameter dimensions as describe for the contact ring assembly 402 of FIG. 5, therefore making fabrication of the contacts easier and less expensive. With reference to FIG. 14C, in some embodiments, a split backing ring 1410 includes a cutout 1412 formed at one end of the split ring, and a corresponding extension 1414 at the opposite end of the ring that is sized to fit into the cutout during relative movement of the respective ends.

With reference to FIGS. 15A and 15B, in some embodiments the contact rings assemblies of an electrical contact interposer assembly include a backing ring 1502a, 1502b that varies in width around the circumference of the ring. This contouring around the backing ring 1502a, 1502b reduces the width w of the ring in the areas where stresses are lowest, therefore providing more deflection in the narrow areas and more uniform stress throughout the ring under compression. The backing ring 1502b of FIG. 15B includes one or more windows 1504. While not shown in FIGS. 15A and 15B, a contact having a contoured backing ring 1502a, 1502b also includes a contiguous contact ring similar to the contact ring 1404 in FIG. 14B and the contoured backing ring 1502a, 1502b fits within the contact ring.

Figure 16:
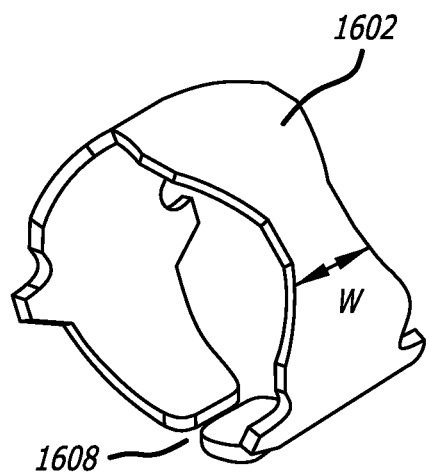

With reference to FIG. 16, in some embodiments the contact ring assemblies of an electrical contact interposer assembly include a backing ring 1602 that varies in width around the circumference of the ring and includes a split 1608. This contouring around the backing ring 1602 reduces the width w of the ring in the areas where stresses are lowest, therefore providing more deflection in the narrow areas and more uniform stress throughout the ring under compression. While not shown in FIG. 16, a contact having a split contoured backing ring 1602 also includes a contiguous contact ring similar to the contact ring 1404 in FIG. 14B and the split contoured backing ring fits within the contact ring. The split contoured ring of FIG. 16 combine the advantages of both the split backing ring 1402, 1410 and contoured backing ring 1502a, 1502b described above into a single backing ring design.

Figure 17A:
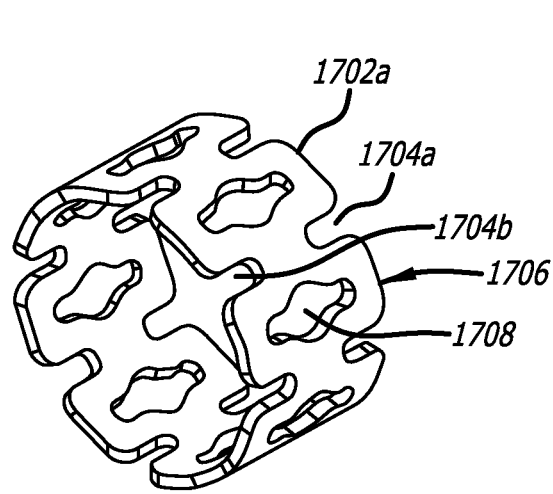
Figure 17B:
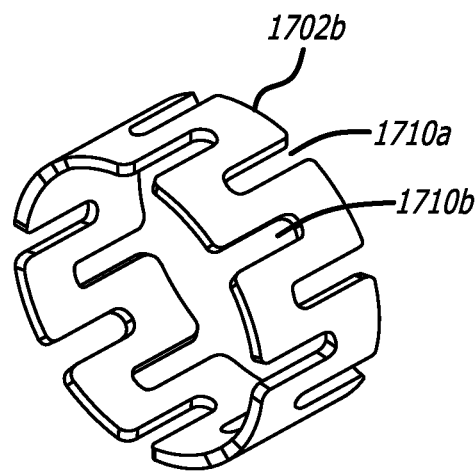
Figure 18A:
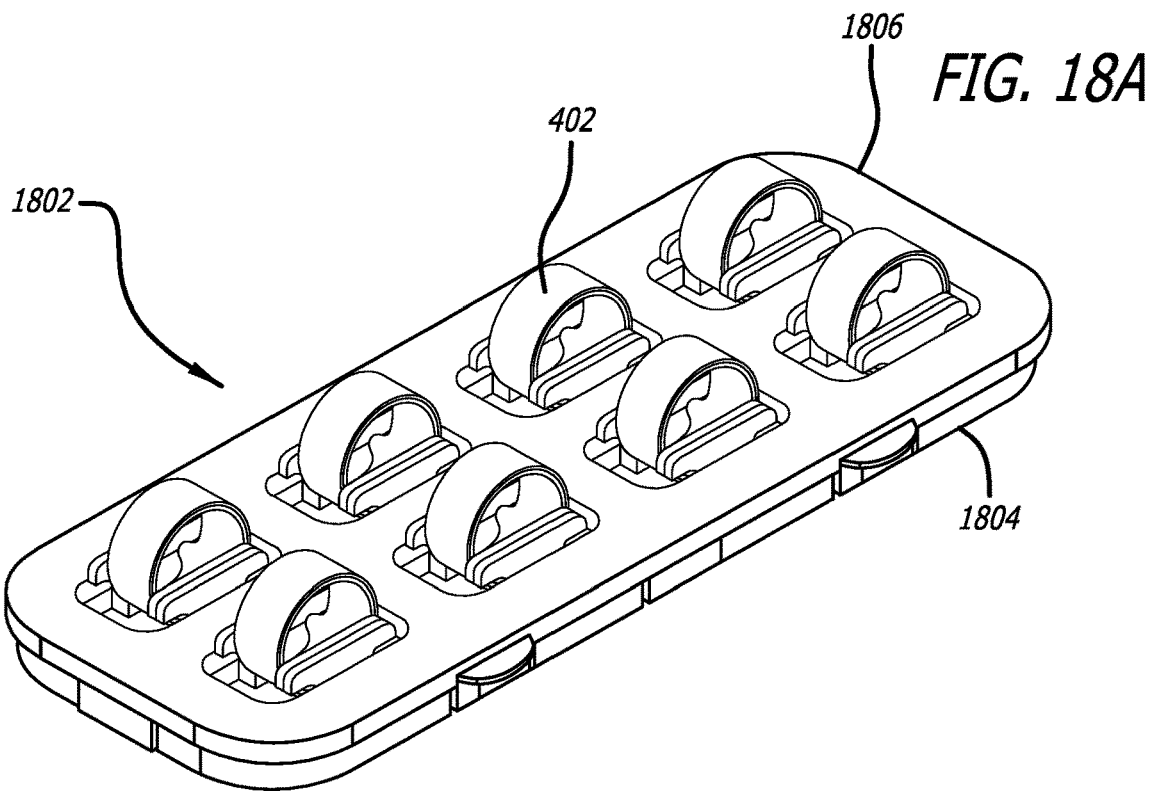
Figure 18B:
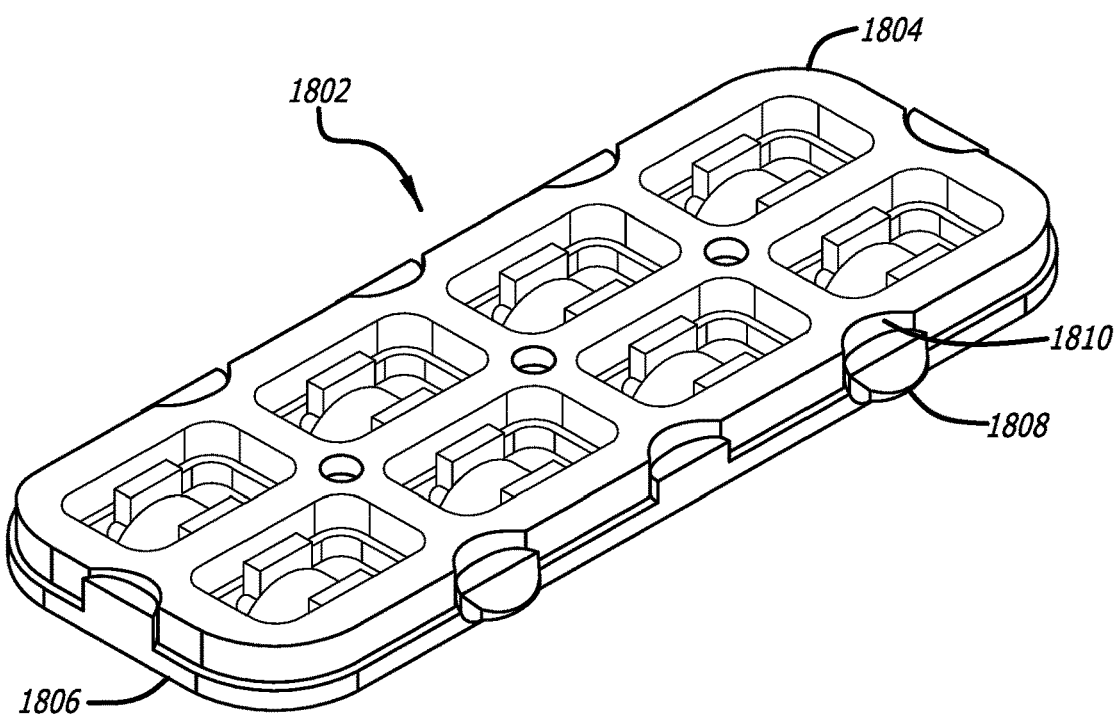

With reference to FIGS. 17A and 17B, in some embodiments the contact ring assemblies of an electrical contact interposer assembly include a backing ring 1702a, 1702b wherein a significant portion of the ring is removed to transition from hoop stress to torsional tresses in the ring. These stent backing rings 1702a, 1702b result in a substantially less stiffness in the ring and an extended elastic range of the ring under radial compression. The stent backing ring 1702a is symmetric with opposed notches 1704a, 1704b equally spaced around the circumference of the ring that form interconnected rectangular portions 1706, each with a window 1708. The stent backing ring 1702b is asymmetric with non-aligned notches 1710a, 1710b spaced around the circumference of the ring. While not shown in FIGS. 17A and 17B, a contact ring assembly having a stent backing ring 1702a, 1702b also includes a contiguous contact ring similar to he contact ring 1404 in FIG. 14B and the stent backing ring fits within the contact ring and is retained therein by an interference fit.

With reference to FIGS. 18A, 18B, 19A, and 19B in some embodiments an electrical contact interposer assembly 1802 includes a lower seal 1804 that is placed on the underside of a contact retainer 1806, as opposed to mating with a recess (as in the embodiment of FIG. 4). In this embodiment, the contact retainer 1806 includes ferrule locks 1808 that align with notches 1810 around the perimeter of the lower seal 1804. The ferrule locks 1808 secure the lower seal 1804 to the contact retainer 1806 through a mechanical, e.g., snap-fit, coupling. With additional reference to FIG. 3, the lower seal 1804 provides increased seal width and thus increased electrical isolation between the heads 314 of feedthrough pins 312 and the contact ring assemblies 402 when a cover assembly is clamped. The lower seal 1804 also minimizes acute pinching between the contact retainer 1806 and the feedthrough substrate 310 of a feedthrough assembly.

Figure 20:
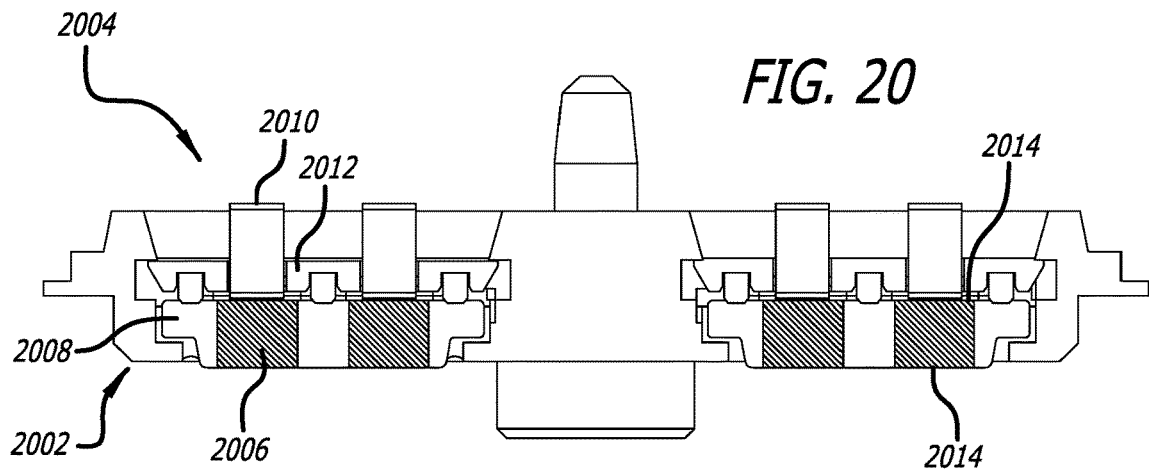
FIG. 20 is a cross-section view of a feedthrough assembly having a leadless feedthrough subassembly.

The feedthrough assembly 104 of FIG. 3 includes a feedthrough subassembly 302 having a feedthrough substrate 310 having feedthrough pins 312 with projecting heads 314 that are positioned to contact the contact ring assemblies 402. With reference to FIG. 20, in other configurations, the feedthrough assembly 2004 may include a co-fired or leadless feedthrough subassembly 2002. In the leadless feedthrough subassembly 2002, conductive vias 2006 extend through a feedthrough substrate 2008 to form conductive paths having an exposed conductive surfaces 2014 flush with each side of the feedthrough substrate. In this feedthrough assembly 2004, contact ring assemblies 2010 retained in a contact retainer 2012 are positioned adjacent a conductive surface 2014.

B. Feedthrough Assembly with Attached Contacts

In some embodiment the contacts of a connector assembly may be permanently attached to a feedthrough assembly. For example, the contacts may be covalently bonded to the feedthrough contacts of the feedthrough assembly by a laser welding process. Disclosed herein are different configurations of attached contacts. These attached contacts may be referred to as leaf spring contacts, leaf spring contact assemblies, torsion spring contacts, and torsion spring contact assemblies.

1. Leaf Spring Contact Assemblies

With reference to FIGS. 21-27, in some embodiments a connector assembly 2100 of an implantable medical device includes a cover assembly 2102 and a feedthrough assembly 2104 configured to couple with the cover assembly. The cover assembly 2102 is configured to receive a connector end of a lead 2110 having lead contacts 2112, and to align the lead contacts with apertures 2114 of the cover assembly 2102. The feedthrough assembly 2104 includes feedthrough contacts 2108. Attached electrical contact assemblies 2106 are located on the feedthrough contacts 2108 and in the apertures 2114 when the cover assembly 2102 and feedthrough assembly 2104 are coupled. Each of the attached electrical contact assemblies 2106 includes an attachment feature 2510 permanently coupled to a feedthrough contact 2108 and a contact engagement feature 2512 positioned in the aperture 2114.

In the embodiment of FIGS. 21-27 the attached electrical contact assemblies 2106 are configured as leaf spring contact assemblies, and are referred to as compressive contact assemblies in that they are configured to be compressed during coupling of the cover assembly 2102 and the feedthrough assembly 2104. The leaf spring contact assemblies 2106 are attached to feedthrough contacts in the form of conductive via pads 2108 that extend through a feedthrough substrate 2116 of the feedthrough assembly.

Figure 25:
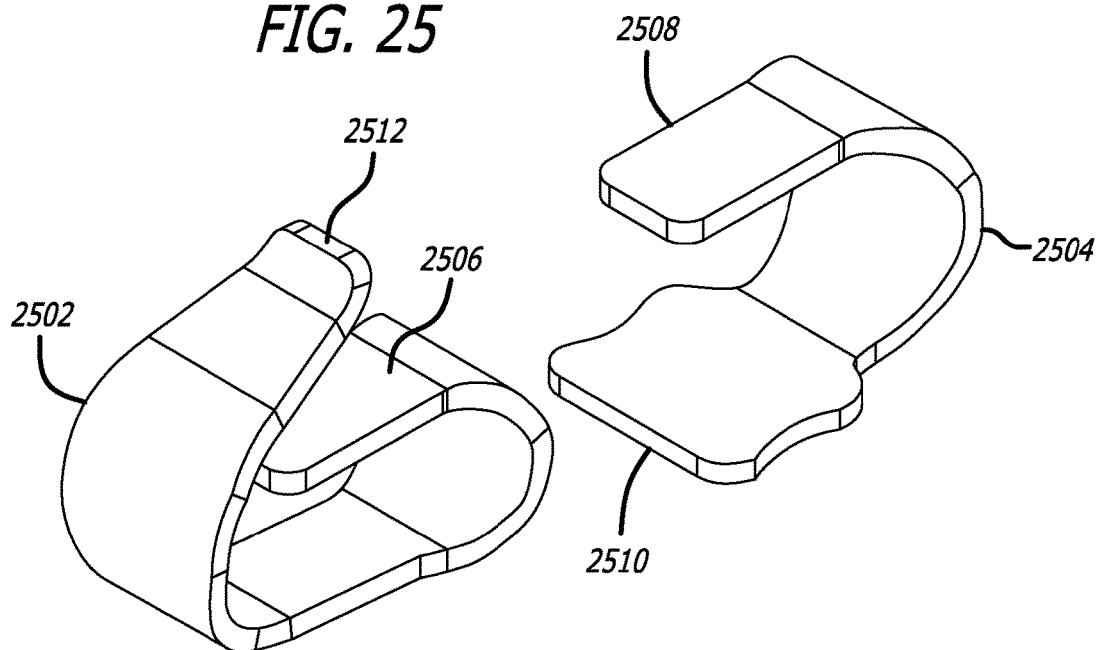
FIG. 25 is a disassembled view of the leaf spring contact assembly of FIG. 23 including a compressive contact and an elastic mount.
Figure 26:
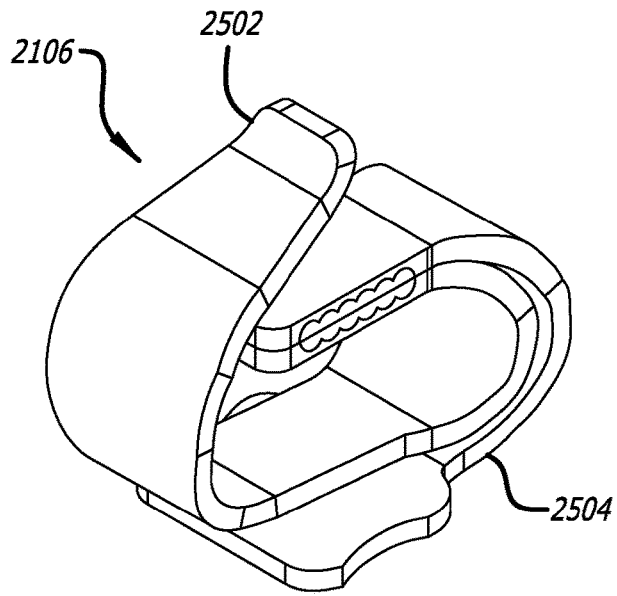
FIG. 26 is a perspective view of a leaf spring contact assembly of FIG. 23.
Figure 27:
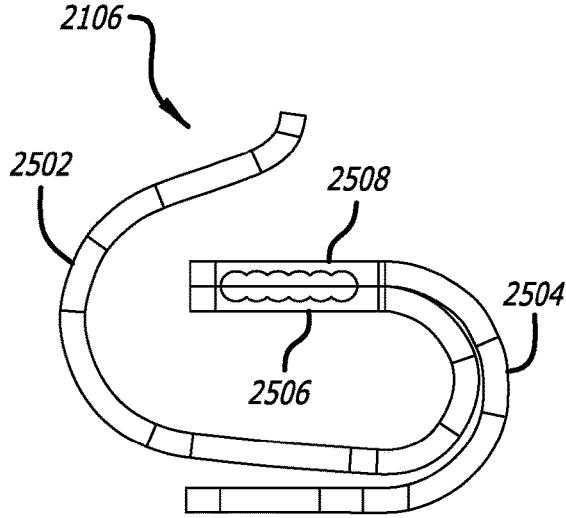
FIG. 27 is a side view of the leaf spring contact assembly of FIG. 26, showing the compressive contact joined to the elastic mount by welding.
Figure 28:
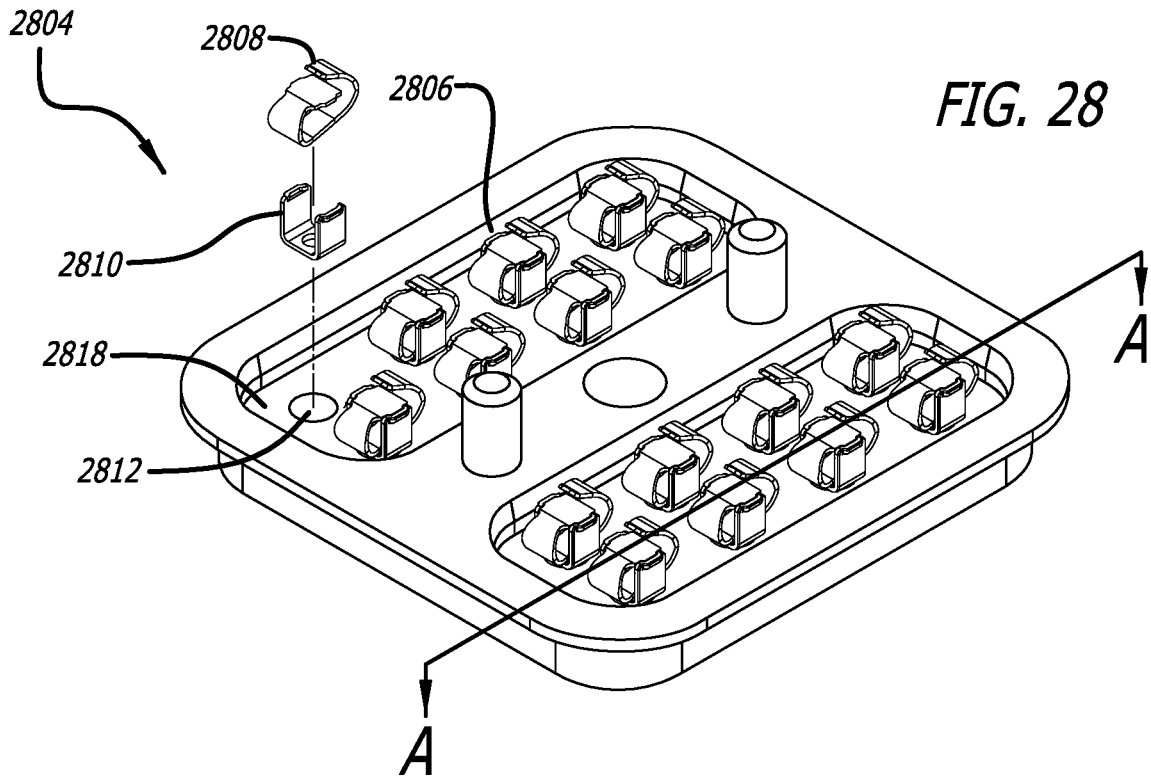
FIG. 28 is an illustration of another feedthrough assembly with contacts configured as leaf spring contact assemblies that may be used in place of the feedthrough assembly of FIG. 23.
Figure 29:
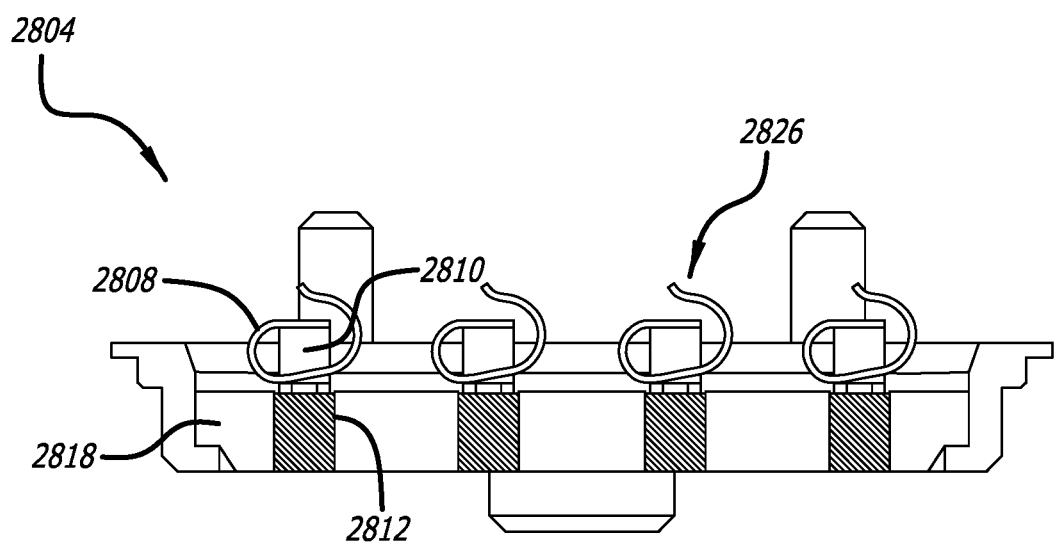
FIG. 29 is a cross-sectional view of the feedthrough assembly of FIG. 28 along line A-A.
Figure 33:
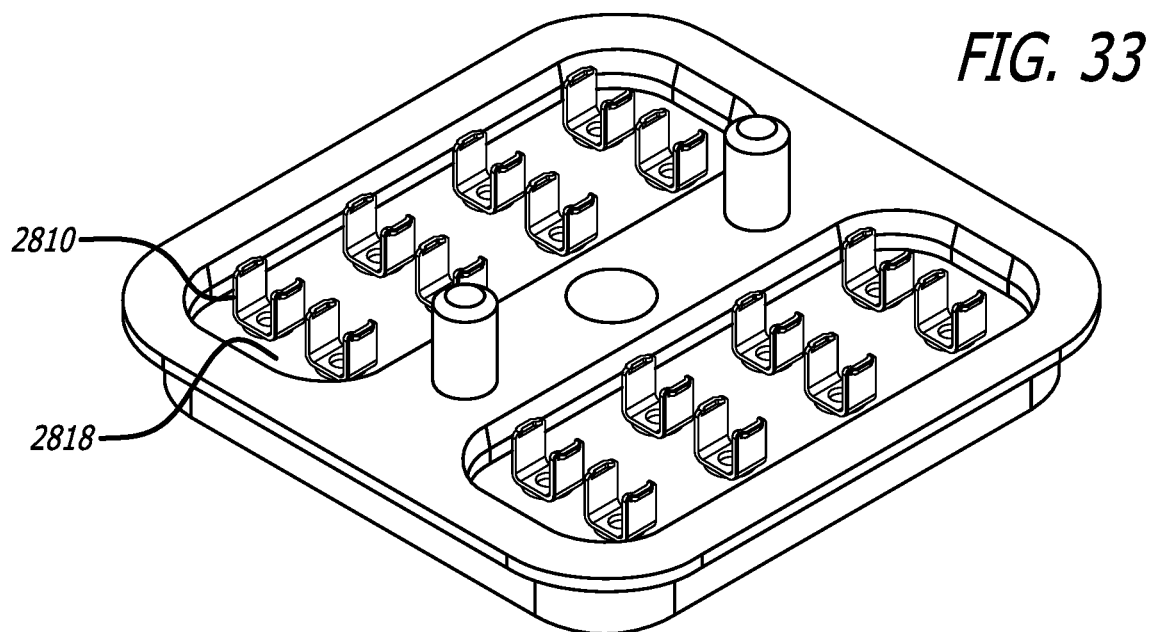
FIG. 33 is an illustration of the feedthrough assembly of FIG. 28 with the compressive contacts of the leaf spring contact assemblies removed from the U-shaped contact mounts.
Figure 34:
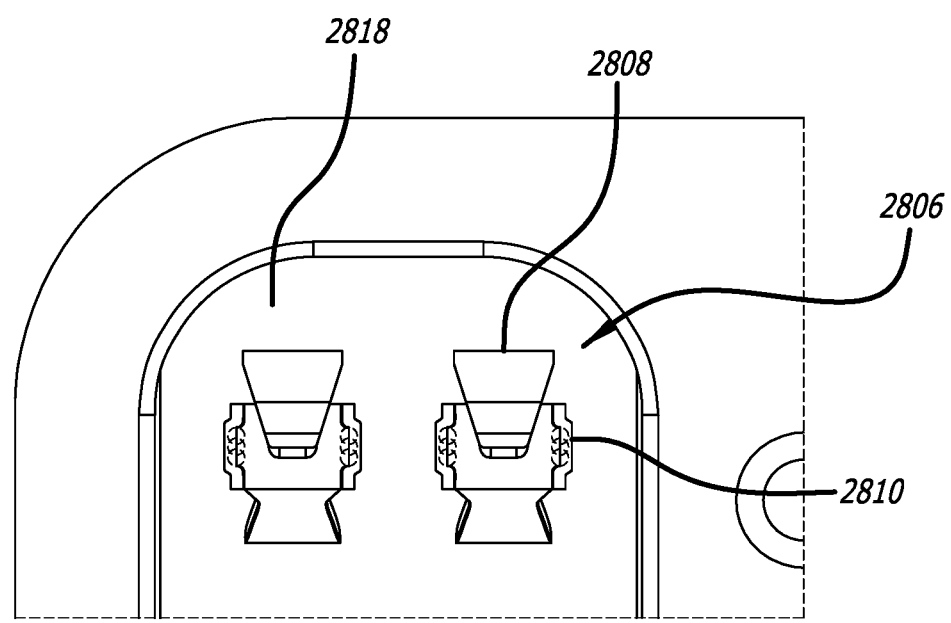
FIG. 34 is a top view of a portion of the feedthrough assembly of FIG. 28.
Figure 35:
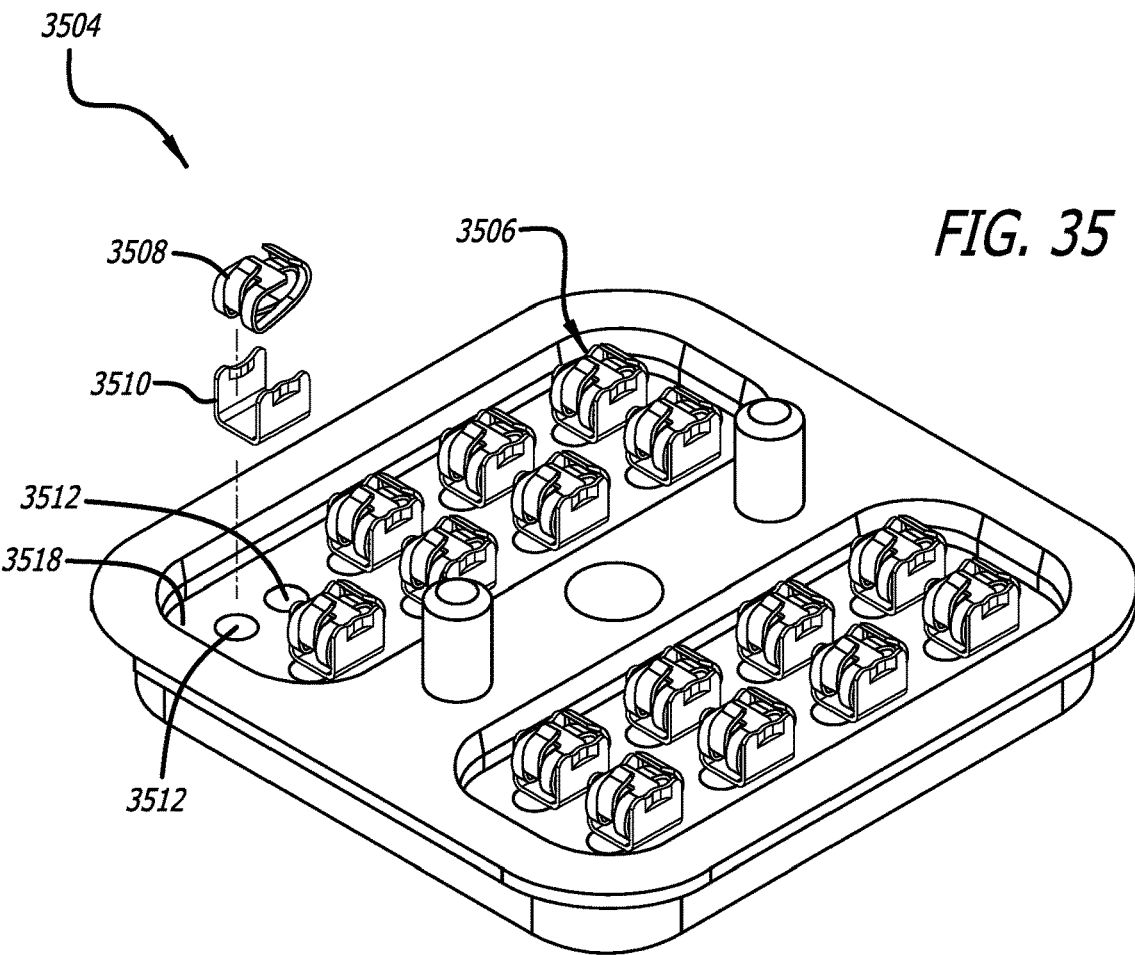
FIG. 35 is an illustration of a feedthrough assembly with another form of leaf spring contact assemblies.
Figure 36:
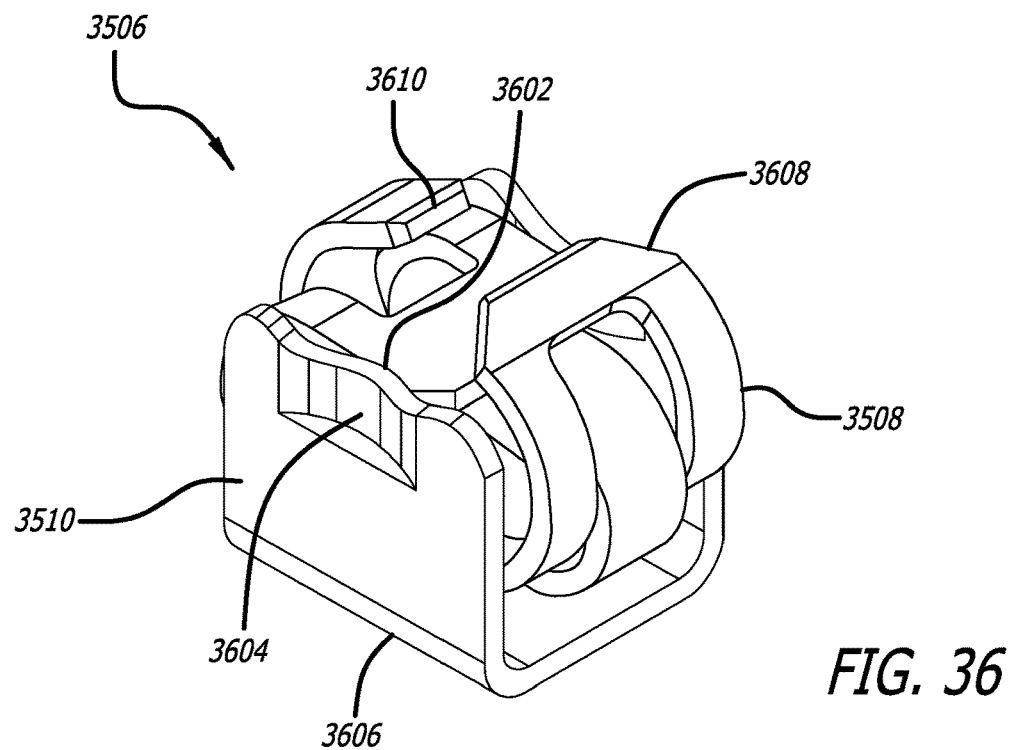
FIG. 36 is a perspective illustration of a leaf spring contact assembly of FIG. 35 including a compressive contact and a U-shaped mount.

As shown in FIGS. 25-27, each leaf spring contact assembly 2106 includes a compressive contact 2502 and an elastic mount 2504. The elastic mount 2504 includes the attachment feature 2510, while the compressive contact 2502 includes the contact engagement feature 2512. A coupling portion 2506 of the compressive contact 2502 is joined to a coupling portion 2508 of the elastic mount 2504. The coupling portions 2506, 2508 may be joined by welding. The elastic mounts 2504 are electrically coupled through the attachment feature 2510 to conductive via pads 2108 of the feedthrough assembly by, for example, welding. The compressive contact 2502 may be made of 80-20 platinum-iridium alloy. The elastic mount 2504 may be made of 80-20 or 90-10 platinum-iridium alloy.

Figure 21:
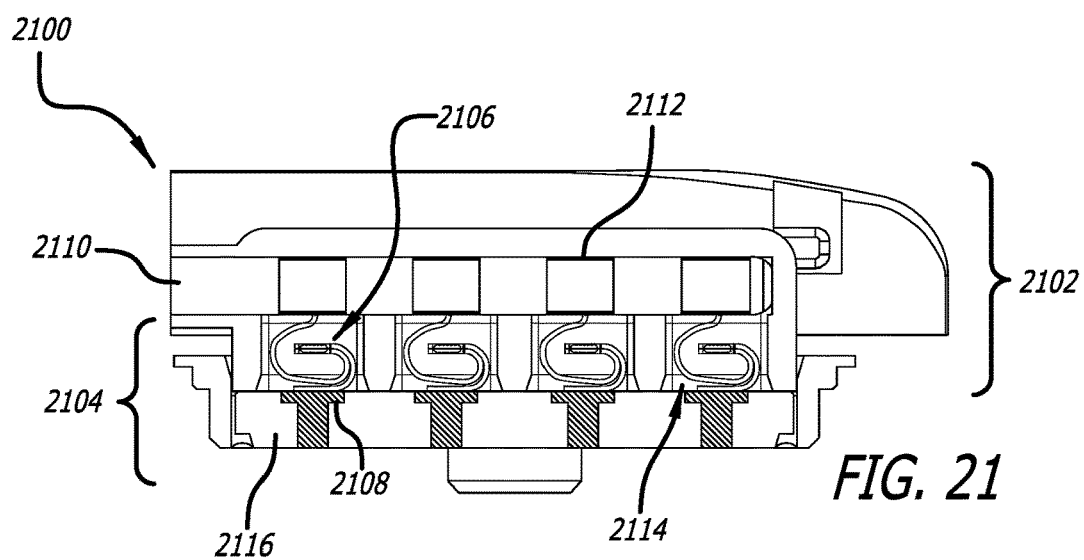
FIG. 21 is a cross-section view of a portion of a connector assembly that includes a cover assembly and a feedthrough assembly, wherein the feedthrough assembly includes contacts configured as leaf spring contact assemblies that are inseparable from, or permanently attached to the feedthrough assembly.
Figure 22:
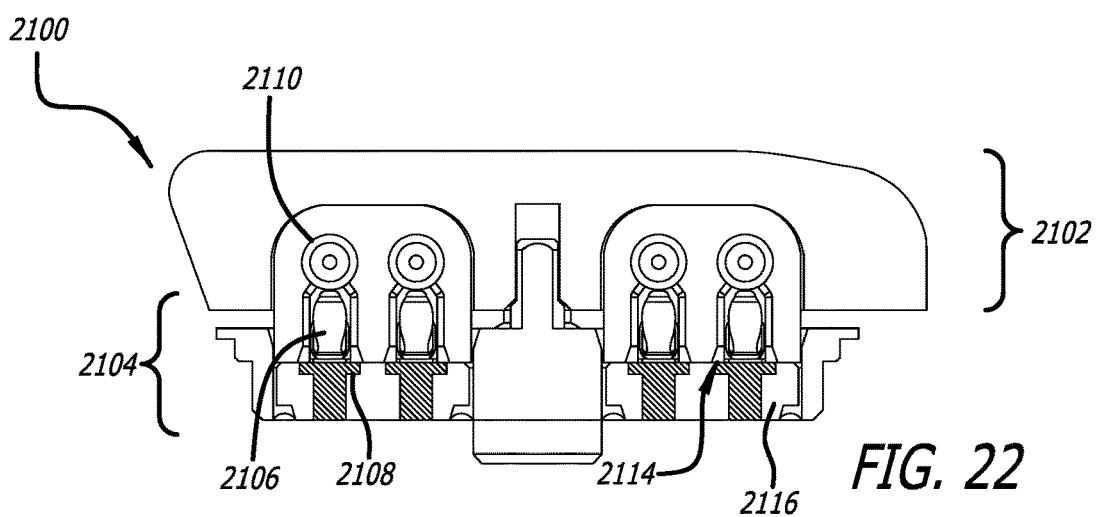
FIG. 22 is a cross-sectional view, taken across the leaf spring contact assemblies of the connector assembly of FIG. 21.
Figure 23:
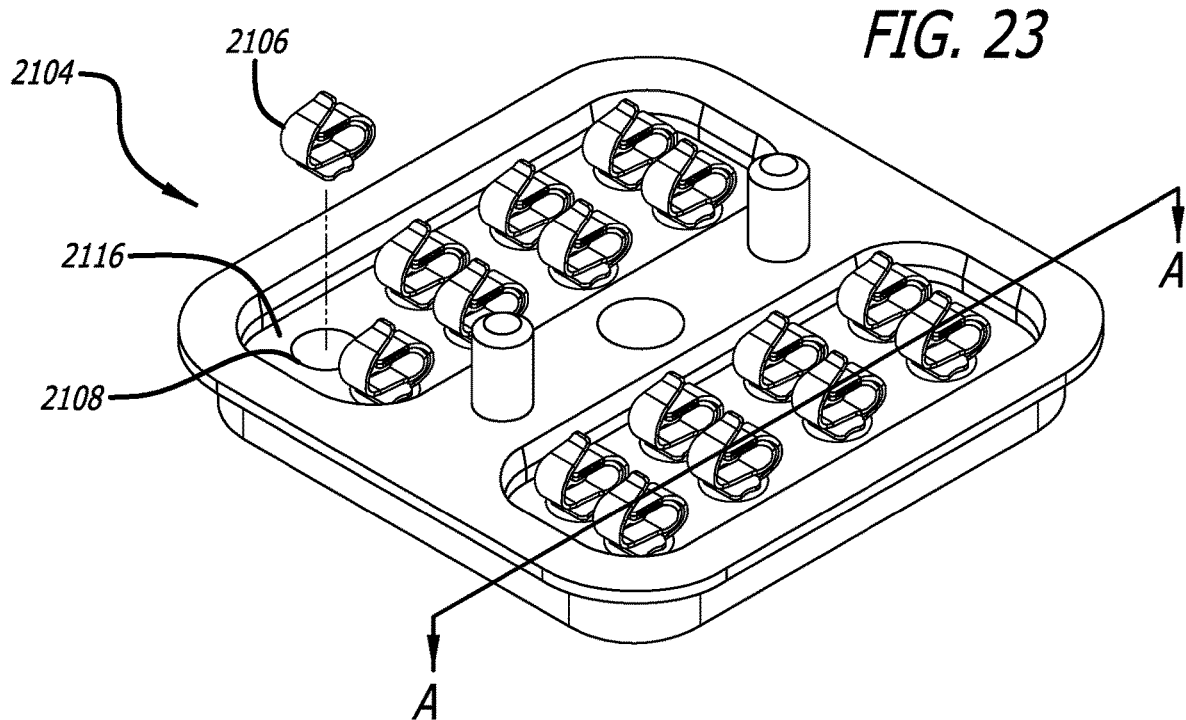
FIG. 23 is an illustration of the feedthrough assembly of FIG. 21.
Figure 24:
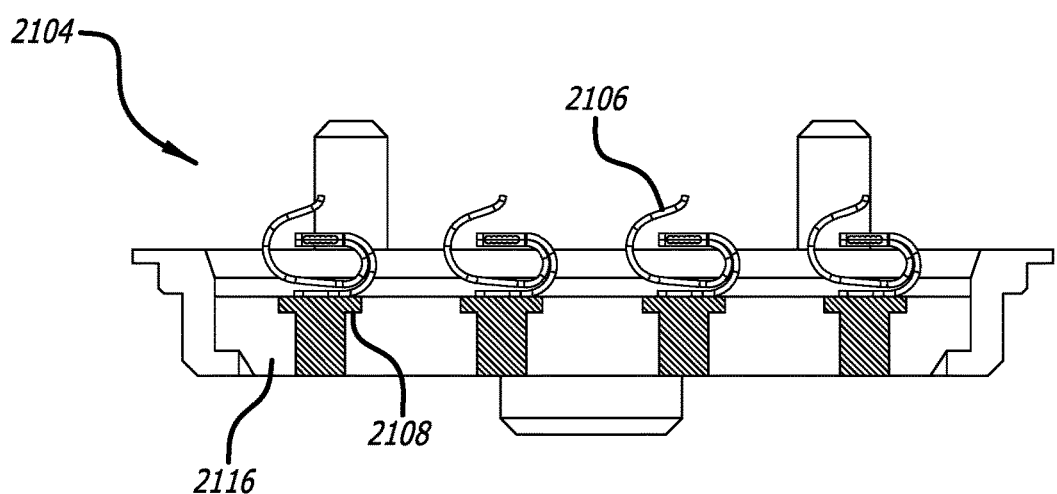
FIG. 24 is a cross-sectional view of the feedthrough assembly of FIG. 23 along line A-A.

Different configurations of feedthrough assemblies having different configurations of leaf spring contact assemblies may be used in place of the feedthrough assembly 2104 shown in FIG. 21. For example, with reference to FIGS. 28-34, in some embodiments a feedthrough assembly 2804 includes leaf spring contact assemblies 2806 that includes a compressive contact 2808 coupled to a U-shaped mount 2810. The U-shaped mount 2810 includes an attachment feature 2816 that attaches to feedthrough contacts 2812 in the form of conductive via pads 2812 extending through a feedthrough substrate 2818 of the feedthrough assembly 2804. The compressive contact 2808 includes a contact engagement feature 2814. With reference to FIG. 32, coupling features 3202 corresponding to edges of the compressive contact 2808 are attached to coupling features 3204 corresponding to top edges of the U-shaped mounts 2810 by, for example, laser welding to provide electrical coupling between the U-shaped mount 2810 and the compressive contact 2808. The U-shaped mounts 2810 are electrically coupled through the attachment feature 2816 to conductive via pads 2812 of the feedthrough assembly by, for example, welding. The compressive contact 2808 may be made of 80-20 platinum-iridium alloy. The U-shaped mount 2810 may be made of 80-20 or 90-10 platinum-iridium alloy.

With reference to FIGS. 35-38, in some embodiment a feedthrough assembly 3504 includes leaf spring contact assemblies 3506 that includes a compressive contact 3508 and a U-shaped mount 3510. The U-shaped mount 3510 includes an attachment feature 3606 that attaches to feedthrough contacts in the form of conductive via pads 3512 extending through a feedthrough substrate 3518 of the feedthrough assembly 3504. The compressive contact 3508 includes a pair of contact engagement features 3608, 3610. Similar to the configuration of FIGS. 28-34, coupling features 3602 corresponding to edges of the compressive contact 3508 are attached to coupling features 3604 corresponding to top edges of the U-shaped mounts 3510 by, for example, laser welding to provide electrical coupling between the U-shaped mount 3510 and the compressive contact 3508. The U-shaped mounts 3510 are electrically coupled through the attachment feature 3606 to a pair of conductive via pads 3512 of the feedthrough assembly by, for example, welding. The compressive contact 3508 may be made of 80-20 platinum-iridium alloy. The U-shaped mount 3510 may be made of 80-20 or 90-10 platinum-iridium alloy.

Figure 37:
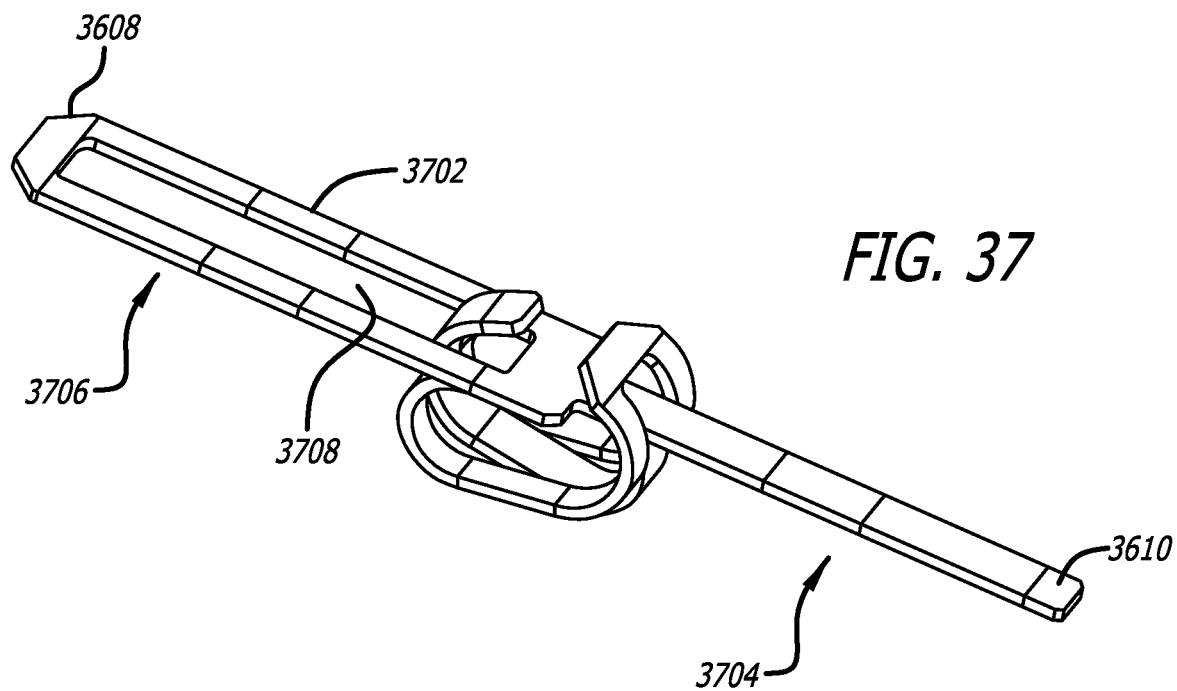
FIG. 37 is a visualization of the forming of the compressible contact of the leaf spring contact assembly of FIG. 36.
Figure 38:
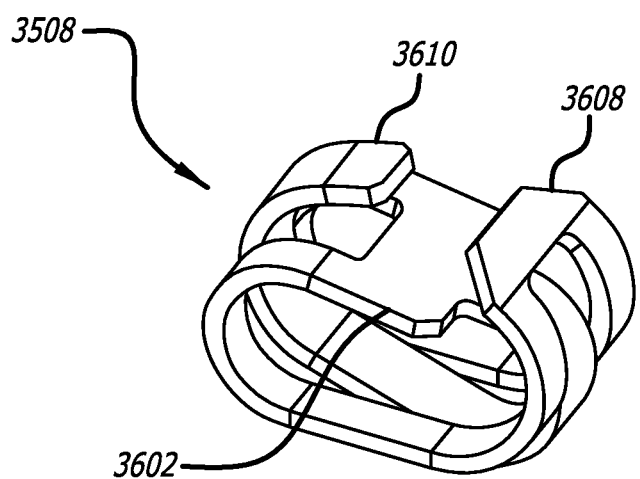
FIG. 38 is an illustration of the compressible contact of the leaf spring contact assembly of FIG. 36.

With reference to FIGS. 37 and 38, a compressive contact 3508 with the spiral-formed leaves is formed from a flat contact 3702 by bending each of a narrow end 3704 and a wide end 3706, such that the narrow end rests inside of a window 3708 formed in the wide end.

2. Torsion Spring Contacts and Torsion Spring Contact Assemblies

In the conventional leaf spring contacts, the active length of the spring operates in a bending mode. Achieving adequate active spring length in such contacts becomes challenging when a small leaf contact footprint is required. The stamped leaf spring contacts disclosed above enable adequate contact force and deflection capability in a small contact footprint, such as 1 mm×2 mm. However, in order to maximize the active length of the spring, these leaf spring contacts have significant height and/or require two piece construction. The contact height and the limited welding access increase the difficulty of attaching miniature leaf contacts to the conductive vias in the feedthrough assembly. Free standing welded miniature contacts are also naturally susceptible to damage due to inadvertent contact, such as may occur during connection of the leads to the device in a surgical environment.

There is a need for one piece, low profile miniature contacts, with improved attachability to the conductive vias of the feedthrough and enhanced handling integrity. The torsion spring contacts and torsion spring contact assemblies disclosed below address these needs. The connector assemblies disclosed below utilizes torsion spring contacts and torsion spring contact assemblies that are attached directly to conductive vias in the feedthrough or feedthrough pins. The active length of the torsion spring contacts form an open spring loop or spring coil that is substantially parallel to the surface of the dielectric substrate of the feedthrough assembly. This results in a low profile and small footprint contact with a substantial active length of the spring.

The torsion spring contacts and torsion spring contact assemblies disclosed herein have a spring loop or spring coil that has attached end and a free end. On the attached end, there is an attachment feature or tab for attachment to the conductive vias or feedthrough pins. Extending from the free end of the spring coil, is a contact tab or contact engagement feature for making separable pressure connection to the respective proximal contact of the lead. The active spring loop occupies the perimeter of the footprint of the torsion spring contact. The attachment feature and the contact engagement feature are centrally disposed within the outline of the loop. This maximizes the active length of the torsion spring contact and provides an ample attachment access, such as may be required by laser welding.

When the torsion spring contact is attached to the conductive vias or feedthrough pins and a compressive contact force is applied to the tip of the contact engagement feature, the active spring loop behaves substantially as a single coil of a coil spring. Therefore, the elastic deflection of the torsion spring contact and the resulting contact force are primarily due to torsion in the spring loop. In some embodiments, the active spring loop is protectively confined in a counterbore of the dielectric substrate. The walls of the counterbore limit lateral excursion of the torsion spring contact beyond its elastic limits when an inadvertent side load is applied to the contact engagement feature. Similarly, a compressive deflection of the torsion spring contact is limited by a predetermined amount of clearance under the contact engagement feature. The twisting of the spring in the active spring loop provides an elastic deflection and wiping action at the contact interface. The edge of the contact tip may be coined to a desired geometry to increase localized pressure at the interface between the contact tip and the lead contact.

Various embodiments of torsion spring contacts are disclosed, including ones that attach to brazed feedthrough pins and ones that attach to feedthrough vias.

Figure 41:
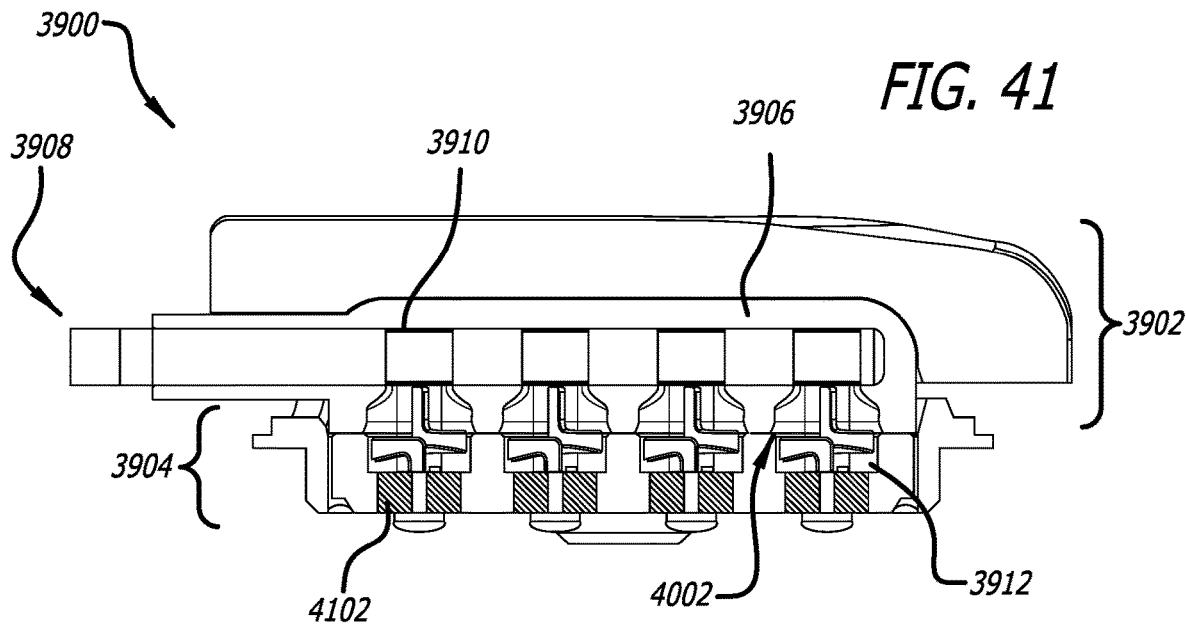
FIG. 41 is a cross-sectional view of the connector assembly of FIG. 39 when the cover assembly is coupled to, but not fully seated with the feedthrough assembly, taken along the lead.
Figure 42:
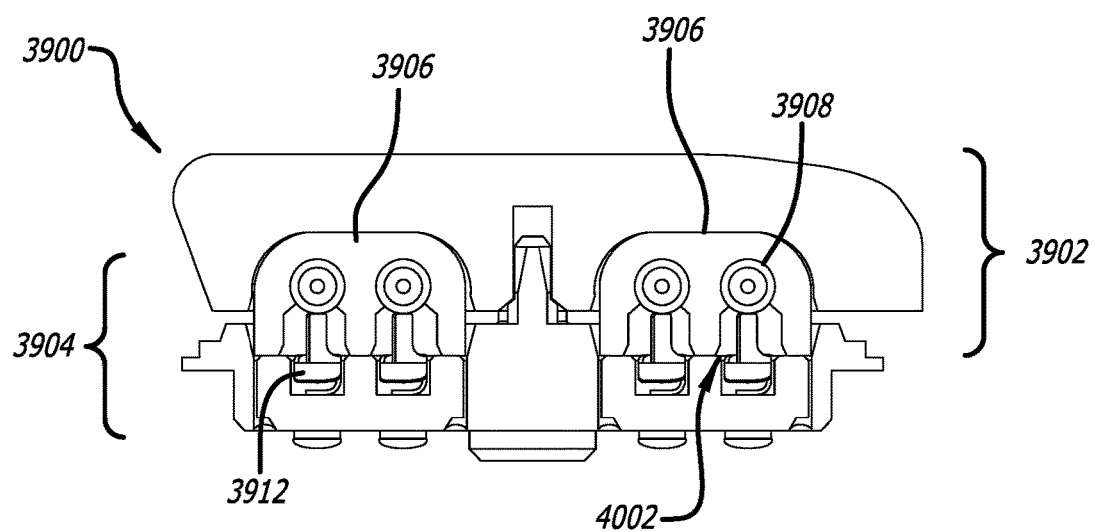
FIG. 42 is a cross-sectional view of the connector assembly of FIG. 39 when the cover assembly is coupled to, but not fully seated with, the feedthrough assembly, taken at a right angle to the leads.

With reference to FIGS. 39-50, in some embodiments a connector assembly 3900 of an implantable medical device includes a cover assembly 3902 and a feedthrough assembly 3904 configured to couple with the cover assembly. The cover assembly 3902 is configured to receive a connector end of a lead 3908 having lead contacts 3910, and to align the lead contacts with pockets or apertures 4002 of the cover assembly 3902. The feedthrough assembly 3904 includes feedthrough contacts 4102 in the form of conductive vias. As shown in FIGS. 41 and 42, attached electrical contacts 3912 configured as torsion spring contacts are attached to the feedthrough contacts 4102 and are located in the apertures 4002 when the cover assembly 3902 and feedthrough assembly 3904 are coupled. With reference to FIG. 49, each of the attached electrical contacts 3912 includes an attachment feature 4328 permanently coupled to a feedthrough contact 4102 and a contact engagement feature 4316 positioned in an aperture 4002.

Figure 39:
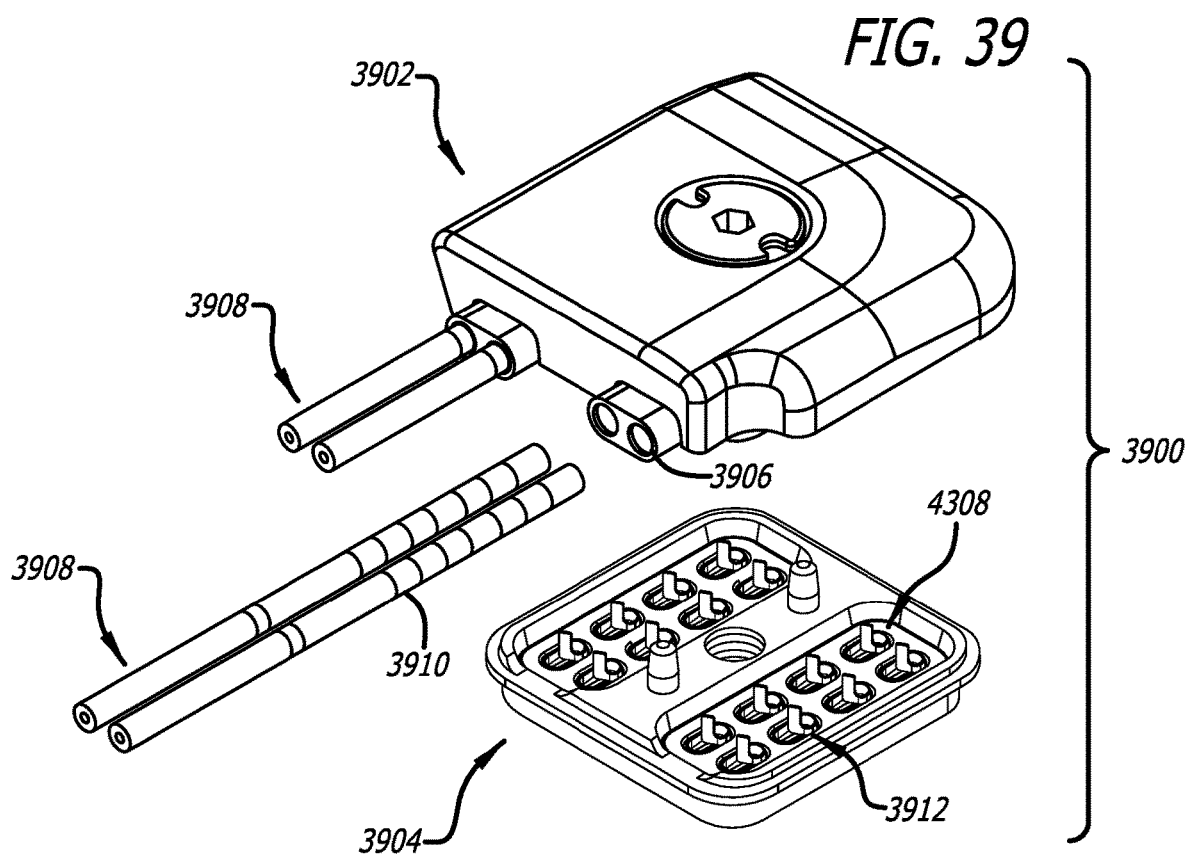
FIG. 39 is an illustration of a connector assembly that includes a cover assembly and a feedthrough assembly, wherein the cover assembly is decoupled from the feedthrough assembly and the feedthrough assembly includes contacts configured as torsion spring contacts that are inseparable from, or permanently attached to the feedthrough assembly.
Figure 40:
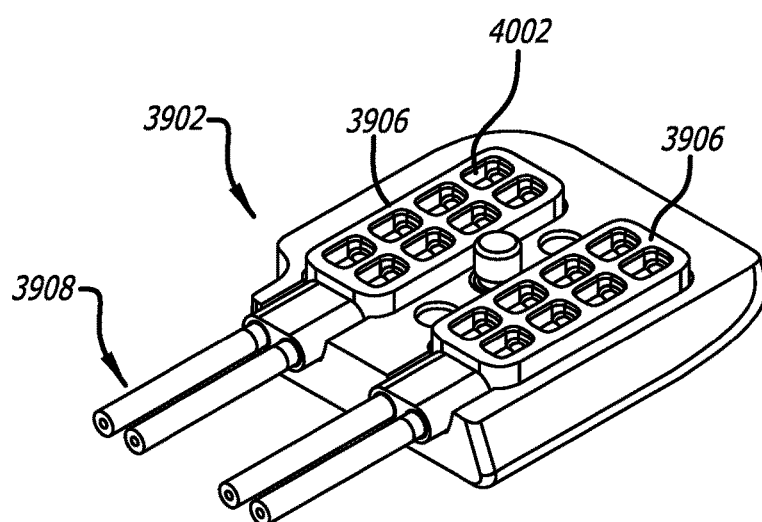
FIG. 40 is an illustration of the cover assembly of FIG. 39 with the feedthrough side of the cover assembly facing up, to reveal seals.

The cover assembly 3902 includes a pair of seals 3906, each configured to receive a connector end of a lead 3908 that carries a number of lead contacts 3910. The feedthrough assembly 3904 includes torsion spring contacts 3912 that provide electrical connections between the lead contacts 3910 and conductive vias 4102 that extend through the feedthrough assembly. In the configuration of FIG. 39, there are four rows of torsion spring contact 3912, with each row having four assemblies. In FIGS. 41 and 42, the cover assembly 3902 and the feedthrough assembly 3904 are coupled, but the cover assembly is not fully secured to the feedthrough assembly. Because the cover assembly 3902 and the feedthrough assembly 3904 are not fully secured to each other, the torsion spring contacts 3912 are not compressed between the lead contacts 3910 and the conductive vias 4102. This uncompressed state of the torsion spring contacts 3912 may be referred to as a free state.

Figure 43:
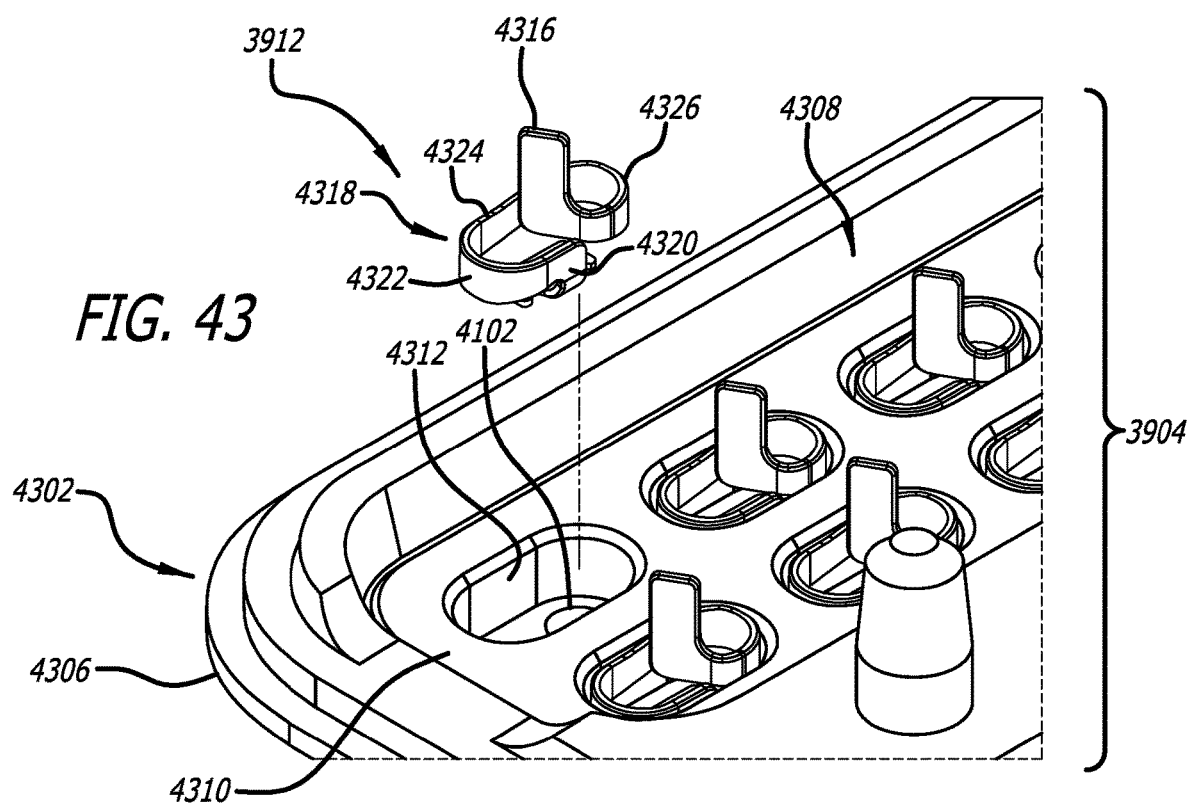
FIG. 43 is an enlarged detail view of a portion of the feedthrough assembly of FIG. 39 showing a torsion spring contact raised above a dielectric substrate of the feedthrough assembly.
Figure 44:
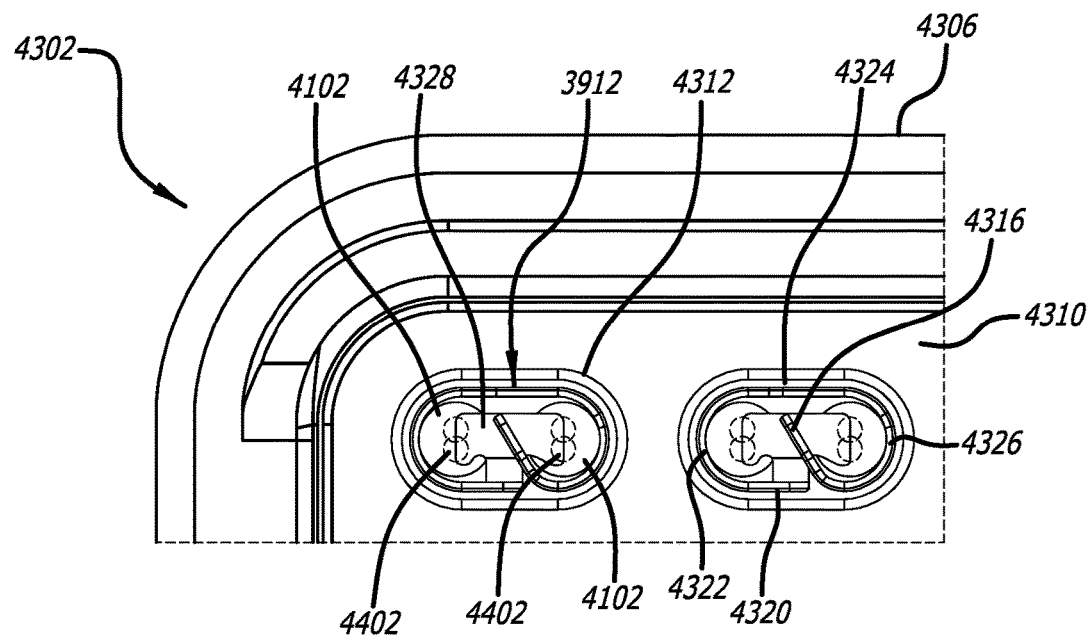
FIG. 44 is an enlarged top view of a portion of the feedthrough assembly of FIG. 39 showing a torsion spring contact occupying a counterbore of the dielectric substrate.
Figure 45:
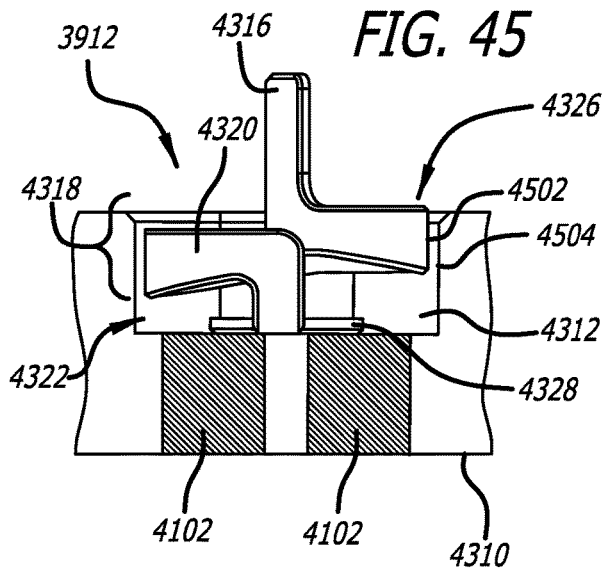
FIG. 45 is a partial cross-sectional view of the feedthrough assembly of FIG. 41 showing a torsion spring contact in free state, confined in a counterbore of a dielectric substrate.
Figure 46:
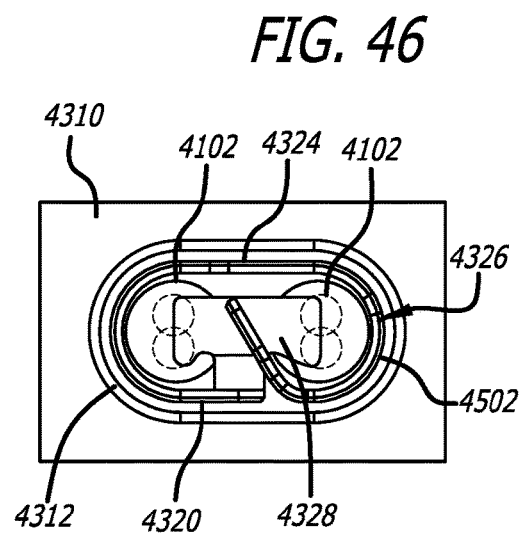
FIG. 46 is a partial top view of the feedthrough assembly of FIG. 41, showing a torsion spring contact within counterbore of a dielectric substrate.

With reference to FIGS. 43 and 44, the feedthrough assembly 3904 includes a feedthrough subassembly 4302 to which the torsion spring contacts 3912 are permanently attached. The feedthrough subassembly 4302 includes a feedthrough ferrule 4306 with a pair of rectangular recesses 4308, each with a dielectric, e.g., ceramic, substrate 4310 placed therein. The dielectric substrate 4310 includes a number of counterbores 4312 corresponding in number to the number of torsion spring contacts 3912. The base of each counterbore 4312 includes a pair of conductive vias 4102 that pass through the bottom of the dielectric substrate 4310 providing electrical conduction paths between opposite sides of the feedthrough ferrule 4306. The attachment base 4328 of the torsion spring contacts 3912 is permanently attached, e.g., welded, to each conductive via 4102 within a counterbore 4312 at attachment points 4402.

With reference to FIGS. 43-50, the torsion spring contacts 3912 comprise a continuous piece of material that is bent, shaped, and formed to include a spring loop 4318 having a free side 4326 and an attached side 4322, and a contact tab or contact engagement feature 4316 that extends from the free side. An attachment feature 4328, referred to as an attachment base, is included in the attached side 4322. The spring loop 4318 has a perimeter with a shape corresponding to the perimeter shape of the counterbores 4312 and is sized to fit within the counterbore. In the configuration of FIGS. 43 and 44, the perimeter shape of the counterbore 4312 and the spring loop 4318 is a discorectangle, i.e., a geometric shape consisting of a rectangle with top and bottom lengths whose ends are capped off with semicircles of radius. Other shapes, however, are possible.

The spring loop 4318 is open (does not form a continuous or closed geometric shape) and includes spiral portion that extends from the attachment base 4328. The spiral portion spirals from a first linear side 4320 that extends from the attachment base 4328 through a first semicircular radius of the attached side 4322, through a second linear side 4324 through a second semicircular radius of the free side 4326, and terminates at the contact engagement feature 4316. The contact engagement feature 4316 projects upward relative to the spring loop 4318 and in a direction of an aperture of the cover assembly 6602. This formation of the torsion spring contacts 3912 places the edge of the contact engagement feature 4316 at a location above the top surface of the dielectric substrate 4310. The torsion spring contacts 3912 are electrically coupled to the conductive vias 4102 through the attachment base 4328. For example, each end of the attachment base 4328 may be laser welded to a respective one of the conductive vias 4102 at the base of a counterbore 4312.

Figure 47:
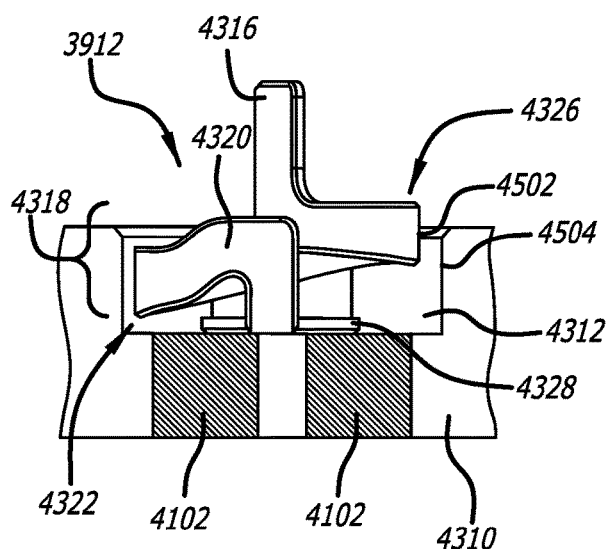
FIG. 47 is a partial cross-sectional view of the feedthrough assembly of FIG. 41 showing a torsion spring contact with increased clearance between a free side of the contact and an inside wall of a counterbore of a dielectric substrate.
Figure 48:
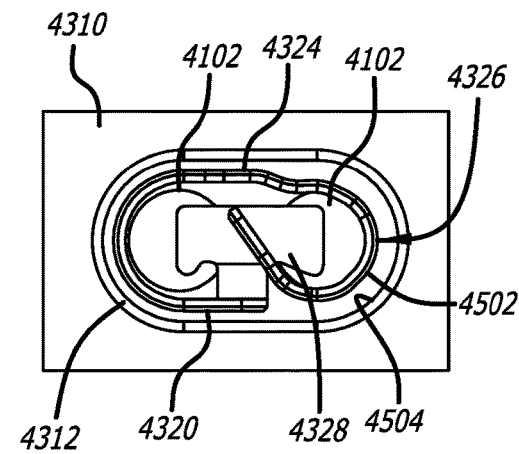
FIG. 48 is a partial top view of the feedthrough assembly of FIG. 41, showing a torsion spring contact with increased clearance between a free side of the contact and an inside wall of a counterbore of a dielectric substrate.

With reference to FIG. 45-48, which show a torsion spring contact 3912 in a free state, the torsion spring contact is sized to provide clearance between the perimeter 4502 of the spring loop 4318 and the inner wall 4504 of the counterbore 4312. In the configuration of FIGS. 47 and 48, the torsion spring contact 3912 is formed to have increased clearance between the free side 4326 of the contact and the inner wall 4504 of the counterbore 4312, relative to the clearance of the configuration of FIGS. 45 and 46. The increased clearance allows the free side 4326 of the torsion spring contact 3912 to be deflected without being obstructed by the walls of the counterbore 4312. The attached side 4322 of the torsion spring contact 3912 do not move significantly and therefore can make a closer fit with the counterbore 4312 to better locate the contact.

With reference to FIGS. 51 and 52, when contact force is applied to the torsion spring contact 3912, for example, while a cover assembly is being secured to a feedthrough assembly, opposed contact forces are applied to the contact engagement feature 4316 and the attachment base 4328. FIG. 51 is an isometric view of the torsion spring contact 3912 with contact force applied, showing deflection of the contact and resulting Von Mises stress. FIG. 52 is a side view of the torsion spring contact 3912 with contact force applied, showing deflection of the contact and resulting Von Mises stress. Defection of the contact primarily occurs at the contact engagement feature 4316 and the free side 4326.

Figure 53:
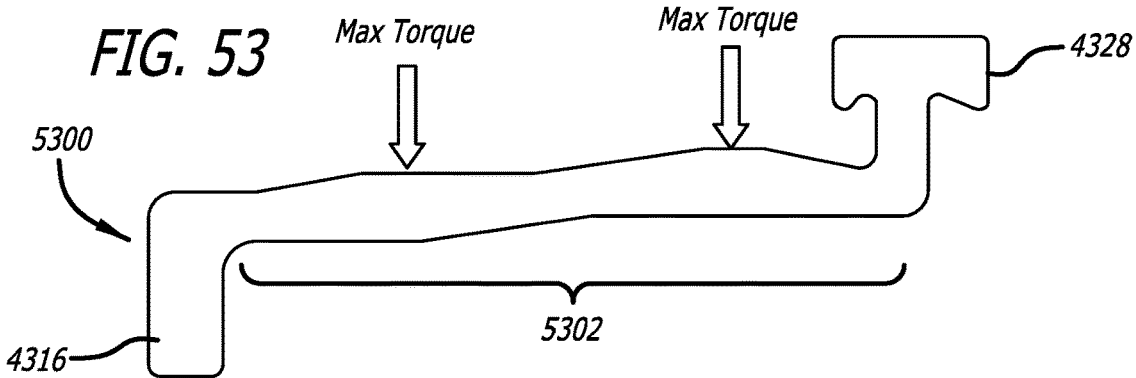
FIG. 53 is an illustration of a contiguous piece of material in a flat pattern and from which the torsion spring contact of FIG. 45 is formed.
Figure 54:
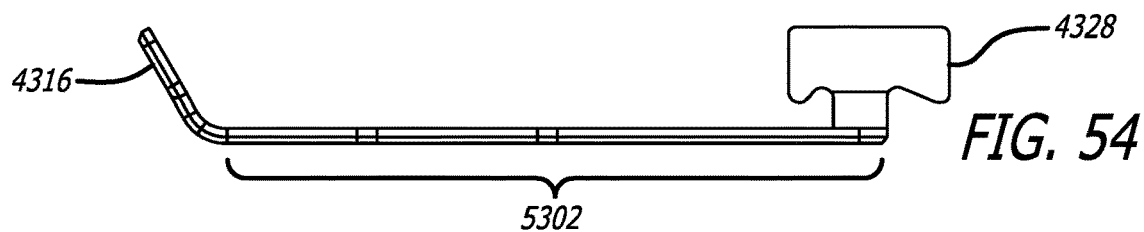
FIG. 54-58 provide visualization of the torsion spring contact forming steps, showing that the two sides of the contact can be formed simultaneously without interference.
Figure 55:
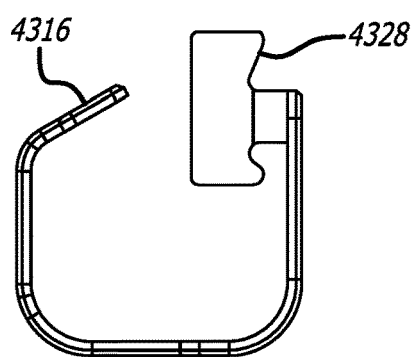
Figure 56:
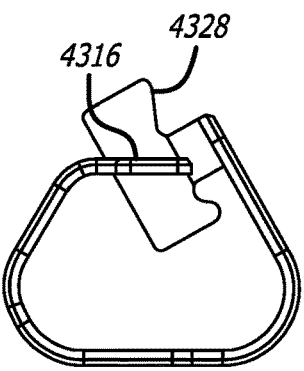
Figure 57:
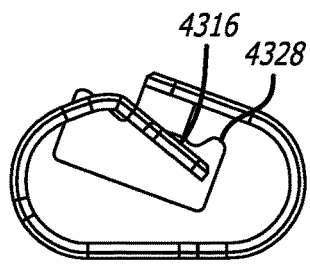
Figure 58:
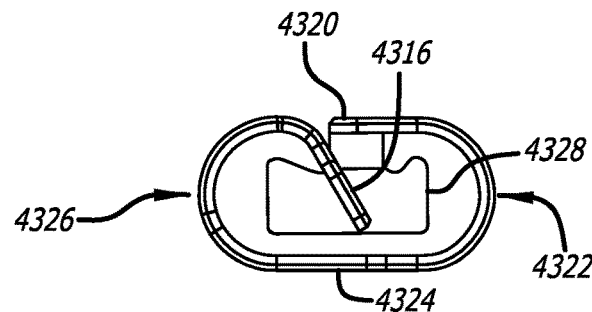

FIG. 53 is an illustration of a contact spring flat pattern 5300, or the blank, wherein the horizontal portion 5302 of the blank from which the spring loop 4318 is formed has a variable cross-sectional width, with wider sections corresponding to higher twisting moment (torque), which optimizes torsion spring contact parameters. FIGS. 54-58 provide visualization of the torsion spring contact forming steps, showing that the two sides of the contact can be formed simultaneously without interference.

With reference to FIGS. 59-62, in some configurations a connector assembly includes a cover assembly and a feedthrough assembly having contacts 5900 configured as torsion spring contact assemblies that attach to conductive via pads 4102 at the bottom surface of counterbores 4312 in a dielectric substrate 4310.

The torsion spring contact assembly 5900 includes a torsion spring 5902 and a weld plate 5904. The torsion spring 5902 comprise a continuous piece of material that is bent, shaped, and formed to include a spring loop 5918 having a free side 5926 and an attached side 5922, and a contact tab or contact engagement feature 5916 that extends from the free side. An attachment feature 5906, referred to as an attachment end, is included in the attached side 5922. The spring loop 5918 has a perimeter with a shape corresponding to the perimeter shape of the counterbores 4312 and is sized to fit within the counterbore. In the configuration of FIGS. 59-62, the perimeter shape of the counterbore 4312 and the spring loop 5918 is a discorectangle, i.e., a geometric shape consisting of a rectangle with top and bottom lengths whose ends are capped off with semicircles of radius. Other shapes, however, are possible.

The attachment end 5906 of the torsion spring 5902 is electrically coupled to the weld plate 5904. To this end, the weld plate 5904 include a slot 5908 into which the attachment end 5906 fits and is secured in place, for example, by welding. With reference to FIGS. 61 and 62, the weld plate 5904 is shaped to fit within and locate the torsion spring contact assembly 5900 in a counterbore 4312 of a feedthrough substrate to assure optimum operating clearance for the torsion spring contact. There is a close fit of the weld plate 5904 in the counterbore 4312, and a larger clearance between the free side 5926 of the torsion spring 5902 and the side walls of the counterbore.

Figure 63:
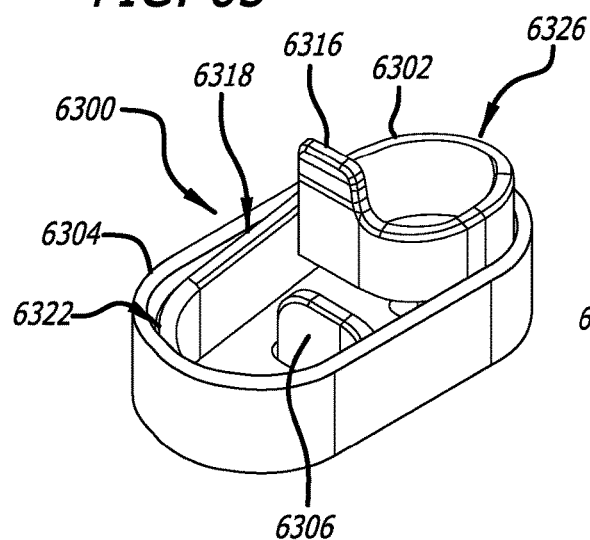
FIG. 63-64 is an illustration of another contact configured as a torsion spring contact assembly that includes a torsion spring contact and a protective shroud.
Figure 64:
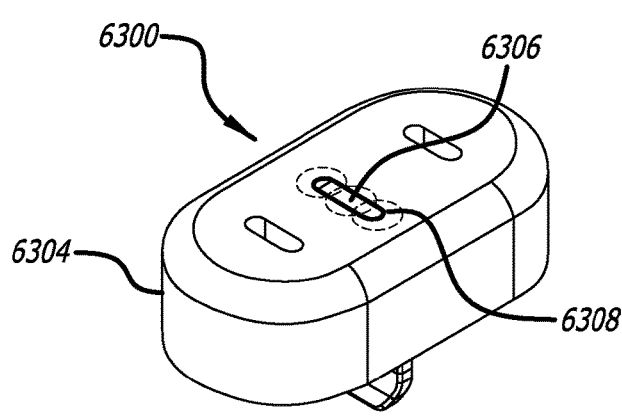
Figure 65:
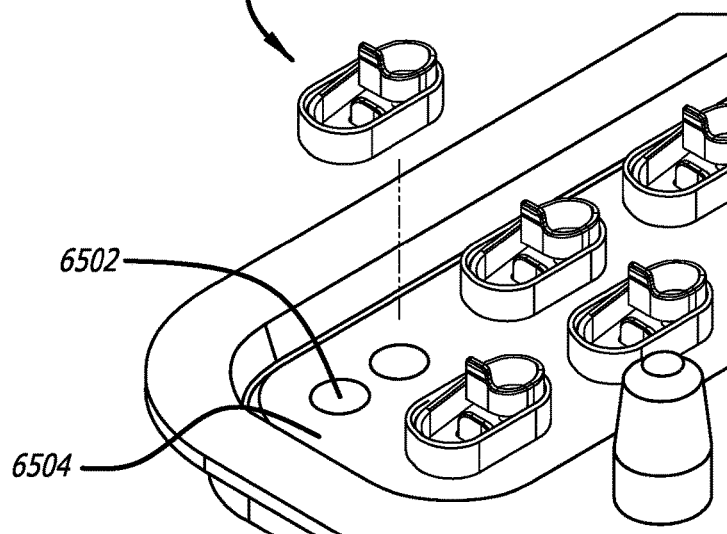
FIG. 65 is a partial perspective view of a feedthrough assembly with the torsion spring contact assembly of FIG. 63 raised above a dielectric substrate of the feedthrough assembly.

With reference to FIGS. 63-65, in some configurations a connector assembly includes a cover assembly and a feedthrough assembly having contacts 6300 configured as torsion spring contact assemblies that attach to conductive via pads 6502 on a surface a dielectric substrate 6504.

The torsion spring contact assembly 6300 includes a torsion spring 6302 and a protective shroud 6304. The torsion spring 6302 comprise a continuous piece of material that is bent, shaped, and formed to include a spring loop 6318 having a free side 6326 and an attached side 6322, and a contact tab or contact engagement feature 6316 that extends from the free side. An attachment feature 6306, referred to as an attachment end, is included in the attached side 6322. The spring loop 6318 has a perimeter with a shape corresponding to the perimeter shape of the protective shroud 6304 and is sized to fit within the shroud. In the configuration of FIGS. 59-62, the perimeter shape of the protective shroud 6304 and the spring loop 6318 is a discorectangle, i.e., a geometric shape consisting of a rectangle with top and bottom lengths whose ends are capped off with semicircles of radius. Other shapes, however, are possible.

The attachment end 6306 of the torsion spring 6302 is electrically coupled to the protective shroud 6304. To this end, the protective shroud 6304 include a slot 6308 into which the attachment end 6306 fits and is secured in place, for example, by welding. With reference to FIG. 65, the protective shroud 6304 of the torsion spring contact assembly 6300 is welded to conductive via pads 6502 that are co-planar with the top surface of the dielectric substrate 6504.

Figure 66:
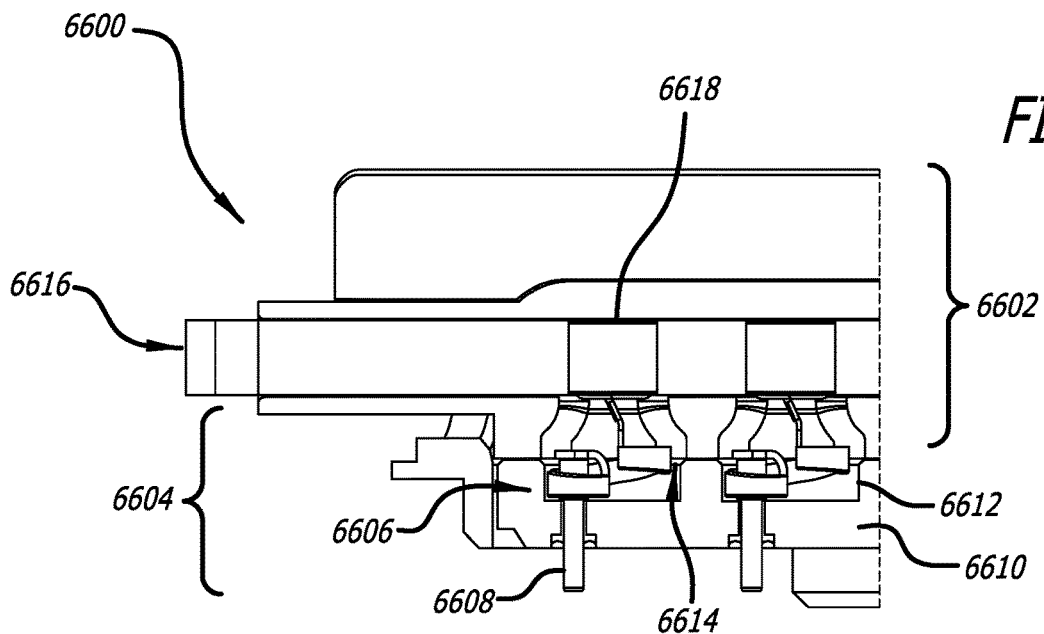
FIG. 66 is a cross-sectional view of a connector assembly taken along a lead when a cover assembly is coupled to, but not fully seated with a feedthrough assembly having contacts configured as torsion spring contacts attached to feedthrough pins.
Figure 67:
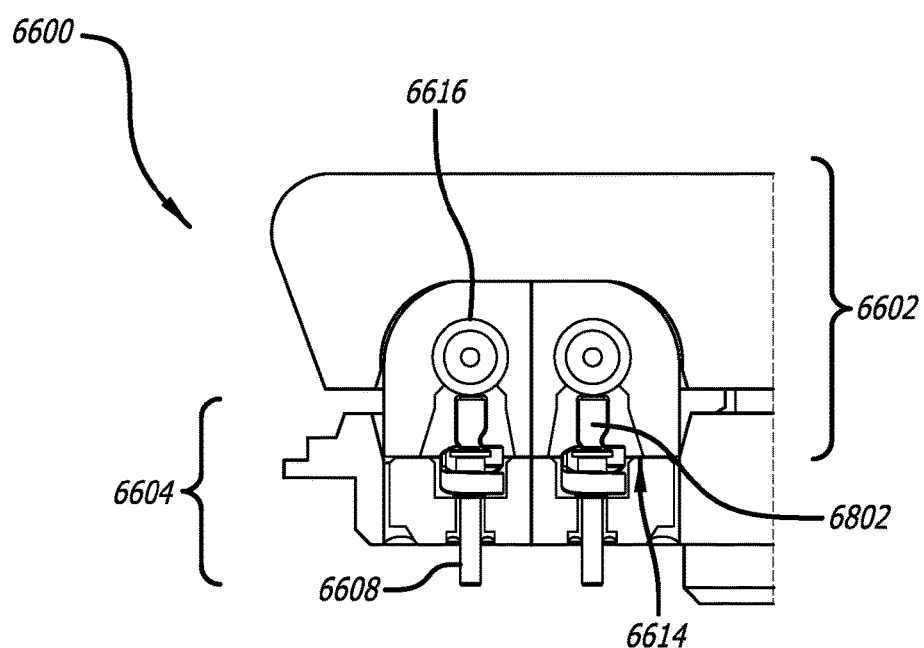
FIG. 67 is a cross-sectional view of the connector assembly of FIG. 66 taken at a right angle to a pair of leads when a cover assembly is coupled to, but not fully seated with a feedthrough assembly.
Figure 72:
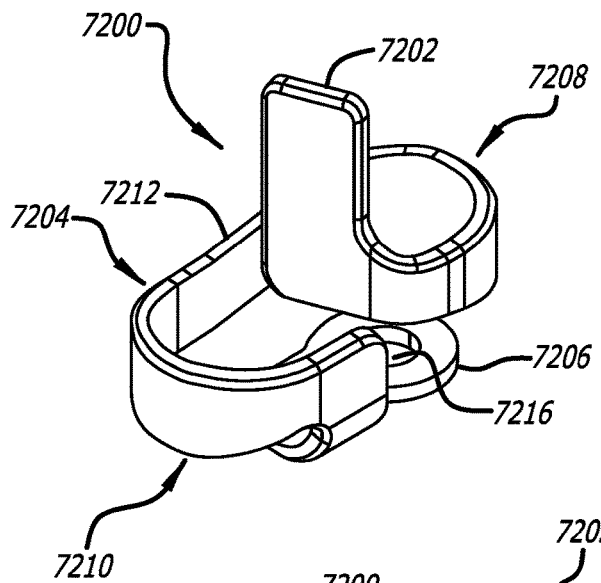
FIGS. 72-75 are illustrations of another contact configured as a torsion spring contact configured to occupy a counterbore in a dielectric substrate and to attach to a feedthrough pin at the bottom of the counterbore.
Figure 73:
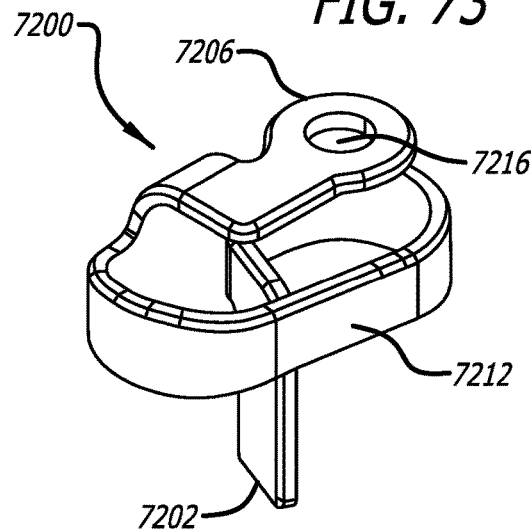
Figure 74:
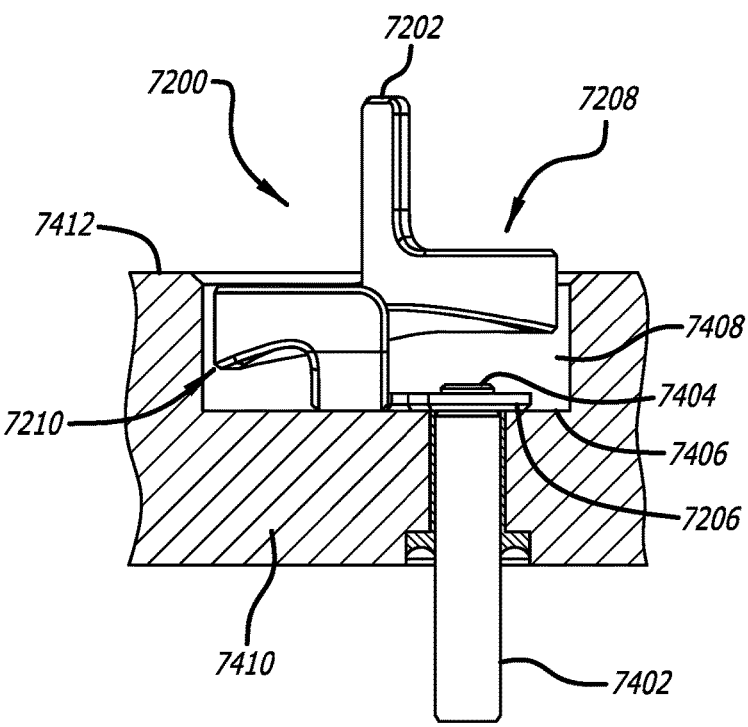
Figure 75:
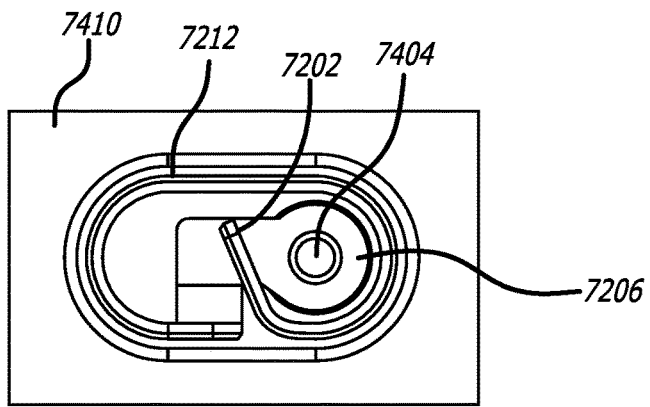
Figure 76:
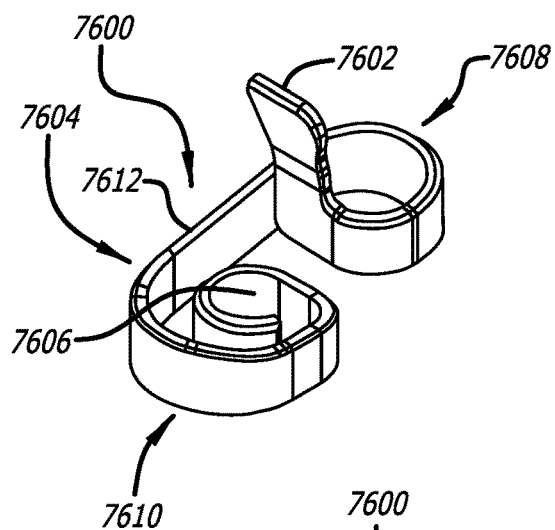
FIGS. 76-79 are illustrations of another contact configured as a torsion spring contact configured to occupy a counterbore in a dielectric substrate and to attach to a feedthrough pin that extends upward from the bottom of the counterbore.
Figure 77:
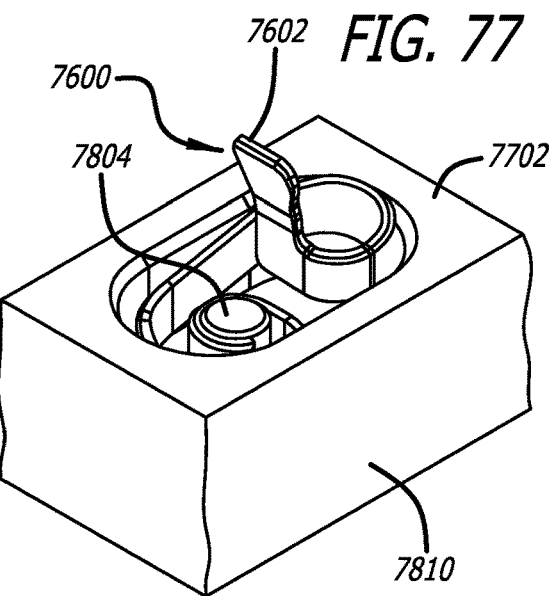
Figure 78:
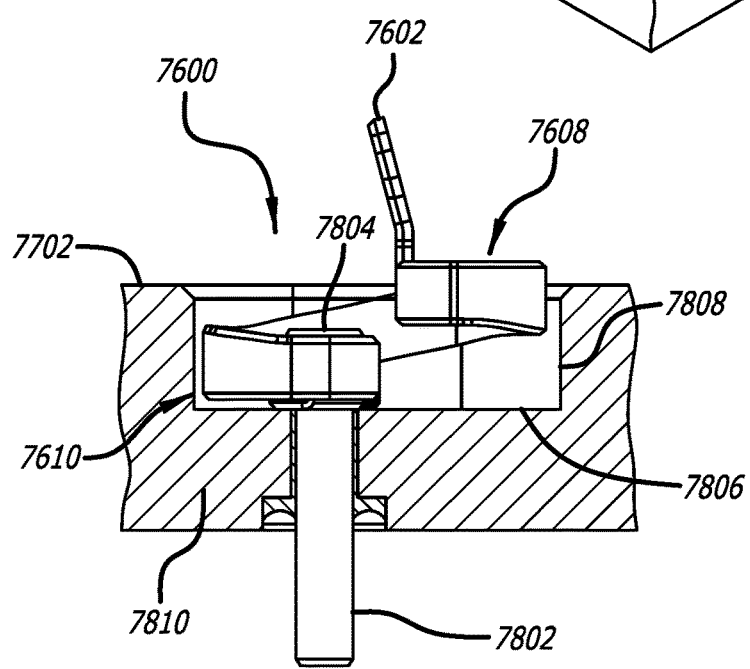
Figure 79:
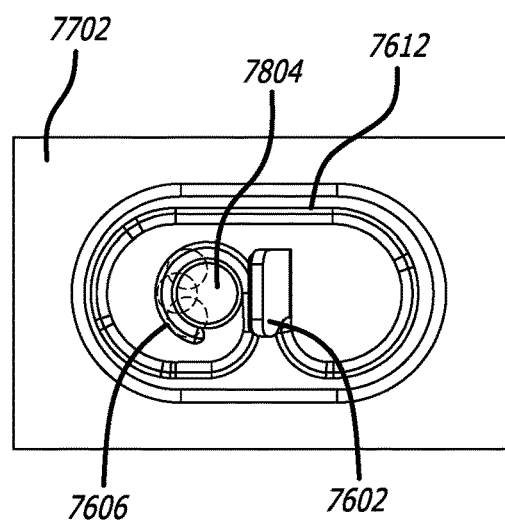

With reference to FIGS. 66-71, in some embodiments a connector assembly 6600 of an implantable medical device includes a cover assembly 6602 and a feedthrough assembly 6604 configured to couple with the cover assembly. The cover assembly 6602 is configured to receive a connector end of a lead 6616 having lead contacts 6618, and to align the lead contacts with apertures 6614 of the cover assembly 6602. The feedthrough assembly 6604 includes feedthrough contacts 6620 in the form of the tips of feedthrough pins 6608 that extend into counterbores 6612 of a feedthrough substrate 6610. As shown in FIGS. 66 and 67, attached electrical contacts 6606 configured as torsion spring contacts are attached to the feedthrough contacts 6620 and are located in the apertures 6614 when the cover assembly 6602 and feedthrough assembly 6604 are coupled. With reference to FIG. 69, each of the attached electrical contacts 6606 includes an attachment feature 6806 permanently coupled to a feedthrough contact 6620 and a contact engagement feature 6802 positioned in an aperture 6614.

With reference to FIGS. 68-71, these torsion spring contact assemblies 6606 comprise a continuous piece of material that is bent, shaped, and formed to include a spring loop 6804 having a free side 6814 and an attached side 6810, and a contact engagement feature 6802 that extends from the free side. An attachment tab 6806 is included in the attached side 6810. The spring loop 6804 has a perimeter with a shape corresponding to the perimeter shape of the counterbores 6612 and is sized to fit within a counterbore. The perimeter shape of the counterbore 6612 and the spring loop 6804 is a discorectangle, i.e., a geometric shape consisting of a rectangle with top and bottom lengths whose ends are capped off with semicircles of radius. Other shapes, however, are possible.

The spring loop 6804 is open (does not form a continuous or closed geometric shape) and includes a spiral portion that extends from the attachment tab 6806. The spiral portion spirals from a first semicircular radius of the attached side 6810, through a linear side 6812, through a second semicircular radius of the free side 6814, and terminates at the contact engagement feature 6802. The contact engagement feature 6802 projects upward relative to the spring loop 6804 and in a direction of an aperture 6614 of the cover assembly 6602. This formation of a torsion spring contact 6606 places the edge of the contact engagement feature 6802 at a location above the top surface of the feedthrough substrate 6610. The attachment tab 6806 includes a through hole 6816 sized to receive the tip of a feedthrough pin 6608. The torsion spring contacts 6606 are electrically coupled to the feedthrough contacts 6620 through the attachment tab 6806.

The feedthrough pins 6608 aid in positioning of the torsion spring contacts 6606 within the counterbores 6612 and can help to bias the position of the torsion spring contacts in a manner that increases the clearance between the free side 6814 of the contacts and the inner wall of the counterbores 6612 of the feedthrough substrate 6610.

With reference to FIGS. 72-75, in some configurations a connector assembly includes a cover assembly and a feedthrough assembly having contacts 7200 configured as torsion spring contacts that attach to feedthrough pins 7402 with tips 7404 that terminate at or near the bottom surface 7406 of counterbores 7408 in a feedthrough substrate 7410.

These torsion spring contacts 7200 comprise a continuous piece of material that is bent, shaped, and formed to include a spring loop 7204 having a free side 7208 and an attached side 7210, and a contact tab or contact engagement feature 7202 that extends from the free side. An attachment tab 7206 is included in the attached side 7210. The spring loop 7204 has a perimeter with a shape corresponding to the perimeter shape of the counterbores 7408 and is sized to fit within a counterbore 7408. The perimeter shape of the counterbore 7408 and the spring loop 7204 is a discorectangle, i.e., a geometric shape consisting of a rectangle with top and bottom lengths whose ends are capped off with semicircles of radius. Other shapes, however, are possible.

The spring loop 7204 is open (does not form a continuous or closed geometric shape) and includes a spiral portion that extends from the attachment tab 7206. The spiral portion spirals from a first semicircular radius of the attached side 7210, through a linear side 7212, through a second semicircular radius of the free side 7208, and terminates at the contact engagement feature 7202. The contact engagement feature 7202 projects upward relative to the spring loop 7204 and in a direction of an aperture of the cover assembly. This formation of a torsion spring contact 7200 places the contact engagement feature 7202 at a location above the top surface 7412 of the feedthrough substrate 7410. The attachment tab 7206 includes a through hole 7216 sized to receive the tip 7404 of a feedthrough pin 7402. The torsion spring contacts 7200 are electrically coupled to the tips 7404 of the feedthrough pins 7402 through the attachment tab 7206.

The feedthrough pins 7402 aid in positioning of the torsion spring contacts 7200 within the counterbores 7408 and can help to bias the position of the torsion spring contact assemblies in a manner that increases the clearance between the free side 7208 of the contacts and the inner wall of the counterbores 7408 of the feedthrough substrate 7410.

With reference to FIGS. 76-79, in some configurations a connector assembly includes a cover assembly and a feedthrough assembly having contacts 7600 configured as torsion spring contacts that attach to feedthrough pins 7802 with tips 7804 that terminate at or near the middle of counterbores 7808 in a substrate 7810.

These torsion spring contacts 7600 comprise a continuous piece of material that is bent, shaped, and formed to include a spring loop 7604 having a free side 7608 and an attached side 7610, and a contact tab or contact engagement feature 7602 that extends from the free side. An attachment feature in the form of a curled sleeve 7606 is included in the attached side 7610. The spring loop 7604 has a perimeter with a shape corresponding to the perimeter shape of the counterbores 7808 and is sized to fit within a counterbore. The perimeter shape of the counterbore 7808 and the spring loop 7604 is a discorectangle, i.e., a geometric shape consisting of a rectangle with top and bottom lengths whose ends are capped off with semicircles of radius. Other shapes, however, are possible.

The spring loop 7604 is open (does not form a continuous or closed geometric shape) and includes a spiral portion that extends from the curled sleeve 7606. The spiral portion spirals from a first semicircular radius of the attached side 7610, through a linear side 7612, through a second semicircular radius of the free side 7608, and terminates at the contact engagement feature 7602. The contact engagement feature 7602 projects upward relative to the spring loop 7604 and in a direction of an aperture of the cover assembly. This formation of a torsion spring contact 7600 places the contact engagement feature 7602 at a location above the top surface 7702 of the feedthrough substrate 7810. The curled sleeve 7606 is sized to receive the tip 7804 of a feedthrough pin 7802. The torsion spring contacts 7600 are electrically coupled to the tips 7804 of the feedthrough pins 7802 through the curled sleeve 7606.

The feedthrough pins 7802 aid in positioning of the torsion spring contacts 7600 within the counterbores 7808 and can help to bias the position of the torsion spring contacts in a manner that increases the clearance between the free side 7608 of the contacts and the inner wall of the counterbores 7808 of the feedthrough substrate 7810.

With reference to FIGS. 80-83, in some configurations a connector assembly includes a cover assembly and a feedthrough assembly having contacts 8000 configured as torsion spring contacts that attach to feedthrough pins 8102 with tips 8104 that terminate above a top surface 8112 a feedthrough substrate 8110.

These torsion spring contacts 8000 comprise a continuous piece of material that is bent, shaped, and formed to include a spring loop 8004 having a free side 8008 and an attached side 8010, and a contact tab or contact engagement feature 8002 that extends from the free side. An attachment feature in the form of a curled sleeve 8006 is included in the attached side 8010. The spring loop 8004 has a perimeter with a shape corresponding to the perimeter shape of the counterbores 8108 and is sized to fit within a counterbore. The perimeter shape of the counterbore 8108 and the spring loop 8004 is a discorectangle, i.e., a geometric shape consisting of a rectangle with top and bottom lengths whose ends are capped off with semicircles of radius. Other shapes, however, are possible.

The spring loop 8004 is open (does not form a continuous or closed geometric shape) and includes a spiral portion beneath the curled sleeve 8006. The spiral portion spirals from a first semicircular radius of the attached side 8010, through a linear side 8012, through a second semicircular radius of the free side 8008, and terminates at the contact engagement feature 8002. The contact engagement feature 8002 projects upward relative to the spring loop 8004 and in a direction of an aperture of the cover assembly. This formation of a torsion spring contact 8000 places the contact engagement feature 8002 at a location above the top surface 8112 of the feedthrough substrate 8110. The curled sleeve 8006 is sized to receive the tip 8104 of a feedthrough pin 8102. The torsion spring contacts 8000 are electrically coupled to the feedthrough pins 8102 through the curled sleeve 8006.

The feedthrough pins 8102 aid in positioning of the torsion spring contacts 8000 within the counterbores 8108 and can help to bias the position of the torsion spring contacts in a manner that increases the clearance between the free side 8008 of the contacts and the inner wall of the counterbores 8108 of the feedthrough substrate 8110.

II. Contacts Associated with Cover Assembly

In some embodiment, detached contacts may be included in the cover assembly component of a connector assembly instead of the feedthrough assembly as disclosed above. These detached contacts are "interposed" between an implantable lead and the implantable device's feedthrough assembly, and form pressure connections between lead contacts and respective feedthrough substrates. The detached contacts are protectively retained in the apertures of the seal, which seal is pre-attached to the cover of the cover assembly.

With reference to FIGS. 84-91, a connector assembly 8400 of an implantable medical device includes a cover assembly 8402 and a feedthrough assembly 8404 configured to couple with the cover assembly. The cover assembly 8402 is configured to receive a connector end of a lead 8408 having lead contacts 8410, and to align the lead contacts with pockets or apertures 8414 of the cover assembly. The feedthrough assembly 8404 may include feedthrough contacts 8416 in the form of conductive vias on the surface of the feedthrough substrate 8420. Electrical contacts 8412 configured as leaf spring contacts are retained by, but not permanently attached to, the cover assembly 8402. With reference to FIGS. 87-91, when the cover assembly 8402 and feedthrough assembly 8404 are coupled, first surfaces 8602, 8604 of the electrical contacts 8412 face the feedthrough contacts 8416 and at least one second surface 8606 of the contacts is positioned in the pockets or apertures 8414 of the cover assembly. Upon complete seating of the cover assembly 8402 and feedthrough assembly 8404, the first surfaces 8602, 8604 and second surface 8606 of the electrical contacts are respectively compressed into contact with the feedthrough contacts 8416 and the lead contacts 8410.

Figure 85:
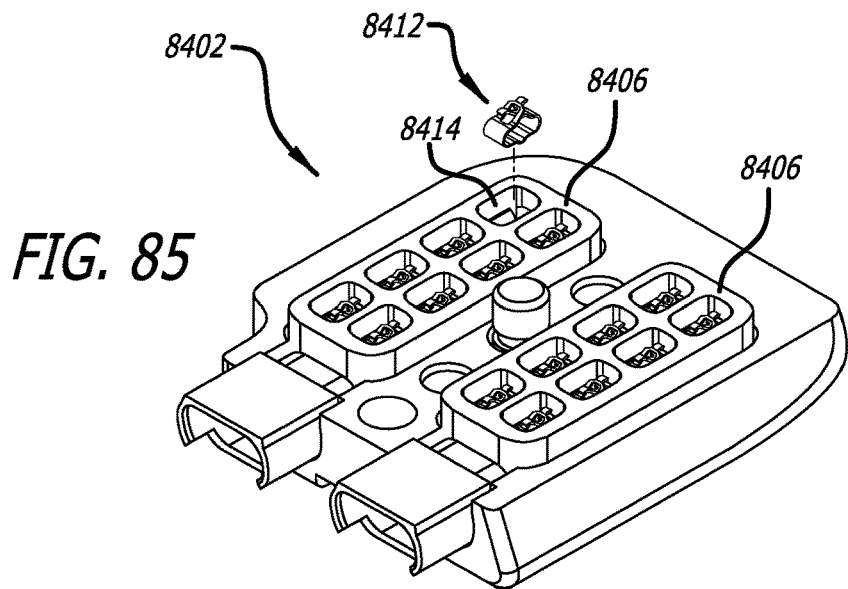

With reference to FIGS. 84 and 85, the cover assembly 8402 includes a pair of seals 8406, each configured to receive a connector end of a lead 8408 that carries a number of lead contacts 8410. The seals 8406 include an array of pockets or apertures 8414 each configured to retain a leaf spring contact 8412 configured as a leaf spring contact. The leaf spring contacts 8412 provide electrical connections between the lead contacts 8410 and conductive vias 8416 that extend through the feedthrough assembly. In the configuration of FIG. 85, there are four rows of leaf spring contacts 8412, with each row having four contacts.

Figure 86A:
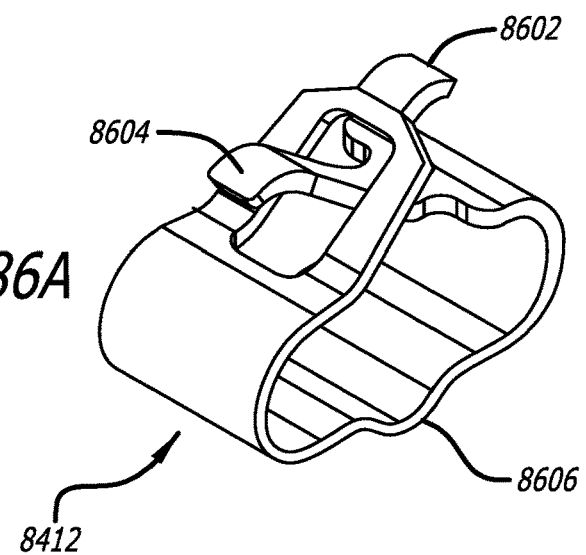
FIGS. 86A and 86B are an enlarged views of the leaf spring contact of FIG. 85 from different perspectives.
Figure 86B:
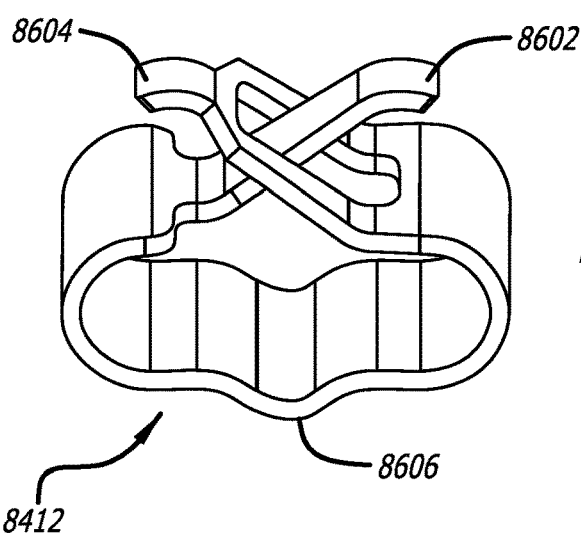

With reference to FIGS. 86A and 86B, in some embodiments the leaf spring contacts 8412 comprise a continuous piece of flat material bent, shaped, and formed to include overlapping tines, each corresponding to a first surface 8602, 8604, and a rounded tip corresponding to a second surface 8606. The first surfaces 8602, 8604 are configured to couple with a pair of conductive vias 8416 of the feedthrough assembly 8404. The rounded second surface 8606 is configured to couple with a lead contact 8410.

Figure 87:
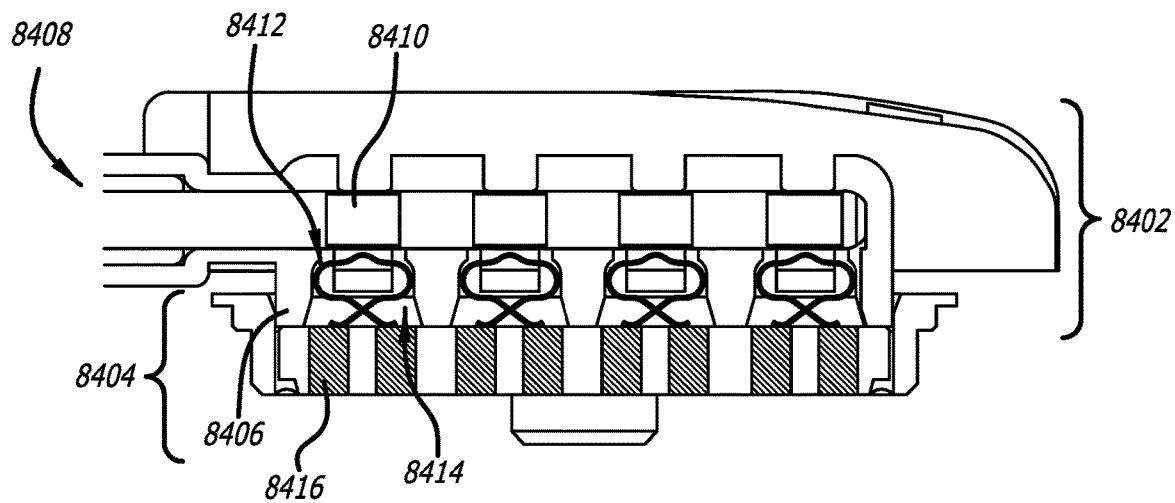
FIG. 87 is a cross-sectional view of the connector assembly of FIG. 84 with the cover assembly coupled to the feedthrough assembly, but not fully seated.
Figure 88:
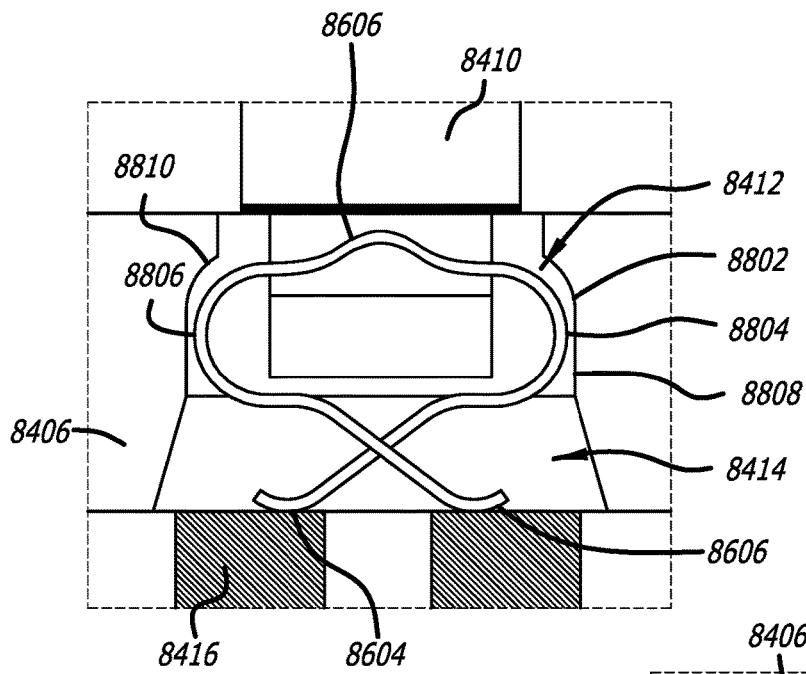
FIG. 88 is a detail view of a portion of FIG. 87.
Figure 89:
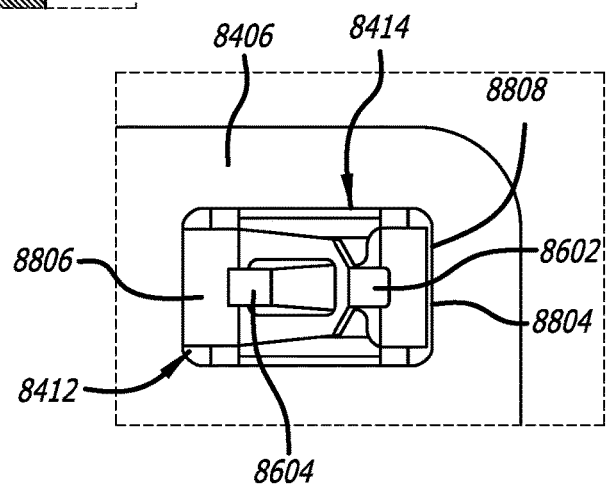
FIG. 89 is a detailed plan view of a leaf spring contact retained by the cover assembly of FIG. 85.

In FIGS. 87-89, because the cover assembly 8402 and the feedthrough assembly 3904 are not fully secured to each other, the leaf spring contacts 8412 are not fully compressed between the lead contacts 8410 and the conductive vias 8416. Furthermore, there is a clearance 8802 between sides 8804, 8806 of the leaf spring contacts 8412 and the side walls 8808, 8810 of the aperture 8414. This clearance 8802 accommodate expansion of the leaf spring contacts 8412 when the connector assembly is pressurized (i.e., when the cover assembly is fully seated with the feedthrough assembly). This uncompressed state (or undeflected state) of the leaf spring contacts 8412 may be referred to as a free state or an unpressurized state. In this state, the leaf spring contacts 8412 are not tightly secured between the lead contacts 8410 and the conductive vias 8416 and may slide and move around within the apertures 8414.

Figure 90:
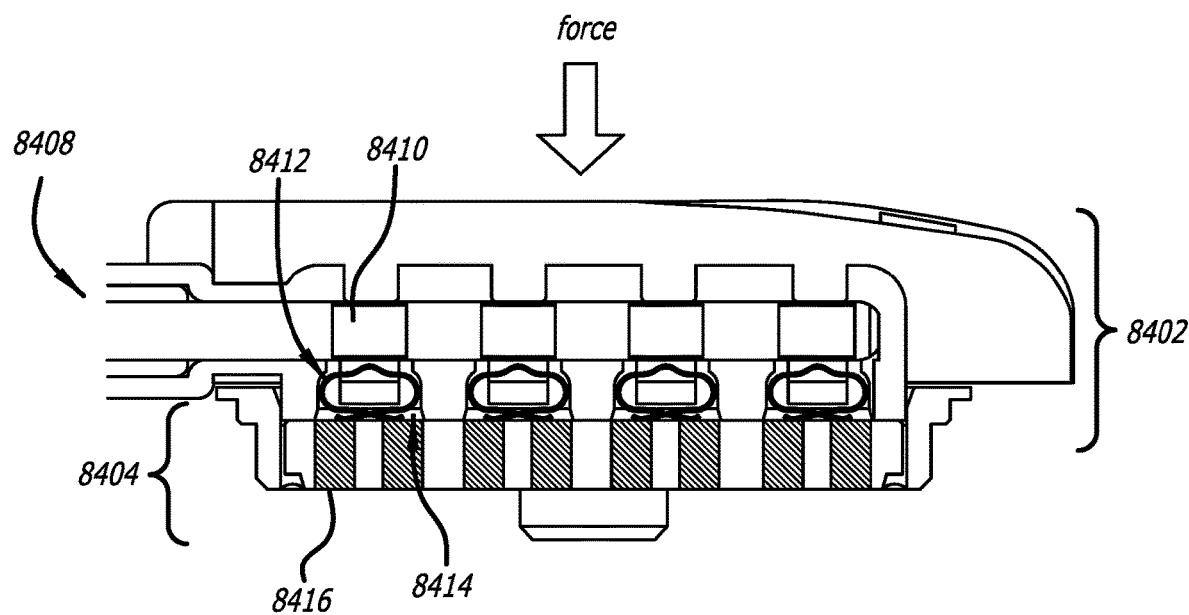
FIG. 90 is a cross-sectional view of the connector assembly of FIG. 84 with the cover assembly coupled to the feedthrough assembly, and fully seated.
Figure 91:
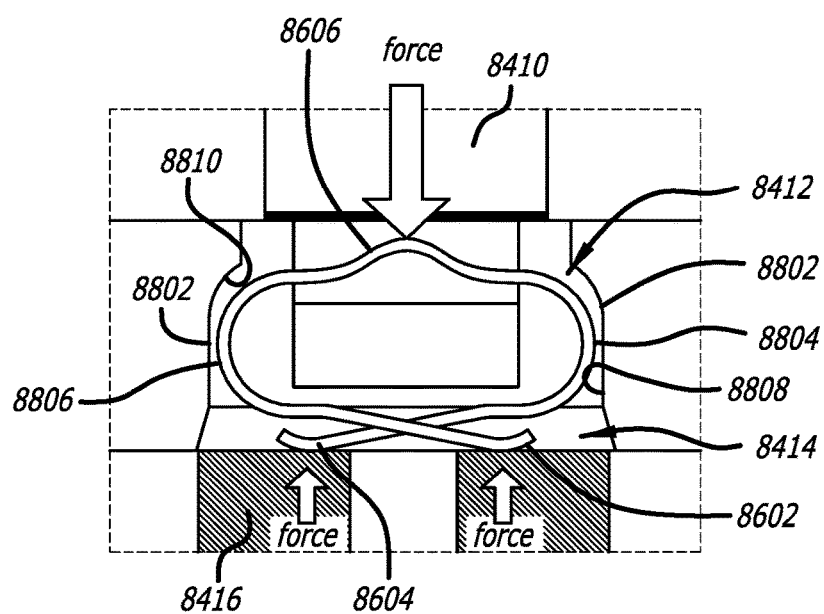
FIG. 91 is a detail view of a portion of FIG. 90.

In FIGS. 90 and 91, because the cover assembly 8402 and the feedthrough assembly 3904 are fully secured to each other by tightening of a screw (not shown) of the cover assembly, the leaf spring contacts 8412 are fully compressed between the lead contacts 8410 and the conductive vias 8416. This compressed state (or deflected state) of the leaf spring contacts 8412 may be referred to as a pressurized state. In this state, contact forces exerted on the leaf spring contacts 8412 cause the contacts to compress vertically between lead contacts 8410 and the conductive vias 8416, as indicated by the vertical arrows, and to deflect or expand horizontally, as indicated by the horizontal arrows. Once fully compressed and deflected, the leaf spring contacts 8412 are tightly secured between the lead contacts 8410 and the conductive vias 8416. The clearance 8802 between the sides 8804, 8806 of the leaf spring contact 8412 and the side walls 8808, 8810 of the aperture 8414 remain after compression because the semi-circular sides of the contact do not expand when the contact is deflected.

Figure 92:
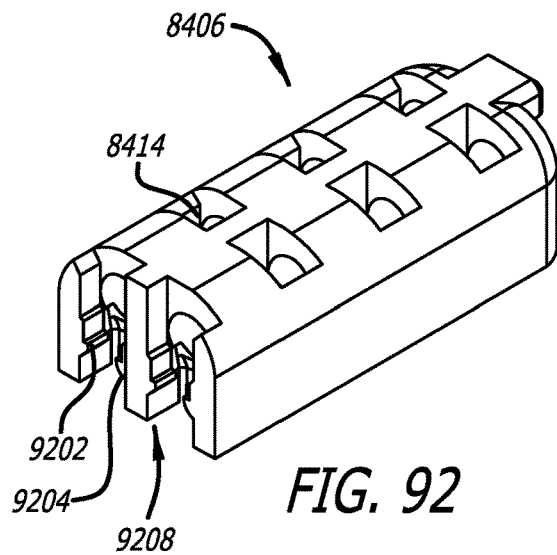
FIG. 92 is a perspective cross-sectional view of a dual-lumen seal of the cover assembly of FIGS. 84 and 85, taken across seal apertures, to reveal contact retention ledges.
Figure 93:
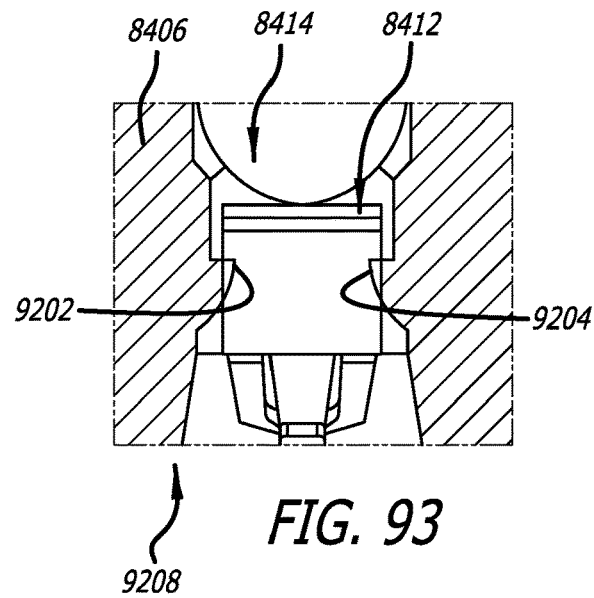
FIG. 93 is a detailed cross-sectional view of the seal of FIG. 92 revealing a retained leaf spring contact.
Figure 94:
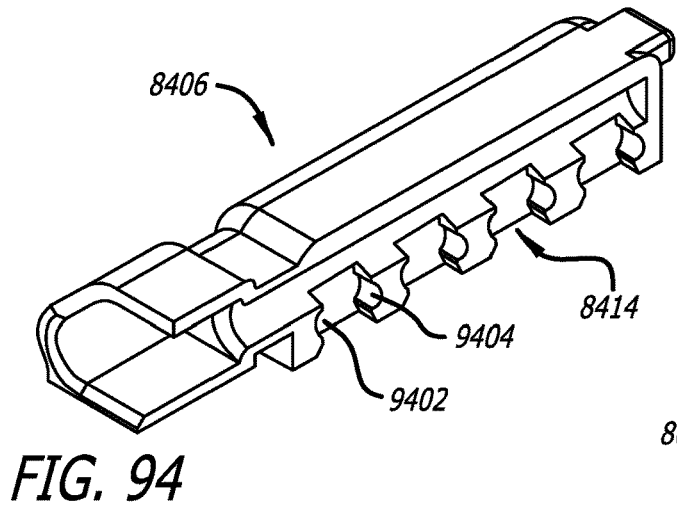
FIG. 94 is a perspective cross-sectional view of a dual-lumen seal, taken along seal apertures, to reveal concave contact retention features.
Figure 95:
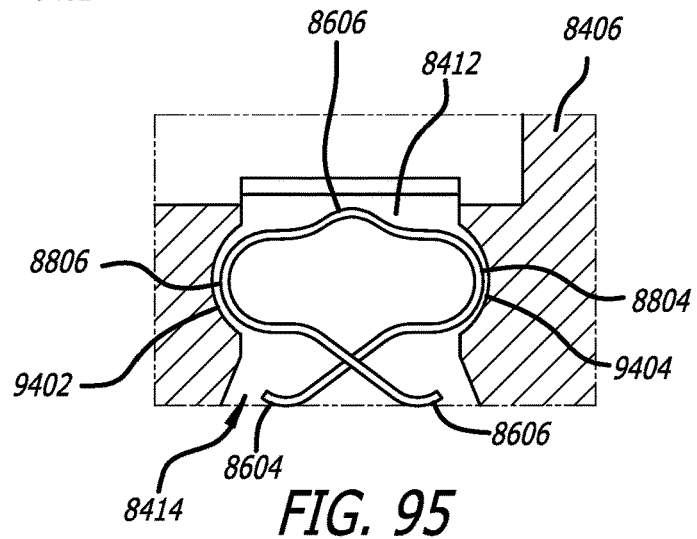
FIG. 95 is a detailed cross-sectional view of the seal of FIG. 94, with a leaf spring contact snapped in place from the feedthrough side of the seal, and retained by the seal's concave contact retention features.

With reference to FIGS. 92 and 93, the seals 8406 of the cover assembly 8402 includes a pair of ledges 9202, 9204 having a tapered cross-section. With reference to FIGS. 94 and 95, the seals 8406 of the cover assembly 8402 also includes a pair of concave recesses 9402, 9404 having a contour generally corresponding to the curvature of the sides 8804, 8806 of the leaf spring contact 8412. The ledges 9202, 9204 and the concave recesses 9402, 9404 function to retain the leaf spring contact 8412 within the aperture 8414. To this end, the seals 8406 are formed of a material, e.g., elastomeric material such as silicone, that enables the leaf spring contact 8412 to be snapped in place from the feedthrough side 9208 of the seal, and retained by the ledges 9202, 9204 and the concave recesses 9402, 9404.

Figure 96:
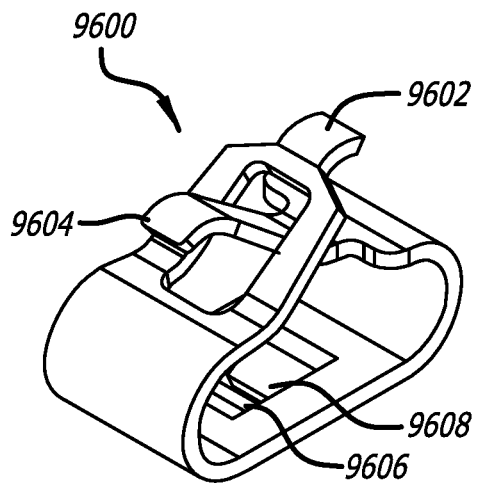
FIGS. 96-99 are various embodiments of leaf spring contacts that may be used in the connector assembly of FIGS. 84 and 85.
Figure 97:
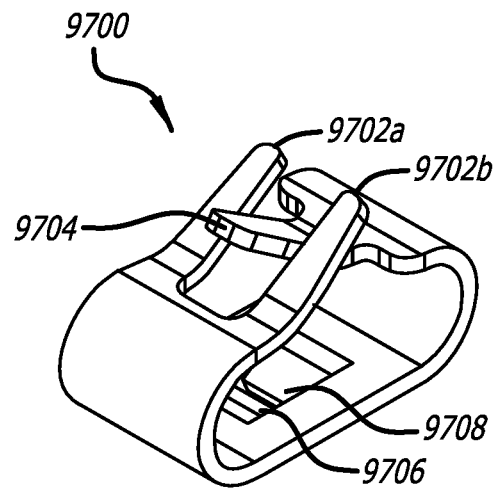

With reference to FIGS. 96-99, the leaf spring contact 8412 may have anyone of several different configurations. In FIG. 96, the leaf spring contact 9600 has first surfaces 9602, 9604 corresponding to formed contact tips on the side of the contact that faces the feedthrough assembly, and second surfaces 9606, 9608 corresponding to sheared contact tips on the side of the contact that faces the lead contacts. In FIG. 97, the leaf spring contact 9700 is a lower profile contact that has first surfaces 9702a, 9702b, 9704 corresponding to end tines on the side of the contact that faces the feedthrough assembly, and second surfaces 9706, 9708 corresponding to sheared contact tips on the side of the contact that faces the lead contacts. The first surfaces 9702a, 9702b, 9704 are three overlapping end tines that bypass each other and do not interfere with the opposite side of the contact when the contact is fully compressed.

Figure 98:
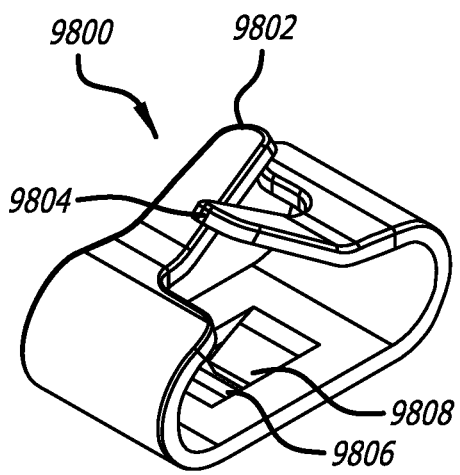
Figure 99:
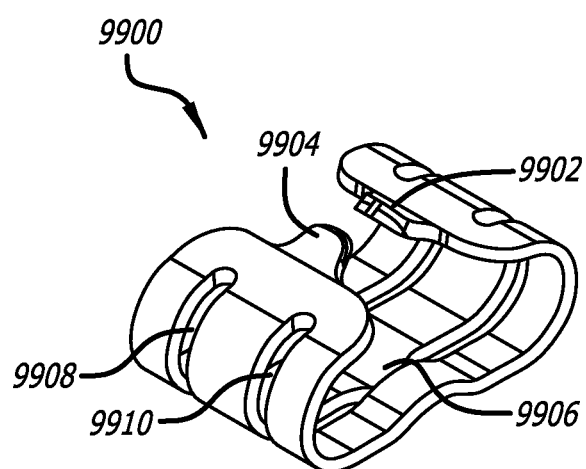

In FIG. 98, the leaf spring contact 9800 is a lower profile contact that has first surfaces 9802, 9804 corresponding to end tines on the side of the contact that faces the feedthrough assembly, and second surfaces 9806, 9808 corresponding to sheared contact tips on the side of the contact that faces the lead contacts. The first surfaces 9802, 9804 are two overlapping end tines that bypass each other and do not interfere with the opposite side of the contact when the contact is fully compressed. In FIG. 99, the leaf spring contact 9900 is a lower profile contact that has first surfaces 9902, 9904 corresponding to contact tips on the side of the contact that faces the feedthrough assembly, and a second surface 9906 corresponding to a rounded tip on the side of the contact that faces the lead contacts. The leaf spring contact 9900 has multiple lengthwise slits 9908, 9910 which increase deflection compliance of the contact.

Figure 100:
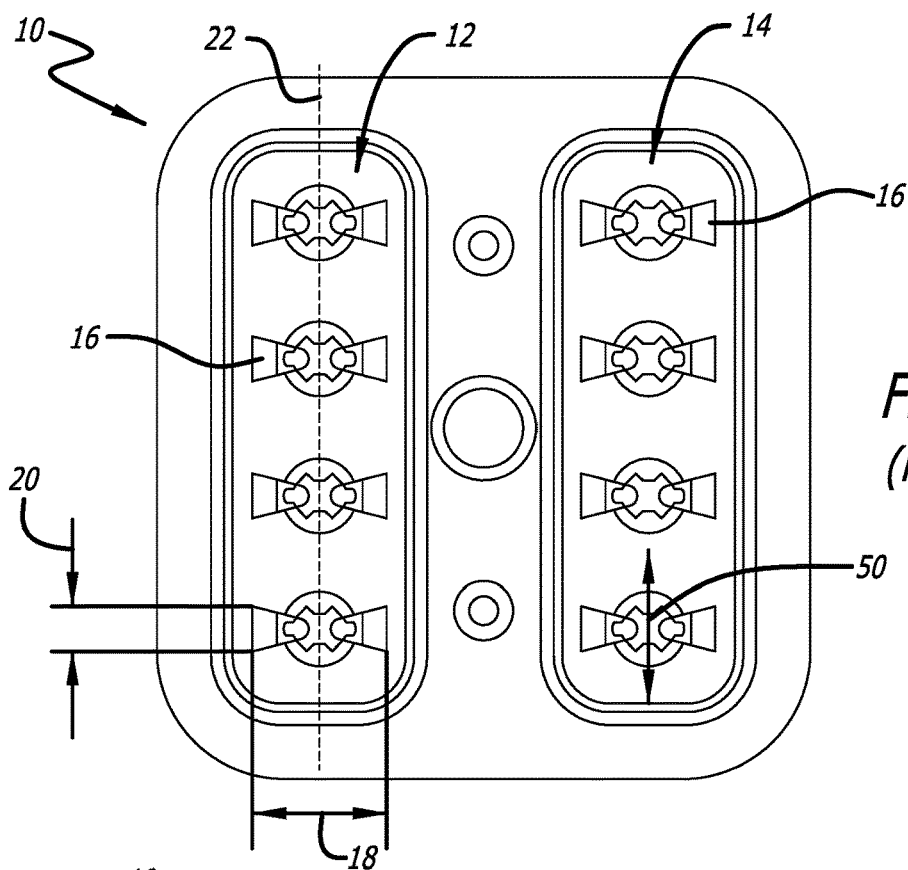
FIG. 100 is a plan view illustration of a conventional feedthrough assembly that accommodates two leads.
Figure 101:
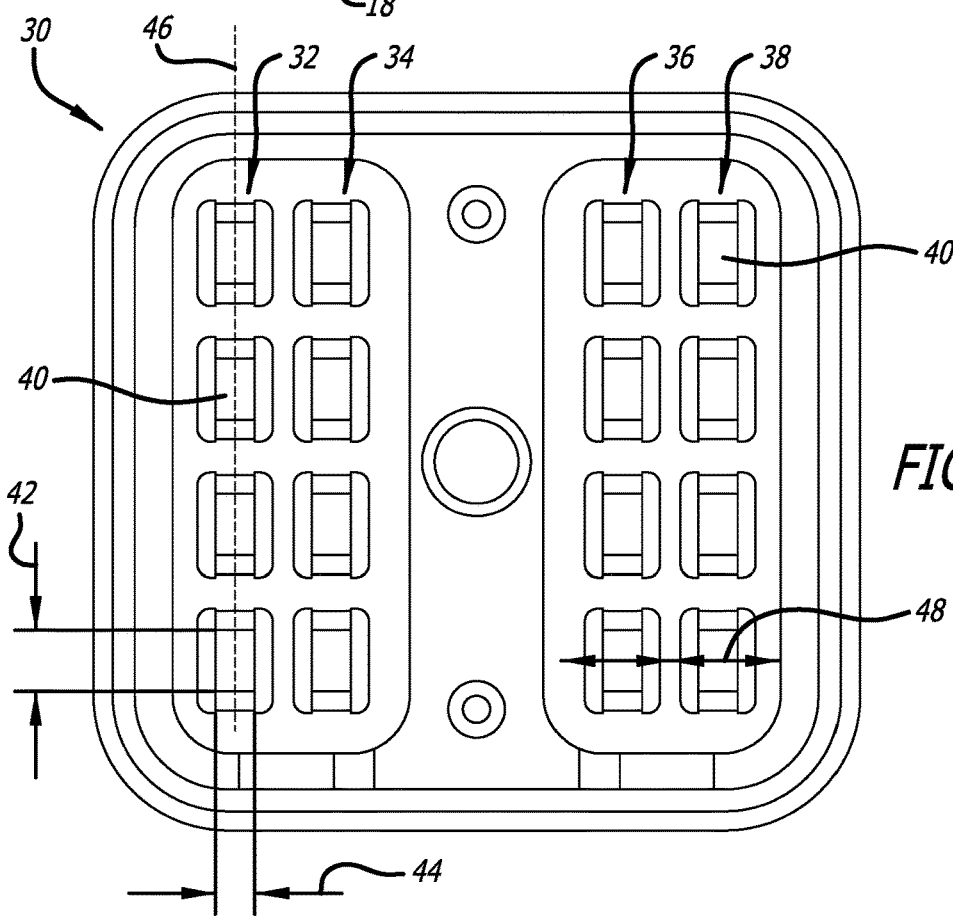
FIG. 101 is a plan view illustration of a feedthrough assembly disclosed herein that that accommodates four leads in about the same amount of space as the conventional feedthrough assembly of FIG. 100.

III. Comparison to Conventional Connector Assemblies:

A benefit of the connector assemblies disclosed herein is the enabling of a higher density of electrical connections between an implantable medical device and lead contacts. With reference to FIGS. 100 and 101, the connector assemblies disclosed herein allow for more leads to be connected to a medical device without having to expand the physical size of the medical device.

With reference to FIG. 100, a conventional connector assembly having a feedthrough assembly 10 such as disclosed in U.S. Pat. No. 6,662,035 can accommodate two leads. The feedthrough assembly 10 includes two lines 12, 14 of four stamped compressive leaf contacts 16 attached in place, e.g., welded, to feedthrough contacts (not shown). Each line 12, 14 of contacts 16 is arranged to couple with contacts of a single lead. The contacts 16 are characterized by a major dimension 18 that is greater than a minor dimension 20, and each contact is oriented relative to a line axis 22 for a lead such that its major dimension 18 is transverse to the line axis.

With reference to FIG. 101, a connector assembly having a feedthrough assembly 30 configured in accordance with embodiments disclosed herein can accommodate four leads in about the same amount of space as the conventional feedthrough assembly of FIG. 100. Accordingly, the connector assemblies disclosed herein can be designed into a modified implantable medical device without having to expand the size of the device.

The feedthrough assembly 30 of FIG. 101 includes four lines 32, 34, 36, 38 of contacts 40 (instead of only two), where each line of contacts is arranged to couple with the contacts of a lead. In order to double the contact 40 density, the disclosed feedthrough assemblies use smaller compressive contacts configured as contact rings, contact ring assemblies, leaf spring contacts, torsion spring contacts, or torsion spring contact assemblies, which assure adequate contact deflection capability in a smaller contact footprint.

In the feedthrough assembly 30 shown FIG. 101, the contacts 40 correspond to contact rings or contact ring assemblies as described above with reference to FIGS. 1-10B and are characterized by a major dimension 42 that is greater than a minor dimension 44, and each contact is oriented relative to a line axis 46 for a lead such that its major dimension 18 is in-line with, or aligned along the line axis. This orientation of the contacts 40 enables the inclusion of two dual-lumen seals in a cover assembly (such as shown in FIG. 2B), where each seal is configured to receive two leads with lead-to-lead spacing of approximately 2 mm. This is in contrast to the transversely oriented contacts 16 of FIG. 100 which allows only one lead per seal.

In the example feedthrough assembly 30 shown in FIG. 101, the contacts 40 are configured as contact rings (either as a single ring or a ring assembly within a backing ring and a contact ring) and include an axis 48 that extends through an opening defined by the structure and shape of the ring, e.g., along the center of the ring, and that is transverse the line axis 46 of the lead. This orientation of the contact axis relative to the line axis is opposite the orientation of the axis 50 of the contacts 16 of FIG. 100, wherein the contact axis is aligned with the line axis 22. During compression of the ring contacts 40, such as shown in FIG. 10B, the compressive forces are directed toward the center axis 48.

In other configurations disclosed herein, the contacts 40 may be configured as leaf spring contact assemblies, such as shown in FIGS. 21-36 and FIGS. 84-99. Like the ring contacts, the leaf spring contact assemblies include a contact axis 48 that extends through an opening defined by the structure and shape of the leaf spring, and that is transverse the line axis 46 for a lead.

In other configurations disclosed herein, the contacts 40 may be configured as torsion-spring contacts such as shown in FIGS. 39-58 and FIGS. 66-83, or torsion spring contact assemblies such as shown in FIGS. 59-65. In these configurations, the contacts may be considered to include an axis that extends through an opening defined by the structure and shape of the contact, e.g., through the attachment end of the contact and transverse to the surface of the feedthrough substrate, and that is also transverse the line axis 46 for a lead. This orientation of the contact axis relative to the line axis is different than the orientation of the axis 50 of the contacts 16 of FIG. 100, wherein the contact axis is aligned with the line axis 22. During deflection of the torsion spring contacts, such as shown in FIGS. 51 and 52, the deflection forces are directed along the axis of the contact.

The capability of adding leads to a device, e.g., an implantable neurostimulator, enables the device to potentially sense electrographic abnormalities and provide neurostimulation treatment in more locations of the human body. The additional locations of sensing and treatment has the potential to provide broader and better treatment of neurological disorders.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A connector assembly of an implantable medical device, the connector assembly comprising:
    a cover assembly having an aperture, the cover assembly configured to receive a connector end of at least one lead including a lead contact, and to align the lead contact with the aperture;
    a feedthrough assembly configured to couple with the cover assembly and including a feedthrough contact; and
    a detached electrical contact between the feedthrough contact and the aperture when the cover assembly and feedthrough assembly are coupled, the detached electrical contact comprising a first surface facing the feedthrough contact and a second surface facing the aperture, wherein the detached electrical contact is not bonded or welded to the feedthrough contact and the detached electrical contact is configured to allow for a compression connection with the feedthrough contacts when the cover assembly is coupled to the feedthrough assembly.

2. The connector assembly of claim 1, wherein the detached electrical contact is retained by the feedthrough assembly.

3. The connector assembly of claim 2, wherein the feedthrough assembly comprises:
    a feedthrough subassembly having a recess, wherein the feedthrough contact is within the recess; and
    a contact interposer assembly configured to retain the detached electrical contact and to be retained in the recess to align the detached electrical contact with the feedthrough contact.

4. The connector assembly of claim 3, wherein the feedthrough contact is one of a feedthrough pin or a conductive surface.

5. A connector assembly of an implantable medical device, the connector assembly comprising:
    a cover assembly having an aperture, the cover assembly configured to receive a connector end of at least one lead including a lead contact, and to align the lead contact with the aperture;
    a feedthrough assembly configured to couple with the cover assembly and including a feedthrough contact; and
    a detached electrical contact between the feedthrough contact and the aperture when the cover assembly and feedthrough assembly are coupled, wherein the detached electrical contact is retained by the feedthrough assembly and comprises a first surface facing the feedthrough contact, a second surface facing the aperture, a contact ring, and a backing ring configured to fit inside the contact ring and be retained therein by a slip fit or an interference fit,
    wherein the feedthrough assembly comprises:
        a feedthrough subassembly having a recess, wherein the feedthrough contact is within the recess, and
        a contact interposer assembly configured to retain the detached electrical contact and to be retained in the recess to align the detached electrical contact with the feedthrough contact.

6. The connector assembly of claim 5, wherein the backing ring is further configured to provide an interference fit between itself and the contact interposer assembly.

7. The connector assembly of claim 6, wherein the interference fit is provided by a plurality of space apart tabs associated with the backing ring, wherein the spaced apart tabs extend into a cutout of the contact interposer assembly and a space between the spaced apart tabs provides the interference fit with the cutout.

8. The connector assembly of claim 5, wherein:
    the contact ring is continuous, and
    the backing ring is one of continuous or discontinuous, and is characterized by one or more of: a varying width around the circumference, a window through a thickness of the backing ring, and a plurality of notches spaced around the circumference.

9. The connector assembly of claim 1, wherein the detached electrical contact is retained in the aperture of the cover assembly.

10. The connector assembly of claim 9, wherein the cover assembly comprises a seal having a lumen for receiving the connector end of the at least one lead, and at least one aperture orthogonal to the lumen and configured to retain the detached electrical contact.

11. The connector assembly of claim 1, wherein:
    the feedthrough contact comprises a pair of conductive vias; and
    the detached electrical contact comprises a pair of overlapping tines corresponding to the first surface of the detached electrical contact and a rounded tip corresponding to the second surface of the detached electrical contact, wherein each of the tines is configured to couple with a corresponding one of the pair of conductive vias.

12. A connector assembly of an implantable medical device, the connector assembly comprising:
    a cover assembly having an aperture, the cover assembly configured to receive a connector end of at least one lead, the connector end including a lead contact, and to align the lead contact with the aperture;
    a feedthrough assembly configured to couple with the cover assembly and including a feedthrough contact; and
    an attached electrical contact between the feedthrough contact and the aperture when the cover assembly and feedthrough assembly are coupled, the attached electrical contact comprising an attachment feature permanently coupled to the feedthrough contact and a contact engagement feature facing the aperture,
    wherein the attached electrical contact comprises a continuous piece of material formed to include:
    the contact engagement feature; and
    a spring loop having a free side, and an attached side comprising the attachment feature,
    wherein the contact engagement feature extends from the free side in a direction of the aperture.

13. The connector assembly of claim 12, wherein the feedthrough contact comprises a feedthrough via.

14. The connector assembly of claim 12, wherein the feedthrough contact comprises a feedthrough pin.

15. A connector assembly of an implantable medical device, the connector assembly comprising:
- a cover assembly having an aperture, the cover assembly configured to receive a connector end of at least one lead, the connector end including a lead contact, and to align the lead contact with the aperture;
- a feedthrough assembly configured to couple with the cover assembly and including a feedthrough contact; and
- an attached electrical contact between the feedthrough contact and the aperture when the cover assembly and feedthrough assembly are coupled, the attached electrical contact comprising an attachment feature permanently coupled to the feedthrough contact and a contact engagement feature facing the aperture,
- wherein the attached electrical contact comprises:
- a weld plate comprising the attachment feature; and
- a continuous piece of material formed to include:
  - the contact engagement feature; and
  - a spring loop having a free side, and an attached side electrically coupled to the weld plate,
    - wherein the contact engagement feature extends from the free side in a direction of the aperture.

16. A connector assembly of an implantable medical device, the connector assembly comprising:
- a cover assembly having an aperture, the cover assembly configured to receive a connector end of at least one lead, the connector end including a lead contact, and to align the lead contact with the aperture;
- a feedthrough assembly configured to couple with the cover assembly and including a feedthrough contact; and
- an attached electrical contact between the feedthrough contact and the aperture when the cover assembly and feedthrough assembly are coupled, the attached electrical contact comprising an attachment feature permanently coupled to the feedthrough contact and a contact engagement feature facing the aperture,
- wherein the attached electrical contact comprises:
- a shroud comprising the attachment feature; and
- a continuous piece of material formed to include:
  - the contact engagement feature; and
  - a spring loop at least partially within the shroud and having a free side, and an attached side electrically coupled to the shroud,
    - wherein the contact engagement feature extends from the free side in a direction of the aperture.

* * * * *